(12) United States Patent
Zhang et al.

(10) Patent No.: US 12,559,801 B2
(45) Date of Patent: Feb. 24, 2026

(54) COMPOSITIONS AND METHODS FOR TREATING BREAST CANCER

(71) Applicants: The Regents of the University of Michigan, Ann Arbor, MI (US); Fred Hutchinson Cancer Center, Seattle, WA (US)

(72) Inventors: Yuping Zhang, Ann Arbor, MI (US); Marcin Cieslik, Ann Arbor, MI (US); Arul M. Chinnaiyan, Ann Arbor, MI (US); Christopher I. Li, Seattle, WA (US)

(73) Assignees: The Regents of the University of Michigan, Ann Arbor, MI (US); Fred Hutchinson Cancer Center, Seattle, WA (US)

( * ) Notice: Subject to any disclaimer, the term of this patent is extended or adjusted under 35 U.S.C. 154(b) by 0 days.

(21) Appl. No.: 17/674,121

(22) Filed: Feb. 17, 2022

(65) Prior Publication Data

US 2022/0259674 A1 Aug. 18, 2022

Related U.S. Application Data

(60) Provisional application No. 63/150,803, filed on Feb. 18, 2021.

(51) Int. Cl.
*C12Q 1/6886* (2018.01)
*C12Q 1/6869* (2018.01)

(52) U.S. Cl.
CPC ......... *C12Q 1/6886* (2013.01); *C12Q 1/6869* (2013.01); *C12Q 2600/118* (2013.01); *C12Q 2600/156* (2013.01); *C12Q 2600/158* (2013.01)

(58) Field of Classification Search
CPC .................................................... C12Q 1/6886
USPC ...................................................... 435/7.23
See application file for complete search history.

(56) References Cited

PUBLICATIONS

Korde et al (Breast Cancer Res Treat, 2010, 119: 685-699).*
Tockman et al (Cancer Res., 1992, 52:2711s-2718s).*
Bauer et al (Clin Cancer Res, 2010, 16(23): 681-690).*
Carey et al (Clin Cancer Res, 2007, 13(8): 2329-2334).*
Adams et al., Prognostic value of tumor-infiltrating lymphocytes in triple-negative breast cancers from two phase III randomized adjuvant breast cancer trials: ECOG 2197 and ECOG 1199. J Clin Oncol. Sep. 20, 2014;32(27):2959-66.
Aran et al., Systematic pan-cancer analysis of tumour purity. Nat Commun. Dec. 4, 2015;6:8971. 1-11.
Babina et al., Advances and challenges in targeting FGFR signalling in cancer. Nat Rev Cancer. May 2017;17(5):318-332.
Baglia et al., Alcohol, smoking, and risk of Her2-overexpressing and triple-negative breast cancer relative to estrogen receptor-positive breast cancer. Int J Cancer. Oct. 15, 2018;143(8):1849-1857.
Brockhoff et al., The presence of PD-1 positive tumor infiltrating lymphocytes in triple negative breast cancers is associated with a favorable outcome of disease. Oncotarget. Dec. 27, 2017;9(5):6201-6212.
Camarda et al., Inhibition of fatty acid oxidation as a therapy for MYC-overexpressing triple-negative breast cancer. Nat Med. Apr. 2016;22(4):427-32.
Cobleigh et al., Tumor gene expression and prognosis in breast cancer patients with 10 or more positive lymph nodes. Clin Cancer Res. Dec. 15, 2005;11(24 Pt 1):8623-31.
Curtis et al., The genomic and transcriptomic architecture of 2,000 breast tumours reveals novel subgroups. Nature. Apr. 18, 2012;486(7403):346-52.
Denkert et al., Tumor-associated lymphocytes as an independent predictor of response to neoadjuvant chemotherapy in breast cancer. J Clin Oncol. Jan. 1, 2010;28(1):105-13.
Denkert et al., Tumor-infiltrating lymphocytes and response to neoadjuvant chemotherapy with or without carboplatin in human epidermal growth factor receptor 2-positive and triple-negative primary breast cancers. J Clin Oncol. Mar. 20, 2015;33(9):983-91.
Dent et al., Triple-negative breast cancer: clinical features and patterns of recurrence. Clin Cancer Res. Aug. 1, 2007;13(15 Pt 1):4429-34.
Dieci et al., Prognostic value of tumor-infiltrating lymphocytes on residual disease after primary chemotherapy for triple-negative breast cancer: a retrospective multicenter study. Ann Oncol. Mar. 2014;25(3):611-618.
Drukker et al., A prospective evaluation of a breast cancer prognosis signature in the observational RASTER study. Int J Cancer. Aug. 15, 2013;133(4):929-36.
Gentles et al., The prognostic landscape of genes and infiltrating immune cells across human cancers. Nat Med. Aug. 2015;21(8):938-945.
Gonzalez-Angulo et al., Incidence and outcome of BRCA mutations in unselected patients with triple receptor-negative breast cancer. Clin Cancer Res. Mar. 1, 2011;17(5):1082-9.
Györffy et al., An online survival analysis tool to rapidly assess the effect of 22,277 genes on breast cancer prognosis using microarray data of 1,809 patients. Breast Cancer Res Treat. Oct. 2010;123(3):725-31.
Hollmén et al., Characterization of macrophage—cancer cell crosstalk in estrogen receptor positive and triple-negative breast cancer. Sci Rep. Mar. 17, 2015;5:9188. 1-10.
Jiang et al., Genomic and Transcriptomic Landscape of Triple-Negative Breast Cancers: Subtypes and Treatment Strategies. Cancer Cell. Mar. 18, 2019;35(3):428-440.e5.
Kardos et al., Claudin-low bladder tumors are immune infiltrated and actively immune suppressed. JCI Insight. Mar. 17, 2016;1(3):e85902. 1-17.
Kawazu et al., Integrative analysis of genomic alterations in triple-negative breast cancer in association with homologous recombination deficiency. PLoS Genet. Jun. 21, 2017;13(6):e1006853. 1-23.
Kirsch et al., T-cell receptor profiling in cancer. Mol Oncol. Dec. 2015;9(10):2063-70.

(Continued)

*Primary Examiner* — Sean E Aeder
(74) *Attorney, Agent, or Firm* — Casimir Jones, S.C.; Tanya A. Arenson

(57) ABSTRACT

Provided herein are compositions and methods for cancer diagnosis, research and therapy, including but not limited to, cancer markers. In particular, provided herein are methods of treating basal-like breast cancer based on expression levels of a panel of cancer markers.

7 Claims, 15 Drawing Sheets

(56)        References Cited

PUBLICATIONS

Kitano et al., Tumour-infiltrating lymphocytes are correlated with higher expression levels of PD-1 and PD-L1 in early breast cancer. ESMO Open. May 2, 2017;2(2):e000150.

Lee et al., Prognostic and predictive value of NanoString-based immune-related gene signatures in a neoadjuvant setting of triple-negative breast cancer: relationship to tumor-infiltrating lymphocytes. Breast Cancer Res Treat. Jun. 2015;151(3):619-27.

Lehmann et al., Refinement of Triple-Negative Breast Cancer Molecular Subtypes: Implications for Neoadjuvant Chemotherapy Selection. PLoS One. Jun. 16, 2016;11(6):e0157368. 1-22.

Li et al., Biomarkers Predicting Pathologic Complete Response to Neoadjuvant Chemotherapy in Breast Cancer. Am J Clin Pathol. Jun. 2016;145(6):871-8.

Lin et al., Clinicopathologic features, patterns of recurrence, and survival among women with triple-negative breast cancer in the National Comprehensive Cancer Network. Cancer. Nov. 15, 2012;118(22):5463-72.

Liu et al., CD8+ lymphocyte infiltration is an independent favorable prognostic indicator in basal-like breast cancer. Breast Cancer Res. Mar. 15, 2012;14(2):R48. 1-14.

Loi et al., Prognostic and predictive value of tumor-infiltrating lymphocytes in a phase III randomized adjuvant breast cancer trial in node-positive breast cancer comparing the addition of docetaxel to doxorubicin with doxorubicin-based chemotherapy: BIG 02-98. J Clin Oncol. Mar. 1, 2013;31(7):860-7.

Mori et al., A dominant-negative FGF1 mutant (the R50E mutant) suppresses tumorigenesis and angiogenesis. PLoS One. 2013;8(2):e57927. 1-9.

Nanda R, Liu MC, Yau C, Asare S, Hylton N, Veer LV, et al. Pembrolizumab plus standard neoadjuvant therapy for high-risk breast cancer (BC): Results from I-SPY 2. J Clin Orthod. American Society of Clinical Oncology; 2017;35:506-506.

Ono et al., Tumor-infiltrating lymphocytes are correlated with response to neoadjuvant chemotherapy in triple-negative breast cancer. Breast Cancer Res Treat. Apr. 2012;132(3):793-805.

Paquet et al., Absolute assignment of breast cancer intrinsic molecular subtype. J Natl Cancer Inst. Dec. 4, 2014;107(1):357. 1-9.

Pelekanou et al., Effect of neoadjuvant chemotherapy on tumor-infiltrating lymphocytes and PD-L1 expression in breast cancer and its clinical significance. Breast Cancer Res. Aug. 7, 2017;19(1):91. 1-11.

Pelekanou et al., Effects of neoadjuvant chemotherapy (NAC) on tumor infiltrating lymphocytes (TIL) and PD-L1 expression in the SWOG S0800 clinical trial. J Clin Orthod. American Society of Clinical Oncology; 2017;35:519-519.

Pereira et al., FKBP5 expression in human adipose tissue increases following dexamethasone exposure and is associated with insulin resistance. Metabolism. Sep. 2014;63(9):1198-208.

Perou et al., Clinical implementation of the intrinsic subtypes of breast cancer. Lancet Oncol. Aug. 2010;11(8):718-9; author reply 720-1.

Perou et al., Molecular portraits of human breast tumours. Nature. Aug. 17, 2000;406(6797):747-52.

Petralia et al., A new method for constructing tumor specific gene co-expression networks based on samples with tumor purity heterogeneity. Bioinformatics. Jul. 1, 2018;34(13):i528-i536.

Schmid et al., Atezolizumab and Nab-Paclitaxel in Advanced Triple-Negative Breast Cancer. N Engl J Med. Nov. 29, 2018;379(22):2108-2121.

Schmid et al., Pembrolizumab for Early Triple-Negative Breast Cancer. N Engl J Med. Feb. 27, 2020;382(9):810-821.

Shah et al., The clonal and mutational evolution spectrum of primary triple-negative breast cancers. Nature. Apr. 4, 2012;486(7403):395-9.

Sørlie et al., Gene expression patterns of breast carcinomas distinguish tumor subclasses with clinical implications. Proc Natl Acad Sci U S A. Sep. 11, 2001;98(19):10869-74.

Sørlie et al., Repeated observation of breast tumor subtypes in independent gene expression data sets. Proc Natl Acad Sci U S A. Jul. 8, 2003;100(14):8418-23.

Sousa et al., Human breast cancer cells educate macrophages toward the M2 activation status. Breast Cancer Res. Aug. 5, 2015;17(1):101. 1-14.

The Cancer Genome Atlas Network. Comprehensive molecular portraits of human breast tumours. Nature. Oct. 4, 2012;490(7418):61-70.

Trivers et al., The epidemiology of triple-negative breast cancer, including race. Cancer Causes Control. Sep. 2009;20(7):1071-82.

Voorwerk et al., Immune induction strategies in metastatic triple-negative breast cancer to enhance the sensitivity to PD-1 blockade: the TONIC trial. Nat Med. Jun. 2019;25(6):920-928.

Wang et al., Aiolos regulates B cell activation and maturation to effector state. Immunity. Oct. 1998;9(4):543-53.

Wells et al., Following the fate of individual T cells throughout activation and clonal expansion. Signals from T cell receptor and CD28 differentially regulate the induction and duration of a proliferative response. J Clin Invest. Dec. 15, 1997;100(12):3173-83.

Yadav et al., An assessment of computational methods for estimating purity and clonality using genomic data derived from heterogeneous tumor tissue samples. Brief Bioinform. Mar. 2015;16(2):232-41.

Yoshihara et al., Inferring tumour purity and stromal and immune cell admixture from expression data. Nat Commun. 2013;4:2612. 1-11.

* cited by examiner

A

B          C

A                                                    FGF1

B                                                    SLC27A6

C

A

B

C

D

E

COMPOSITIONS AND METHODS FOR TREATING BREAST CANCER

STATEMENT OF RELATED APPLICATIONS

This application claims priority to U.S. Provisional Patent Application No. 63/150,803, filed Feb. 18, 2021, the entire contents of which are incorporated herein by reference for all purposes.

STATEMENT REGARDING FEDERALLY SPONSORED RESEARCH OR DEVELOPMENT

This invention was made with government support under CA214170 and CA148143 awarded by the National Institutes of Health, and W81XWH-12-1-0080 and W81XWH-12-1-0079 awarded by the U.S. Army Medical Research and Development Command. The government has certain rights in the invention.

FIELD OF THE DISCLOSURE

Provided herein are compositions and methods for cancer diagnosis, research and therapy, including but not limited to, cancer markers. In particular, provided herein are methods of treating basal-like breast cancer based on expression levels of a panel of cancer markers.

BACKGROUND OF THE DISCLOSURE

Breast cancer is a heterogeneous disease with intrinsic subtypes revealed by histopathological and molecular profiling (1-4). Triple-negative breast cancers (TNBC), which lack expression of the estrogen receptor (ER) and progesterone receptor (PR) and do not overexpress HER2, represent 16% of all breast cancers and have a poorer survival rate (70% five-year survival rate) compared to hormone receptor-positive tumors (90-95% five-year survival rates) (4-7). Basal-like breast cancer (BLBC) is the most common type of TNBC, accounting for 70% of this subtype. Compared to other subtypes, BLBC is more common among younger, African American, and Hispanic women and is molecularly characterized by increased frequencies of germline aberrations in the homology-directed DNA repair pathway (8). Compared to hormone receptor-positive tumors, BLBCs are also associated with substantial genetic heterogeneity in terms of driver aberrations (9), passenger mutations, and/or genetic instability, as well as clonal heterogeneity (10).

Management of BLBC patients is associated with a number of major clinical challenges. BLBC patients have poor prognoses and recurrences that tend to occur within the first five years after initial diagnosis, which is in contrast to hormone receptor-positive disease where recurrences five-plus years post-diagnosis are more common (6,11). At present, the standard of care for non-metastatic BLBC patients is primary local treatment (total mastectomy or lumpectomy with radiation) and either adjuvant or neoadjuvant anthracycline taxane-based chemotherapy. However, there is no BLBC-specific test that differentiates patients who will rapidly fail standard treatment versus those who will remain event free for five years or longer.

Additional markers for BLBC, diagnosis, prognosis, and customized treatment are needed.

SUMMARY OF THE DISCLOSURE

Provided herein are compositions and methods for cancer diagnosis, research and therapy, including but not limited to, cancer markers. In particular, provided herein are methods of treating basal-like breast cancer based on expression levels of a panel of cancer markers.

Basal-like breast cancer (BLBC) is a particularly aggressive intrinsic molecular subtype of breast cancer that lacks targeted therapies. There is also no clinically useful test to risk-stratify BLBC patients. Experiments described herein used a correlative genomic sequencing study using a matched pairs design with validation in five independent cohorts to identify non-redundant and uncorrelated prognostic genes. By simultaneously interrogating the tumor and its microenvironment, a compound risk model that stratified patients into low-, medium-, and high-risk groups, with a 14%/56%/74% chance of recurrence, respectively was identified. The prognostic model informs clinical decision making for BLBC patients as it identifies those at high-risk of rapidly progressing on standard chemotherapy, as well as those who may benefit from alternative first line therapies.

For example, in some embodiments, provided herein is a method of detecting altered expression levels of cancer markers, comprising: assaying the level of expression of two or more (e.g., 2, 3, 4, 5, 6, 7, 8, 9, 10, 15, 20, or all) cancer markers selected from, for example, makorin ring finger protein 2 (MKRN2), ral guanine nucleotide dissociation stimulator like 2 (RGL2), fibroblast growth factor 1 (FGF1), FK506 binding protein 5 (FKBP5), ATPase H+ transporting accessory protein 1 like (ATP6AP1L), E74 like ETS transcription factor 3 (ELF3), natural cytotoxicity triggering receptor 1 (NCR1), SLAM family member 6 (SLAMF6), actin filament associated protein 1 like 1 (AFAP1L1), GLIS family zinc finger 1 (GLIS1), DnaJ heat shock protein family (Hsp40) member C1 (DNAJC1), EPH receptor B4 (EPHB4), transmembrane protein 30A (TMEM30A), C-type lectin domain family 4 member E (CLEC4E), lemur tyrosine kinase 2 (LMTK2), phosphate cytidylyltransferase 1, choline, alpha (PCYT1A), melanoregulin (MREG), hepatitis A virus cellular receptor 1 (HAVCR1), inhibitor of growth family member 4 (ING4), IKAROS family zinc finger 3 (IKZF3), or absent in melanoma 2, Interferon-Inducible Protein (AIM2) in a sample from a subject diagnosed with breast cancer. In some embodiments, the method further comprises measuring the level of expression of one or more genes from Table 5.

Further embodiments provide a method of treating breast cancer, comprising: a) assaying the level of expression of two or more (e.g., 2, 3, 4, 5, 6, 7, 8, 9, 10, 15, 20, or all) cancer markers selected from the, for example, MKRN2, RGL2, FGF1, FKBP5, ATP6AP1L, ELF3, NCR1, SLAMF6, AFAP1L1, GLIS1, DNAJC1, EPHB4, TMEM30A, CLEC4E, LMTK2, PCYT1A, MREG, HAVCR1, ING4, IKZF3, or AIM2 in a sample from a subject diagnosed with breast cancer; and b) administering adjuvant chemotherapy to a subject identified as having levels of expression of the cancer markers indicative of a high risk of recurrence of the breast cancer.

Additional embodiments provide a method of characterizing or prognosing breast cancer, comprising: a) assaying the level of expression of two or more (e.g., 2, 3, 4, 5, 6, 7, 8, 9, 10, 15, 20, or all) cancer markers selected from the, for example, MKRN2, RGL2, FGF1, FKBP5, ATP6AP1L, ELF3, NCR1, SLAMF6, AFAP1L1, GLIS1, DNAJC1, EPHB4, TMEM30A, CLEC4E, LMTK2, PCYT1A, MREG, HAVCR1, ING4, IKZF3, or AIM2 in a sample from a subject diagnosed with breast cancer; and b) identifying the subject as at an increased risk of recurrence of said breast cancer based on the levels of expression of the cancer markers.

In some embodiments, the breast cancer is basal-like breast cancer (BLBC). In some embodiments, the adjuvant chemotherapy is a platinum-based chemotherapy (e.g., carboplatin or cisplatin) and/or immune checkpoint therapy. In some embodiments, the adjuvant chemotherapy comprises neoadjuvant chemotherapy.

In some embodiments, the two or more markers are IKZF3, AIM2, and ELF3. In some embodiments, the markers are two or more (e.g., 2, 3, 4, 5, 6, 7, 8, 9, 10, 11, or all) of MKRN2, FKBP5, NCR1, SLAMF6, DNAJC1, TMEM30A, CLEC4E, PCYT1A, MREG, HAVCR1, IKZF3, and AIM2 and the method further comprises administering immune checkpoint therapy.

In some embodiments, the expression is the level of mRNA or protein expressed by the cancer marker. In some embodiments, the expression is increased or decreased relative to the level in a subject not diagnosed with breast cancer or in a subject with a low risk of recurrence of breast cancer. For example, in some embodiments, expression levels of individual genes are increased or decreased as shown in Table 6.

The present disclosure is not limited to particular sample types and analysis methods. For example, in some embodiments, the sample is tissue, blood, plasma, serum, breast tissue, breast cells, or breast cancer cells. In some embodiments, the assaying is carried out utilizing a method selected from, for example, a sequencing technique, a nucleic acid hybridization technique, or a nucleic acid amplification technique. In some embodiments, the nucleic acid amplification technique is polymerase chain reaction, reverse transcription polymerase chain reaction, transcription-mediated amplification, ligase chain reaction, strand displacement amplification, or nucleic acid sequence based amplification. In some embodiments, the assaying comprises the use of a reagent selected from, for example, a pair of amplification oligonucleotides, a sequencing primer, or an oligonucleotide probe. In some embodiments, the reagent comprises one or more labels.

Yet other embodiments provide a composition, system or kit, comprising: reagents for detecting the level of expression of two or more (e.g., 2, 3, 4, 5, 6, 7, 8, 9, 10, 15, 20, or all) cancer markers selected from the, for example, MKRN2, RGL2, FGF1, FKBP5, ATP6AP1L, ELF3, NCR1, SLAMF6, AFAP1L1, GLIS1, DNAJC1, EPHB4, TMEM30A, CLEC4E, LMTK2, PCYT1A, MREG, HAVCR1, ING4, IKZF3, or AIM2. In some embodiments, the reagents detect only the described cancer markers (e.g., 2 to 21 of the markers).

Further embodiments provide the use of a composition, kit or system described herein to provide a prognosis or recommend a treatment for breast cancer.

Other embodiments provide a composition, kit or system described herein for use in providing a prognosis or recommending a treatment for breast cancer.

Additional embodiments are described herein.

DEFINITIONS

Figure 1:
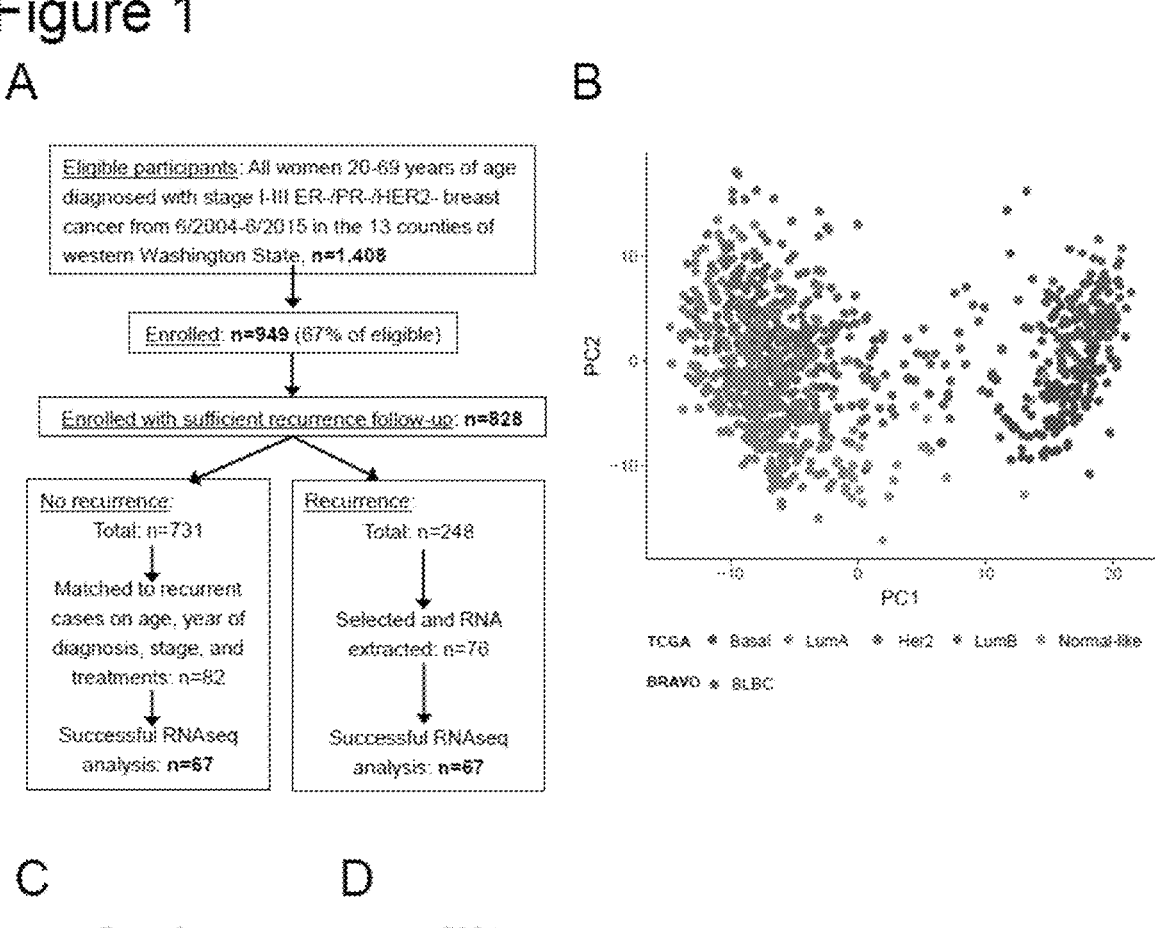
FIG. 1: Study design and delineation of a basal-like cohort. A) Consort flow diagram of the BRAVO study. B) Principal component analysis (PCA) of BLBC in the BRAVO cohort and the breast TCGA cohorts based on genes with most variable expression. PC=Principal Component. C) Estimated proportion of tumor cells (tumor purity). D) Lack of differential expression of ER (ESR1), PR (PGR), and Her2 (ERBB2), across the BRAVO breast cancer cohorts (Wilcoxon rank sum test).
Figure 1:
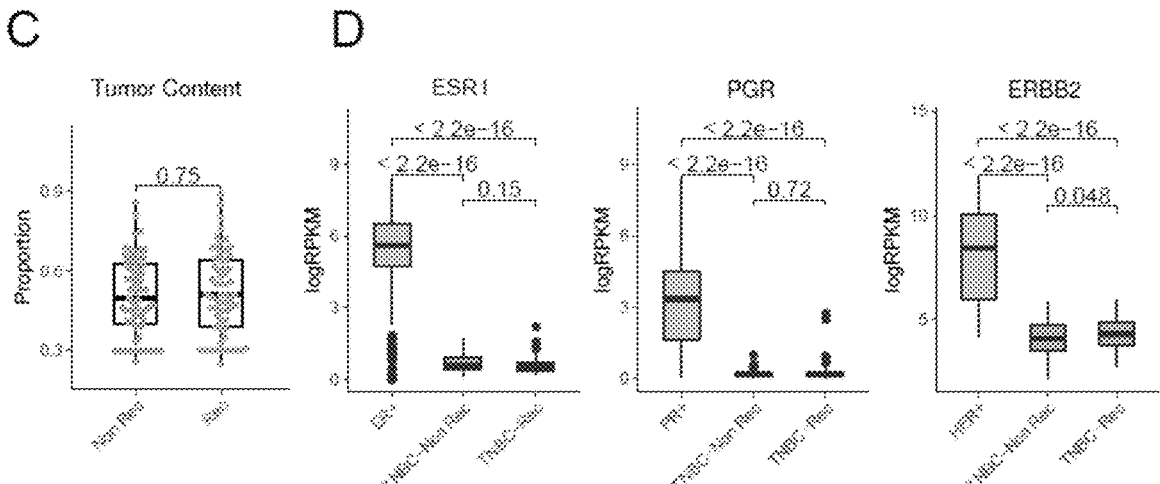

To facilitate an understanding of the present disclosure, a number of terms and phrases are defined below:

As used herein, the terms "detect", "detecting" or "detection" may describe either the general act of discovering or discerning or the specific observation of a composition. Detecting a composition may comprise determining the presence or absence of a composition. Detecting may comprise quantifying a composition. For example, detecting comprises determining the expression level of a composition. The composition may comprise a nucleic acid molecule. For example, the composition may comprise at least a portion of the cancer markers disclosed herein. Alternatively, or additionally, the composition may be a detectably labeled composition.

As used herein, the term "subject" refers to any organisms that are screened using the diagnostic methods described herein. Such organisms preferably include, but are not limited to, mammals (e.g., murines, simians, equines, bovines, porcines, canines, felines, and the like), and most preferably includes humans. Alternatively, the organism is an avian, amphibian, reptile or fish.

The term "diagnosed," as used herein, refers to the recognition of a disease by its signs and symptoms, or genetic analysis, pathological analysis, histological analysis, and the like.

As used herein, the term "characterizing cancer in a subject" refers to the identification of one or more properties of a cancer sample in a subject, including but not limited to, the presence of benign, pre-cancerous or cancerous tissue, the stage of the cancer, and the subject's prognosis. Cancers may be characterized by the identification of the expression of one or more cancer marker genes, including but not limited to, the cancer markers disclosed herein.

As used herein, the term "stage of cancer" refers to a qualitative or quantitative assessment of the level of advancement of a cancer. Criteria used to determine the stage of a cancer include, but are not limited to, the size of the tumor and the extent of metastases (e.g., localized or distant).

As used herein, the term "nucleic acid molecule" refers to any nucleic acid containing molecule, including but not limited to, DNA or RNA. The nucleic acid molecule may comprise one or more nucleotides. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethyl-aminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D- mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragments are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "oligonucleotide," refers to a short length of single-stranded polynucleotide chain. Oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer". Oligonucleotides can form secondary and tertiary structures by self-hybridizing or by hybridizing to other polynucleotides. Such structures can include, but are not limited to, duplexes, hairpins, cruciforms, bends, and triplexes.

The term "label" as used herein refers to any atom or molecule that can be used to provide a detectable (preferably quantifiable) effect, and that can be attached to a nucleic acid or protein. Labels include but are not limited to dyes; radiolabels such as $^{32}$P; binding moieties such as biotin; haptens such as digoxgenin; luminogenic, phosphorescent or fluorogenic moieties; and fluorescent dyes alone or in combination with moieties that can suppress or shift emission spectra by fluorescence resonance energy transfer (FRET). Labels may provide signals detectable by fluorescence, radioactivity, colorimetry, gravimetry, X-ray diffraction or absorption, magnetism, enzymatic activity, and the like. A label may be a charged moiety (positive or negative charge) or alternatively, may be charge neutral. Labels can include or consist of nucleic acid or protein sequence, so long as the sequence comprising the label is detectable. In some embodiments, nucleic acids are detected directly without a label (e.g., directly reading a sequence).

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Such examples are not however to be construed as limiting the sample types applicable to the present disclosure.

DETAILED DESCRIPTION OF THE DISCLOSURE

Provided herein are compositions and methods for cancer diagnosis, research and therapy, including but not limited to, cancer markers. In particular, provided herein are methods of treating basal-like breast cancer based on expression levels of a panel of cancer markers.

The host-tumor immune response has been explored as a prognostic indicator for TNBC and BLBC (12,13). More robust tumor immune cell infiltration and higher expression of immune-related genes have been associated with better clinical outcomes. For example, multiple studies have demonstrated that tumor infiltrating lymphocytes (TILs) are prognostic in early stage TNBC, with higher degrees of immune cell infiltration correlating with improved clinical outcomes (14-21). More specifically, increased TILs are associated with increased likelihood of achieving pathologic complete response (pCR), an independent favorable prognostic indicator, following administration of neoadjuvant chemotherapy (18,20,21). Furthermore, for patients who do not achieve pCR following neoadjuvant chemotherapy administration, increased TILs in residual disease specimens have also been correlated with improved clinical outcomes (17,22). TILs are also positively correlated with PD-1/PD-L1 expression in tumor and surrounding stroma (23-25), indicating that PD-1/PD-L1 inhibitors may prove effective in TNBC that is already primed with a robust tumor immune response. Indeed, the addition of pembrolizumab, a PD-1 inhibitor, to neoadjuvant chemotherapy significantly improved rates of pCR in patients with advanced triple-negative disease (26). Most recently, atezolizumab, a PD-L1 inhibitor, has been approved for metastatic TNBC and is in the phase III IMpassion130 (NCT02425891) trial (27), and patients with PD-L1 have gained the largest benefits. Lastly, higher gene expression levels of T-cell receptor signaling pathway components, Th1-related cytokines, and B-cell markers have also been correlated with increased likelihood of pCR after neoadjuvant chemotherapy and overall survival (28).

Use of immune checkpoint inhibitors (ICI), however, may not be appropriate in the upfront treatment of all patients with TNBC for two primary reasons: 1) not all patients will benefit from immunotherapy treatment, and 2) some patients will have an excellent prognosis with chemotherapy alone, thus not justifying the potential added toxicity and costs associated with immunotherapy. Given this, there is an urgent clinical need to risk-stratify patients with BLBC in ways that will meaningfully inform therapeutic decision making.

Experiments described herein used RNA sequencing on tumor samples from 67 BLBC patients that developed a recurrence and 67 recurrence-free controls. These patients were selected from a large population-based prospective cohort of 1,408 TNBC patients 20-69 years of age diagnosed from 2004-2012. The prognostic gene set developed through this discovery set was then evaluated in five independent cohorts of triple-negative patients, including validation in large cohorts from TCGA (2), METABRIC (3), and Gyorffy et al (29).

Accordingly, provided herein are diagnostic, prognostic, screening, and therapeutic methods for use in treating patients with BLBC. Exemplary methods are described herein.

I. Methods of Assaying Marker Expression

As described herein, embodiments of the present disclosure provide diagnostic, screening, and therapeutic methods that utilize the detection of the expression level of two or more (e.g., 2, 3, 4, 5, 6, 7, 8, 9, 10, 15, 20, or all) cancer markers selected from, for example, MKRN2, RGL2, FGF1, FKBP5, ATP6AP1L, ELF3, NCR1, SLAMF6, AFAP1L1, GLIS1, DNAJC1, EPHB4, TMEM30A, CLEC4E, LMTK2, PCYT1A, MREG, HAVCR1, ING4, IKZF3, or AIM2. Exemplary, non-limiting methods are described herein.

The cancer markers of the present disclosure are detected using a variety of nucleic acid techniques, including but not limited to: nucleic acid sequencing; nucleic acid hybridization; and, nucleic acid amplification.

In some embodiments, nucleic acid sequencing methods are utilized (e.g., for detection of amplified nucleic acids). In some embodiments, the technology provided herein finds use in a Second Generation (a.k.a. Next Generation or Next-Gen), Third Generation (a.k.a. Next-Next-Gen), or Fourth Generation (a.k.a. N3-Gen) sequencing technology including, but not limited to, pyrosequencing, sequencing-by-ligation, single molecule sequencing, sequence-by-synthesis (SBS), semiconductor sequencing, massive parallel clonal, massive parallel single molecule SBS, massive parallel single molecule real-time, massive parallel single molecule real-time nanopore technology, etc. Morozova and Marra provide a review of some such technologies in *Genomics*, 92: 255 (2008), herein incorporated by reference in its entirety. Those of ordinary skill in the art will recognize that because RNA is less stable in the cell and more prone to nuclease attack experimentally RNA is usually reverse transcribed to DNA before sequencing. A number of DNA sequencing techniques are suitable, including fluorescence-based sequencing methodologies (See, e.g., Birren et al., Genome Analysis: Analyzing DNA, 1, Cold Spring Harbor, N.Y.; herein incorporated by reference in its entirety). In some embodiments, the technology finds use in automated sequencing techniques understood in that art. In some embodiments, the present technology finds use in parallel sequencing of partitioned amplicons (PCT Publication No: WO2006084132 to Kevin McKernan et al., herein incorporated by reference in its entirety). In some embodiments, the technology finds use in DNA sequencing by parallel oligonucleotide extension (See, e.g., U.S. Pat. No. 5,750,341 to Macevicz et al., and U.S. Pat. No. 6,306,597 to Macevicz et al., both of which are herein incorporated by reference in their entireties). Additional examples of sequencing techniques in which the technology finds use include the Church polony technology (Mitra et al., 2003, Analytical Biochemistry 320, 55-65; Shendure et al., 2005 Science 309, 1728-1732; U.S. Pat. Nos. 6,432,360, 6,485, 944, 6,511,803; herein incorporated by reference in their entireties), the 454 picotiter pyrosequencing technology (Margulies et al., 2005 Nature 437, 376-380; US 20050130173; herein incorporated by reference in their entireties), the Solexa single base addition technology (Bennett et al., 2005, Pharmacogenomics, 6, 373-382; U.S. Pat. Nos. 6,787,308; 6,833,246; herein incorporated by reference in their entireties), the Lynx massively parallel signature sequencing technology (Brenner et al. (2000). Nat. Biotechnol. 18:630-634; U.S. Pat. Nos. 5,695,934; 5,714,330; herein incorporated by reference in their entireties), and the Adessi PCR colony technology (Adessi et al. (2000). Nucleic Acid Res. 28, E87; WO 00018957; herein incorporated by reference in its entirety).

Illustrative non-limiting examples of nucleic acid hybridization techniques include, but are not limited to, in situ hybridization (ISH), microarray, and Southern or Northern blot. In situ hybridization (ISH) is a type of hybridization that uses a labeled complementary DNA or RNA strand as a probe to localize a specific DNA or RNA sequence in a portion or section of tissue (in situ), or, if the tissue is small enough, the entire tissue (whole mount ISH). DNA ISH can be used to determine the structure of chromosomes. RNA ISH is used to measure and localize mRNAs and other transcripts (e.g., cancer markers) within tissue sections or whole mounts. Sample cells and tissues are usually treated to fix the target transcripts in place and to increase access of the probe. The probe hybridizes to the target sequence at elevated temperature, and then the excess probe is washed away. The probe that was labeled with either radio-, fluorescent- or antigen-labeled bases is localized and quantitated in the tissue using either autoradiography, fluorescence microscopy or immunohistochemistry, respectively. ISH can also use two or more probes, labeled with radioactivity or the other non-radioactive labels, to simultaneously detect two or more transcripts.

In some embodiments, cancer markers are detected using fluorescence in situ hybridization (FISH). In some embodiments, FISH assays utilize bacterial artificial chromosomes (BACs). These have been used extensively in the human genome sequencing project (see *Nature* 409: 953-958 (2001)) and clones containing specific BACs are available through distributors that can be located through many sources, e.g., NCBI. Each BAC clone from the human genome has been given a reference name that unambiguously identifies it. These names can be used to find a corresponding GenBank sequence and to order copies of the clone from a distributor.

The present disclosure further provides a method of performing a FISH assay on the patient sample. The methods disclosed herein may comprise performing a FISH assay on one or more cells, tissues, organs, or fluids surrounding such cells, tissues and organs. In some instances, the methods disclosed herein further comprise performing a FISH assay on human breast cells, human breast tissue or on the fluid surrounding said human breast cells or human breast tissue. Guidance regarding methodology may be obtained from many references including: *In situ Hybridization: Medical Applications* (eds. G. R. Coulton and J. de Belleroche), Kluwer Academic Publishers, Boston (1992); *In situ Hybridization: In Neurobiology; Advances in Methodology* (eds. J. H. Eberwine, K. L. Valentino, and J. D. Barchas), Oxford University Press Inc., England (1994); *In situ Hybridization: A Practical Approach* (ed. D. G. Wilkinson), Oxford University Press Inc., England (1992)); Kuo, et al., *Am. J. Hum. Genet.* 49:112-119 (1991); Klinger, et al., *Am. J. Hum. Genet.* 51:55-65 (1992); and Ward, et al., *Am. J. Hum. Genet.* 52:854-865 (1993)). There are also kits that are commercially available and that provide protocols for performing FISH assays (available from e.g., Oncor, Inc., Gaithersburg, MD). Patents providing guidance on methodology include U.S. Pat. Nos. 5,225,326; 5,545,524; 6,121, 489 and 6,573,043. All of these references are hereby incorporated by reference in their entirety and may be used along with similar references in the art and with the information provided in the Examples section herein to establish procedural steps convenient for a particular laboratory.

The one or more cancer markers may be detected by conducting one or more hybridization reactions. The one or more hybridization reactions may comprise one or more hybridization arrays, hybridization reactions, hybridization chain reactions, isothermal hybridization reactions, nucleic acid hybridization reactions, or a combination thereof. The one or more hybridization arrays may comprise hybridization array genotyping, hybridization array proportional sensing, DNA hybridization arrays, macroarrays, microarrays, high-density oligonucleotide arrays, genomic hybridization arrays, comparative hybridization arrays, or a combination thereof.

Different kinds of biological assays are called microarrays including, but not limited to: DNA microarrays (e.g., cDNA microarrays and oligonucleotide microarrays); protein microarrays; tissue microarrays; transfection or cell microarrays; chemical compound microarrays; and, antibody microarrays. A DNA microarray, commonly known as gene chip, DNA chip, or biochip, is a collection of microscopic DNA spots attached to a solid surface (e.g., glass, plastic or silicon chip) forming an array for the purpose of expression profiling or monitoring expression levels for thousands of genes simultaneously. The affixed DNA segments are known as probes, thousands of which can be used in a single DNA microarray. Microarrays can be used to identify disease genes or transcripts (e.g., cancer markers) by comparing gene expression in disease and normal cells. Microarrays can be fabricated using a variety of technologies, including but not limiting: printing with fine-pointed pins onto glass slides; photolithography using pre-made masks; photolithography using dynamic micromirror devices; ink-jet printing; or, electrochemistry on microelectrode arrays.

The methods disclosed herein may comprise conducting one or more amplification reactions. Nucleic acids (e.g., cancer markers) may be amplified prior to or simultaneous with detection. Conducting one or more amplification reactions may comprise one or more PCR-based amplifications, non-PCR based amplifications, or a combination thereof. Illustrative non-limiting examples of nucleic acid amplification techniques include, but are not limited to, polymerase chain reaction (PCR), reverse transcription polymerase chain reaction (RT-PCR), nested PCR, linear amplification, multiple displacement amplification (MDA), real-time SDA, rolling circle amplification, circle-to-circle amplification transcription-mediated amplification (TMA), ligase chain reaction (LCR), strand displacement amplification (SDA), and nucleic acid sequence based amplification (NASBA). Those of ordinary skill in the art will recognize that certain amplification techniques (e.g., PCR) require that RNA be reversed transcribed to DNA prior to amplification (e.g., RT-PCR), whereas other amplification techniques directly amplify RNA (e.g., TMA and NASBA).

The polymerase chain reaction (U.S. Pat. Nos. 4,683,195, 4,683,202, 4,800,159 and 4,965,188, each of which is herein incorporated by reference in its entirety), commonly referred to as PCR, uses multiple cycles of denaturation, annealing of primer pairs to opposite strands, and primer extension to exponentially increase copy numbers of a target nucleic acid sequence. In a variation called RT-PCR, reverse transcriptase (RT) is used to make a complementary DNA (cDNA) from mRNA, and the cDNA is then amplified by PCR to produce multiple copies of DNA. For other various permutations of PCR see, e.g., U.S. Pat. Nos. 4,683,195, 4,683,202 and 4,800,159; Mullis et al., *Meth. Enzymol.* 155:

335 (1987); and, Murakawa et al., *DNA* 7: 287 (1988), each of which is herein incorporated by reference in its entirety.

Transcription mediated amplification (U.S. Pat. Nos. 5,480,784 and 5,399,491, each of which is herein incorporated by reference in its entirety), commonly referred to as TMA, synthesizes multiple copies of a target nucleic acid sequence autocatalytically under conditions of substantially constant temperature, ionic strength, and pH in which multiple RNA copies of the target sequence autocatalytically generate additional copies. See, e.g., U.S. Pat. Nos. 5,399, 491 and 5,824,518, each of which is herein incorporated by reference in its entirety. In a variation described in U.S. Publ. No. 20060046265 (herein incorporated by reference in its entirety), TMA optionally incorporates the use of blocking moieties, terminating moieties, and other modifying moieties to improve TMA process sensitivity and accuracy.

The ligase chain reaction (Weiss, R., *Science* 254: 1292 (1991), herein incorporated by reference in its entirety), commonly referred to as LCR, uses two sets of complementary DNA oligonucleotides that hybridize to adjacent regions of the target nucleic acid. The DNA oligonucleotides are covalently linked by a DNA ligase in repeated cycles of thermal denaturation, hybridization and ligation to produce a detectable double-stranded ligated oligonucleotide product.

Strand displacement amplification (Walker, G. et al., *Proc. Natl. Acad. Sci. USA* 89: 392-396 (1992); U.S. Pat. Nos. 5,270,184 and 5,455,166, each of which is herein incorporated by reference in its entirety), commonly referred to as SDA, uses cycles of annealing pairs of primer sequences to opposite strands of a target sequence, primer extension in the presence of a dNTPaS to produce a duplex hemiphosphorothioated primer extension product, endonuclease-mediated nicking of a hemimodified restriction endonuclease recognition site, and polymerase-mediated primer extension from the 3' end of the nick to displace an existing strand and produce a strand for the next round of primer annealing, nicking and strand displacement, resulting in geometric amplification of product. Thermophilic SDA (tSDA) uses thermophilic endonucleases and polymerases at higher temperatures in essentially the same method (EP Pat. No. 0 684 315).

Other amplification methods include, for example: nucleic acid sequence based amplification (U.S. Pat. No. 5,130,238, herein incorporated by reference in its entirety), commonly referred to as NASBA; one that uses an RNA replicase to amplify the probe molecule itself (Lizardi et al., *BioTechnol.* 6: 1197 (1988), herein incorporated by reference in its entirety), commonly referred to as Qβ replicase; a transcription based amplification method (Kwoh et al., *Proc. Natl. Acad. Sci. USA* 86:1173 (1989)); and, self-sustained sequence replication (Guatelli et al., *Proc. Natl. Acad. Sci. USA* 87: 1874 (1990), each of which is herein incorporated by reference in its entirety). For further discussion of known amplification methods see Persing, David H., "In Vitro Nucleic Acid Amplification Techniques" in *Diagnostic Medical Microbiology: Principles and Applications* (Persing et al., Eds.), pp. 51-87 (American Society for Microbiology, Washington, DC (1993)).

In some embodiments, a computer-based analysis program is used to translate the raw data generated by the detection assay (e.g., the presence, absence, or amount of a given marker or markers) into data of predictive value for a clinician. The clinician can access the predictive data using any suitable means. Thus, in some preferred embodiments, the present disclosure provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present disclosure contemplates any method capable of receiving, processing, and transmitting the information to and from laboratories conducting the assays, information providers, medical personnel, and subjects. For example, in some embodiments of the present disclosure, a sample (e.g., a biopsy or a serum or urine sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (i.e., expression data), specific for the diagnostic or prognostic information desired for the subject.

The profile data is then prepared in a format suitable for interpretation by one or more medical personnel (e.g., a treating clinician, physician assistant, nurse, or pharmacist). For example, rather than providing raw expression data, the prepared format may represent a diagnosis or risk assessment (e.g., levels of the cancer markers described herein) for the subject, along with recommendations for particular treatment options. The data may be displayed to the medical personnel by any suitable method. For example, in some embodiments, the profiling service generates a report that can be printed for the medical personnel (e.g., at the point of care) or displayed to the medical personnel on a computer monitor.

In some embodiments, the information is first analyzed at the point of care or at a regional facility. The raw data is then sent to a central processing facility for further analysis and/or to convert the raw data to information useful for medical personnel or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the medical personnel, the subject, or researchers.

In some embodiments, the subject is able to directly access the data using the electronic communication system. The subject may chose further intervention or counseling based on the results.

In some embodiments, the data is used for research use. For example, the data may be used to further optimize the inclusion or elimination of markers as useful indicators of a particular condition or stage of disease or as a companion diagnostic to determine a treatment course of action.

Compositions for use in the diagnostic methods described herein include, but are not limited to, probes, amplification oligonucleotides, and the like.

The compositions and kits may comprise 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 20 or more, or 21 or more probes, pairs of probes, pairs of amplification oligonucleotide, or sequencing primers.

The probes or primers may hybridize to 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 20 or more, or 21 or more target molecules. The target molecules may be RNA, DNA, cDNA, mRNA, a portion or fragment thereof or a combination thereof. In some instances, at least a portion of the target molecules are cancer markers. The probes may hybridize to 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 20 or more, or 21 or more cancer markers disclosed herein.

Typically, the probes or primers comprise a target specific sequence. The target specific sequence may be complementary to at least a portion of the target molecule. The target specific sequence may be at least about 50% or more, 55% or more, 60% or more, 65% or more, 70% or more, 75% or more, 80% or more, 85% or more, 90% or more, 95% or more, 97% or more, 98% or more, or 100% complementary to at least a portion of the target molecule.

The target specific sequence may be at least about 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more nucleotides in length. In some instances, the target specific sequence is between about 8 to about 20 nucleotides, 10 to about 18 nucleotides, or 12 to about 16 nucleotides in length.

The compositions and kits may comprise a plurality of probes or primers, wherein the two or more probes of the plurality of probes comprise identical target specific sequences. The compositions and kits may comprise a plurality of probes, wherein the two or more probes of the plurality of probes comprise different target specific sequences.

The probes may further comprise a unique sequence. The unique sequence is noncomplementary to the cancer marker. The unique sequence may comprise a label, barcode, or unique identifier. The unique sequence may comprise a random sequence, nonrandom sequence, or a combination thereof. The unique sequence may be at least about 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 22 or more, 24 or more, 26 or more, 28 or more, 30 or more nucleotides in length. In some instances, the unique sequence is between about 8 to about 20 nucleotides, 10 to about 18 nucleotides, or 12 to about 16 nucleotides in length.

The probes may further comprise a universal sequence. The universal sequence may comprise a primer binding site. The universal sequence may enable detection of the target sequence. The universal sequence may enable amplification of the target sequence. The universal sequence may enable transcription or reverse transcription of the target sequence. The universal sequence may enable sequencing of the target sequence.

The probe or primer compositions of the present disclosure may also be provided on a solid support. The solid support may comprise one or more beads, plates, solid surfaces, wells, chips, or a combination thereof. The beads may be magnetic, antibody coated, protein A crosslinked, protein G crosslinked, streptavidin coated, oligonucleotide conjugated, silica coated, or a combination thereof. Examples of beads include, but are not limited to, Ampure beads, AMPure XP beads, streptavidin beads, agarose beads, magnetic beads, Dynabeads®, MACS® microbeads, antibody conjugated beads (e.g., anti-immunoglobulin microbead), protein A conjugated beads, protein G conjugated beads, protein A/G conjugated beads, protein L conjugated beads, oligo-dT conjugated beads, silica beads, silica-like beads, anti-biotin microbead, anti-fluorochrome microbead, and BcMag™ Carboxy-Terminated Magnetic Beads. The compositions and kits may comprise primers and primer pairs capable of amplifying target molecules, or fragments or subsequences or complements thereof. The nucleotide sequences of the target molecules may be provided in computer-readable media for in silico applications and as a basis for the design of appropriate primers for amplification of one or more target molecules.

Primers based on the nucleotide sequences of target molecules can be designed for use in amplification of the target molecules. For use in amplification reactions such as PCR, a pair of primers can be used. The exact composition of the primer sequences is not critical to the disclosure, but for most applications the primers may hybridize to specific sequences of the target molecules or the universal sequence of the probe under stringent conditions, particularly under conditions of high stringency, as known in the art. The pairs of primers are usually chosen so as to generate an amplification product of at least about 15 or more, 20 or more, 30 or more, 40 or more, 50 or more, 60 or more, 70 or more, 80 or more, 90 or more, 100 or more, 125 or more, 150 or more, 175 or more, 200 or more, 250 or more, 300 or more, 350 or more, 400 or more, 450 or more, 500 or more, 600 or more, 700 or more, 800 or more, 900 or more, or 1000 or more nucleotides. Algorithms for the selection of primer sequences are generally known, and are available in commercial software packages. These primers may be used in standard quantitative or qualitative PCR-based assays to assess transcript expression levels of target molecules. Alternatively, these primers may be used in combination with probes, such as molecular beacons in amplifications using real-time PCR.

The nucleotide sequence of the entire length of the primer does not need to be derived from the target sequence. Thus, for example, the primer may comprise nucleotide sequences at the 5' and/or 3' termini that are not derived from the target molecule. Nucleotide sequences which are not derived from the nucleotide sequence of the target molecule may provide additional functionality to the primer. For example, they may provide a restriction enzyme recognition sequence or a "tag" that facilitates detection, isolation, purification or immobilization onto a solid support. Alternatively, the additional nucleotides may provide a self-complementary sequence that allows the primer to adopt a hairpin configuration. Such configurations may be necessary for certain primers, for example, molecular beacon and Scorpion primers, which can be used in solution hybridization techniques.

The probes or primers can incorporate moieties useful in detection, isolation, purification, or immobilization, if desired. Such moieties are well-known in the art (see, for example, Ausubel et al., (1997 & updates) *Current Protocols in Molecular Biology*, Wiley & Sons, New York) and are chosen such that the ability of the probe to hybridize with its target molecule is not affected.

Examples of suitable moieties are detectable labels, such as radioisotopes, fluorophores, chemiluminophores, enzymes, colloidal particles, and fluorescent microparticles, as well as antigens, antibodies, haptens, avidin/streptavidin, biotin, haptens, enzyme cofactors/substrates, enzymes, and the like.

A label can optionally be attached to or incorporated into a probe or primer to allow detection and/or quantitation of a target polynucleotide representing the target molecule of interest. The target polynucleotide may be the expressed target molecule RNA itself, a cDNA copy thereof, or an amplification product derived therefrom, and may be the positive or negative strand, so long as it can be specifically detected in the assay being used. Similarly, an antibody may be labeled.

In certain multiplex formats, labels used for detecting different target molecules may be distinguishable. The label can be attached directly (e.g., via covalent linkage) or indirectly, e.g., via a bridging molecule or series of molecules (e.g., a molecule or complex that can bind to an assay component, or via members of a binding pair that can be incorporated into assay components, e.g. biotin-avidin or streptavidin). Many labels are commercially available in activated forms which can readily be used for such conjugation (for example through amine acylation), or labels may be attached through known or determinable conjugation schemes, many of which are known in the art.

Labels useful in the disclosure described herein include any substance which can be detected when bound to or incorporated into the target molecule. Any effective detection method can be used, including optical, spectroscopic, electrical, piezoelectrical, magnetic, Raman scattering, surface plasmon resonance, colorimetric, calorimetric, etc. A label is typically selected from a chromophore, a lumiphore, a fluorophore, one member of a quenching system, a chromogen, a hapten, an antigen, a magnetic particle, a material exhibiting nonlinear optics, a semiconductor nanocrystal, a metal nanoparticle, an enzyme, an antibody or binding portion or equivalent thereof, an aptamer, and one member of a binding pair, and combinations thereof. Quenching schemes may be used, wherein a quencher and a fluorophore as members of a quenching pair may be used on a probe, such that a change in optical parameters occurs upon binding to the target introduce or quench the signal from the fluorophore. One example of such a system is a molecular beacon. Suitable quencher/fluorophore systems are known in the art. The label may be bound through a variety of intermediate linkages. For example, a target polynucleotide may comprise a biotin-binding species, and an optically detectable label may be conjugated to biotin and then bound to the labeled target polynucleotide. Similarly, a polynucleotide sensor may comprise an immunological species such as an antibody or fragment, and a secondary antibody containing an optically detectable label may be added.

Chromophores useful in the methods described herein include any substance which can absorb energy and emit light. For multiplexed assays, a plurality of different signaling chromophores can be used with detectably different emission spectra. The chromophore can be a lumophore or a fluorophore. Typical fluorophores include fluorescent dyes, semiconductor nanocrystals, lanthanide chelates, polynucleotide-specific dyes and green fluorescent protein.

Coding schemes may optionally be used, comprising encoded particles and/or encoded tags associated with different polynucleotides of the disclosure. A variety of different coding schemes are known in the art, including fluorophores, including SCNCs, deposited metals, and RF tags.

In some embodiments, is a kit for analyzing a cancer comprising (a) a probe set comprising a plurality of probes comprising target specific sequences complementary to one or more target molecules, wherein the one or more target molecules comprise one or more cancer markers; and (b) a computer model or algorithm for analyzing an expression level and/or expression profile of the one or more target molecules in a sample. The target molecules may comprise one or more of those described herein or a combination thereof.

In some embodiments, is a kit for analyzing a cancer comprising (a) a probe set comprising a plurality of probes comprising target specific sequences complementary to one or more target molecules of a biomarker library; and (b) a computer model or algorithm for analyzing an expression level and/or expression profile of the one or more target molecules in a sample. Control samples and/or nucleic acids may optionally be provided in the kit. Control samples may include tissue and/or nucleic acids obtained from or representative of tumor samples from a healthy subject, as well as tissue and/or nucleic acids obtained from or representative of tumor samples from subjects diagnosed with a cancer.

Instructions for using the kit to perform one or more methods of the disclosure can be provided, and can be provided in any fixed medium. The instructions may be located inside or outside a container or housing, and/or may be printed on the interior or exterior of any surface thereof. A kit may be in multiplex form for concurrently detecting and/or quantitating one or more different target polynucleotides representing the expressed target molecules.

Devices useful for performing methods of the disclosure are also provided. The devices can comprise means for characterizing the expression level of a target molecule of the disclosure, for example components for performing one or more methods of nucleic acid extraction, amplification, and/or detection. Such components may include one or more of an amplification chamber (for example a thermal cycler), a plate reader, a spectrophotometer, capillary electrophoresis apparatus, a chip reader, and or robotic sample handling components. These components ultimately can obtain data that reflects the expression level of the target molecules used in the assay being employed.

The devices may include an excitation and/or a detection means. Any instrument that provides a wavelength that can excite a species of interest and is shorter than the emission wavelength(s) to be detected can be used for excitation. Commercially available devices can provide suitable excitation wavelengths as well as suitable detection component.

Exemplary excitation sources include a broadband UV light source such as a deuterium lamp with an appropriate filter, the output of a white light source such as a xenon lamp or a deuterium lamp after passing through a monochromator to extract out the desired wavelength(s), a continuous wave (cw) gas laser, a solid state diode laser, or any of the pulsed lasers. Emitted light can be detected through any suitable device or technique; many suitable approaches are known in the art. For example, a fluorimeter or spectrophotometer may be used to detect whether the test sample emits light of a wavelength characteristic of a label used in an assay.

The devices typically comprise a means for identifying a given sample, and of linking the results obtained to that sample. Such means can include manual labels, barcodes, and other indicators which can be linked to a sample vessel, and/or may optionally be included in the sample itself, for example where an encoded particle is added to the sample. The results may be linked to the sample, for example in a computer memory that contains a sample designation and a record of expression levels obtained from the sample. Linkage of the results to the sample can also include a linkage to a particular sample receptacle in the device, which is also linked to the sample identity.

The devices also comprise a means for correlating the expression levels of the target molecules being studied with a prognosis of disease outcome. Such means may comprise one or more of a variety of correlative techniques, including lookup tables, algorithms, multivariate models, and linear or nonlinear combinations of expression models or algorithms. The expression levels may be converted to one or more likelihood scores, reflecting a likelihood that the patient providing the sample may exhibit a particular disease outcome. The models and/or algorithms can be provided in machine readable format and can optionally further designate a treatment modality for a patient or class of patients.

The device also comprises output means for outputting the disease status, prognosis and/or a treatment modality. Such output means can take any form which transmits the results to a patient and/or a healthcare provider, and may include a monitor, a printed format, or both. The device may use a computer system for performing one or more of the steps provided.

The methods disclosed herein may also comprise the transmission of data/information. For example, data/information derived from the detection and/or quantification of the target may be transmitted to another device and/or instrument. In some instances, the information obtained from an algorithm may also be transmitted to another device and/or instrument. Transmission of the data/information may comprise the transfer of data/information from a first source to a second source. The first and second sources may be in the same approximate location (e.g., within the same room, building, block, campus). Alternatively, first and second sources may be in multiple locations (e.g., multiple cities, states, countries, continents, etc.).

Transmission of the data/information may comprise digital transmission or analog transmission. Digital transmission may comprise the physical transfer of data (a digital bit stream) over a point-to-point or point-to-multipoint communication channel. Examples of such channels are copper wires, optical fibers, wireless communication channels, and storage media. The data may be represented as an electromagnetic signal, such as an electrical voltage, radiowave, microwave, or infrared signal.

Analog transmission may comprise the transfer of a continuously varying analog signal. The messages can either be represented by a sequence of pulses by means of a line code (baseband transmission), or by a limited set of continuously varying wave forms (passband transmission), using a digital modulation method. The passband modulation and corresponding demodulation (also known as detection) can be carried out by modern equipment. According to the most common definition of digital signal, both baseband and passband signals representing bit-streams are considered as digital transmission, while an alternative definition only considers the baseband signal as digital, and passband transmission of digital data as a form of digital-to-analog conversion.

Samples for use with the compositions and kits and in the methods of the present disclosure comprise nucleic acids suitable for providing RNA expression information. In principle, the biological sample from which the expressed RNA is obtained and analyzed for target molecule expression can be any material suspected of comprising cancer tissue or cells. The sample can be a biological sample used directly in a method of the disclosure. Alternatively, the sample can be a sample prepared from a biological sample.

In one embodiment, the sample or portion of the sample comprising or suspected of comprising cancer tissue or cells can be any source of biological material, including cells, tissue, secretions, or fluid, including bodily fluids. Non-limiting examples of the source of the sample include an aspirate, a needle biopsy, a cytology pellet, a bulk tissue preparation or a section thereof obtained for example by surgery or autopsy, lymph fluid, blood, plasma, serum, tumors, and organs. Alternatively, or additionally, the source of the sample can be urine, bile, excrement, sweat, tears, vaginal fluids, spinal fluid, and stool. In some instances, the sources of the sample are secretions. In some instances, the secretions are exosomes.

The samples may be archival samples, having a known and documented medical outcome, or may be samples from current patients whose ultimate medical outcome is not yet known.

In some embodiments, the sample may be dissected prior to molecular analysis. The sample may be prepared via macrodissection of a bulk tumor specimen or portion thereof, or may be treated via microdissection, for example via Laser Capture Microdissection (LCM).

The sample may initially be provided in a variety of states, as fresh tissue, fresh frozen tissue, fine needle aspirates, and may be fixed or unfixed. Frequently, medical laboratories routinely prepare medical samples in a fixed state, which facilitates tissue storage. A variety of fixatives can be used to fix tissue to stabilize the morphology of cells, and may be used alone or in combination with other agents. Exemplary fixatives include crosslinking agents, alcohols, acetone, Bouin's solution, Zenker solution, Helv solution, osmic acid solution and Carnoy solution.

Crosslinking fixatives can comprise any agent suitable for forming two or more covalent bonds, for example, an aldehyde. Sources of aldehydes typically used for fixation include formaldehyde, paraformaldehyde, glutaraldehyde or formalin. Preferably, the crosslinking agent comprises formaldehyde, which may be included in its native form or in the form of paraformaldehyde or formalin. One of skill in the art would appreciate that for samples in which crosslinking fixatives have been used special preparatory steps may be necessary including for example heating steps and proteinase-k digestion.

One or more alcohols may be used to fix tissue, alone or in combination with other fixatives. Exemplary alcohols used for fixation include methanol, ethanol and isopropanol.

Formalin fixation is frequently used in medical laboratories. Formalin comprises both an alcohol, typically methanol, and formaldehyde, both of which can act to fix a biological sample.

Whether fixed or unfixed, the biological sample may optionally be embedded in an embedding medium. Exemplary embedding media used in histology including paraffin, Tissue-Tek® V.I.P.™, Paramat, Paramat Extra, Paraplast, Paraplast X-tra, Paraplast Plus, Peel Away Paraffin Embedding Wax, Polyester Wax, Carbowax Polyethylene Glycol, Polyfin™, Tissue Freezing Medium TFMFM, Cryo-Gef™, and OCT Compound (Electron Microscopy Sciences, Hatfield, PA). Prior to molecular analysis, the embedding material may be removed via any suitable techniques, as known in the art. For example, where the sample is embedded in wax, the embedding material may be removed by extraction with organic solvent(s), for example xylenes. Kits are commercially available for removing embedding media from tissues. Samples or sections thereof may be subjected to further processing steps as needed, for example serial hydration or dehydration steps.

In some embodiments, the sample is a fixed, wax-embedded biological sample. Frequently, samples from medical laboratories are provided as fixed, wax-embedded samples, most commonly as formalin-fixed, paraffin embedded (FFPE) tissues.

II. Prognosis and Treatment

The methods, compositions, and kits disclosed herein may be used for the prognosis, predication, monitoring and/or treatment of cancer (e.g., BLBC) in a subject. In some embodiments, the predicting, and/or monitoring the status or outcome of a cancer includes assessing the risk of cancer recurrence. In some embodiments, predicting, and/or monitoring the status or outcome of a cancer may comprise determining the efficacy of treatment.

In some embodiments, predicting, and/or monitoring the status or outcome of a cancer may comprise determining a therapeutic regimen. Determining a therapeutic regimen may comprise administering an anti-cancer therapeutic. Alternatively, determining the treatment for the cancer may comprise modifying a therapeutic regimen. Modifying a therapeutic regimen may comprise increasing, decreasing, or terminating a therapeutic regimen.

For example, in some embodiments, the methods described herein are used to identify subjects with a high risk of recurrence of breast cancer. Such subjects are offered adjuvant and/or neoadjuvant chemotherapy. In some embodiments, the adjuvant chemotherapy is a platinum-based chemotherapy (e.g., carboplatin or cisplatin) and/or immune checkpoint therapy. Specific agents for adjuvant chemotherapy are described below.

Conversely, in some embodiments, subjects identified as having a low risk of recurrence based on the levels of expression of the described markers are given the option to avoid adjuvant chemotherapy.

In some embodiments, the level of expression of two or more (e.g., 2, 3, 4, 5, 6, 7, 8, 9, 10, 11, or all) of MKRN2, FKBP5, NCR1, SLAMF6, DNAJC1, TMEM30A, CLEC4E, PCYT1A, MREG, HAVCR1, IKZF3, and AIM2 is used to identify subjects for treatment with immune checkpoint therapy.

Examples of anti-cancer therapies include targeting cancer therapy (e.g., targeting the cancer markers described herein), surgery, chemotherapy, radiation therapy, immuno-therapy/biological therapy, and photodynamic therapy.

Chemotherapeutic agents may also be used for the treatment of cancer. Examples of chemotherapeutic agents include alkylating agents, anti-metabolites, plant alkaloids and terpenoids, vinca alkaloids, podophyllotoxin, taxanes, topoisomerase inhibitors, and cytotoxic antibiotics. Cisplatin, carboplatin, and oxaliplatin are examples of alkylating agents. Other alkylating agents include mechlorethamine, cyclophosphamide, chlorambucil, ifosfamide. Alkylating agents may impair cell function by forming covalent bonds with the amino, carboxyl, sulfhydryl, and phosphate groups in biologically important molecules. Alternatively, alkylating agents may chemically modify a cell's DNA.

Biological therapy (sometimes called immunotherapy, biotherapy, or biological response modifier (BRM) therapy) uses the body's immune system, either directly or indirectly, to fight cancer or to lessen the side effects that may be caused by some cancer treatments. Biological therapies include interferons, interleukins, colony-stimulating factors, monoclonal antibodies, vaccines, gene therapy, and nonspecific immunomodulating agents.

In some embodiments, the biological therapy is immune checkpoint therapy. Immune checkpoint inhibitors target CTLA-4, PD-1, or PD-L1. Examples include but are not limited to, ipilimumab, nivolumab, pembrolizumab, spartalizumab, and atezolizumab.

EXPERIMENTAL

The following examples are provided in order to demonstrate and further illustrate certain preferred embodiments and aspects of the present disclosure and are not to be construed as limiting the scope thereof.

Example 1

Methods
Overall Study Design

To discover and validate a novel prognostic signature specific for BLBC, a discovery cohort and five validation cohorts were used. The Seattle breast cancer cohort was used as the discovery cohort because it is highly annotated and includes manually curated medical record data, so detailed information on breast cancer recurrences and all primary treatments could be ascertained. Details of this cohort have been previously published (30). Briefly, all participants in this study were identified through the Cancer Surveillance System (CSS), which is the NCI-funded population-based Surveillance, Epidemiology, and End Results (SEER) cancer registry serving western Washington state. All study procedures were reviewed and approved by the Fred Hutchinson Cancer Research Center's institutional review board (IRB), and informed consent was obtained from all alive participants. Eligible deceased patients were enrolled through an IRB-approved waiver of consent. Thus, survival bias was reduced in the study as tumor tissue samples were collected and medical records were reviewed for these deceased patients. Data on recurrence status, breast cancer treatments, demographics, lifestyle characteristics, medical history, anthropometric measurements, and family history of cancer were collected through both patient interviews and medical record reviews. Greater than 98% of patients enrolled consented to allow us to access their tumor tissue samples, and FFPE samples from consenting participants were requested and obtained from the health care providers storing these clinical samples. Based on the sample size selected for the discovery work, a sample size of 134 with balanced design would have ≥99% power to detect biomarkers that have at least 40% sensitivity (AUC=0.70) in their discrimination between patients who developed a recurrence from those who did not, and 94% power to detect biomarkers with at least 30% sensitivity (AUC=0.65). The five validation cohorts were selected because each included sufficient numbers of TNBC patients with reasonable follow-up time, and each had publicly available gene expression data.

Library Preparation and Sequencing

RNA sequencing was performed using standard protocols in a Clinical Laboratory Improvement Amendments (CLIA)-compliant sequencing lab (77,78). In brief, tumor total RNA was isolated using the AllPrep DNA/RNA/miRNA kit (QIAGEN). RNA sequencing was performed by exome-capture transcriptome platform (33). All samples were sequenced on the Illumina HiSeq 2000 or HiSeq 2500 in paired-end mode. The primary base call files were converted into FASTQ sequence files using the bcl2fastq converter tool bcl2fastq-1.8.4 in the CASAVA 1.8 pipeline.

Transcriptomic Data Analysis

Sequence alignment and normalization. Raw sequencing reads were aligned to the GRCh38 reference genome using STAR (79), and overlaps with Gencode v23 (80) annotated protein-coding genes were counted using featureCounts (81) in strand-specific mode. Non-expressed and lowly expressed genes (<5 reads on average) were removed prior to differential expression (DE) analysis. A scaling normalization scheme (TMM) was applied to all samples (82).

Quality control. RNA-seq quality was evaluated by an array of parameters including alignment rate, duplication rate, and number of splice junctions. Samples with multiple parameters falling at the low-quality end were excluded. Samples that passed QC were pooled with TCGA BRCA samples for principal components analysis (PCA). As a library preparation method (capture) that was different from TCGA (polyA) was used, adjustment factors were applied to compensate for the systematic discrepancy of the two libraries (33). PCA was based on the top 500 genes with the largest variance across all samples. PAM50 (69) annotation for TCGA dataset was obtained from (83) and for the samples, and PAM50 was assigned with R package genefu (84). PAM50 was not used to select patients for the study.

Differential analysis. DE analysis was performed with limma (85) on voom-transformed count data (86). The top 200 most significant genes (100 genes each for up- and down-regulation) were selected, and samples were clustered into three groups based on expression of these genes by k-means. Two clusters with high overlap with recurrent and non-recurrent cases were defined as high- and low-risk groups, respectively. As the third cluster (intermediate group) exhibited similar gene expression patterns while having an almost equal chance of recurrence and being disease-free, a second round of DE analysis was applied to high- and low-risk groups only to identify stronger signals of recurrence. Gene set enrichment analyses were implemented with R package fgsea (87) on a collection combining gene sets from MsigDB hallmark pathways (88) and xCell (89). R package ica (90), was used for Independent component analysis (ICA) in order to detect co-expression gene modules.

Immune profiling. Tumor immune infiltration was assessed by multiple computational tools including CIBERSORT (51) and MiXCR (91). CIBERSORT ran with RPKM as input and under "absolute" mode, which returned scores proportional to absolute abundance. By specifying alignment parameters (–p rna-seq), MiXCR took raw mRNA sequences and quantified clonotypes for T- and B-cell receptors.

Model. To identify prognostic phenotypes of recurrence, an ensemble approach was used, selecting genes identified as predictive by multiple classification algorithms and statistical tests. First, genes were pre-filtered (median RPKM>1 and p value<0.1 in differential analysis) and screened by different feature selection algorithms including Chi2-algorithm (92), fast correlation based filter (93), and information gain (92) with R package Biocomb (94). This list of gene candidates was supplemented by significantly predictive genes using non-linear tree-based classification models, random forest (61) and XGBoost (95). Genes nominated by multiple algorithms were included in subsequent ranking. All gene candidates were then ranked by frequency of being selected by the five methods as well as by p value from the recurrent versus non-recurrent comparison. This resulted in a panel of 55 genes that were selected by at least two methods. A stepwise selection strategy was used to determine the optimal size of the gene panel. Specifically, starting from the top gene, gene panels with incremental sizes (adding one gene at a time) were evaluated for their ability to correctly classify recurrent and non-recurrent cases by leave-one-out cross validation with random forest. After 21 genes, adding more genes did not benefit overall classification accuracy; therefore, the top 21 genes were included in the BRAVO-DX panel. Considering that false-negatives in recurrence predictions are particularly unfavorable, a cost-sensitive variant was applied by oversampling to evaluate the performance of BRAVO-DX with R package mlr in addition to unweighted random forest (96).

Validation Datasets

Five external cohorts were used for validation in this study. The first dataset was the BRCA cohort from The Cancer Genome Atlas (TCGA). Raw RNA-seq data were downloaded and processed in the same unbiased way as in-house sequencing data (except in unstranded mode) to obtain RPKM matrix. The second dataset, GEO, consisted of array-based gene expression profiles compiled from different studies (29). The third dataset was from the METABRIC study (3). Raw idat files were read and processed with BeadArray (97); specifically, normalization across samples were performed with the 'neqc' function (limma) and probes were annotated with illuminaHumanv3.db. Low quality probes (labeled "No match" or "Bad" in the annotation database) were eliminated from further analysis. In addition, two relatively small cohorts were also included for validation. Data from (98) was retrieved with the getGEO function of R package GEOquery (99). Raw CEL files of (100) were downloaded from ArrayExpress (www.ebi.ac.uk/arrayexpress/). Details about the validation datasets are listed in Table 9. PAM50 for the TCGA dataset was obtained from (83), and for the other datasets, R package genefu (84) was used to assign PAM50.

Survival Analyses

Validation of selected biomarkers was performed on the BRAVO cohort and external datasets by univariate survival analysis using the Kaplan-Meier method. Only cases of basal-like subtype, defined by the PAM50 gene set, in both external datasets were included. Optimal cutoff estimated by the cutp function from R package survMisc was used to dichotomize patients if not mentioned otherwise; survival curves were generated with R packages survival and survminer. Multivariate analysis was carried out to assess the influence of adding standard clinical variables (age, race, grade, tumor size, lymph node involvement) on recurrence-free survival of the BRAVO cohort, using the Cox proportional hazards models (101).

Validation of Gene Signatures by Customized TaqMan Real-Time PCR Assay

To test the utility of selected biomarkers using a different platform that can be implemented in the clinic, a customized TaqMan real-time PCR assay was performed on a subset of samples (n=12). Total tumor RNA was isolated using the AllPrep DNA/RNA/miRNA kit (QIAGEN), and cDNA was synthesized using SuperScript IV VILO Master Mix with ezDNase Enzyme (Thermo Fisher Scientific). cDNA samples were pre-amplified by the addition of selected targeted TaqMan probes using TaqMan PreAmp Master Mix (Thermo Fisher Scientific). Real-time PCR was performed using TaqMan Fast Advanced Master Mix (Applied Biosystems) on the QuantStudio 6 Pro Real-Time PCR System (Applied Biosystems). The target mRNA expression was quantified using the $\Delta\Delta Ct$ method and normalized to mean $\Delta Ct$ of four housekeeping genes (EIF2B1, CASC3, HIMBS, and POP4). For genes with two probes, only the one with higher correlation with log 2FPKM from RNA-seq (normalized to the same housekeeping genes) across samples was kept. The TaqMan probes used in the study are listed in Table 11. A linear regression model was used to fit normalized log FPKM with normalized Ct values as the predictor, and the predicted log FPKM values were used as testing data in the random forest model trained previously with RNA-seq data from the full sample set.

Results

Characteristics of Discovery and Validation Cohorts

The discovery cohort was selected from a large population-based prospective cohort of the major molecular subtypes of breast cancer conducted in the greater Seattle-Puget Sound metropolitan area. The methods used in this study have been previously published (30). Briefly, cases consisted of women 20-69 years of age first diagnosed with invasive breast cancer between Jun. 1, 2004 and Jun. 30, 2015 and identified through the population-based Surveillance, Epidemiology and End Results (SEER) program that served the 13 counties of western Washington state. Potentially eligible patients for this analysis (n=949) were identified from the 1408 patients with stage I-III TNBC (ER−/PR−/HER2−), and 949 were enrolled into this study (FIG. 1A). Of these 949 women, 248 were clinically diagnosed with a recurrence (local, regional, or distant) after their initial diagnosis and were identified as likely basal-like through positive staining for epidermal growth factor receptor (EGFR) and/or cytokeratin 5/6. Ten of these patients were diagnosed with a recurrence within six months of their breast cancer diagnosis, and these patients were excluded from this study given the potential for these recurrences to have been extensions of disease missed at original diagnosis. This study was designed and powered to include 67 recurrent and 67 recurrence-free BLBC patients; out of the 76 patients with recurrence randomly selected for inclusion (balanced for tumor stage and extent of recurrence), 67 had RNA of sufficient quality extracted and successfully underwent RNA-seq analysis. These 67 patients were somewhat older than the underlying population of 248 patients with eligible recurrences (68% vs. 57%≥50 years of age), but were otherwise similar with respect to race/ethnicity (81% vs. 78% non-Hispanic white), body mass index (64% vs. 60% BMI, ≥25.0 kg/m2), AJCC stage (76% vs. 84% stage II or III), and tumor grade (92% vs. 90% grade III).

Given the cost of the extensive molecular profiling performed, for efficiency purposes, the 67 recurrent patients were matched to 67 recurrence-free patients 1:1 on factors related to recurrence risk, including age, diagnosis year, stage, and treatment (surgery, radiation, and chemotherapy). Controls were also known to be recurrence-free at least through the same interval between the date of diagnosis and the date of recurrence of the case that they were matched to. Recurrence status was determined for all patients through a detailed, structured medical record review; both local and distant recurrences were included. Data on additional patient demographic characteristics, clinical factors, and established breast cancer risk factors were also collected through both medical record reviews and patient interviews. Patients who received neoadjuvant chemotherapy were excluded because of the impact neoadjuvant therapy has on tumor gene expression from tissue collected post-chemotherapy. Given that recurrent and non-recurrent cases were matched on age, diagnosis year, stage, and treatment, the distributions of these variables were similar between the two groups. Of note, 97% of patients in both groups received adjuvant chemotherapy and 57% received a total mastectomy. Publicly available expression data from five independent cohorts of TNBC patients were used for validation.

Figure 7:
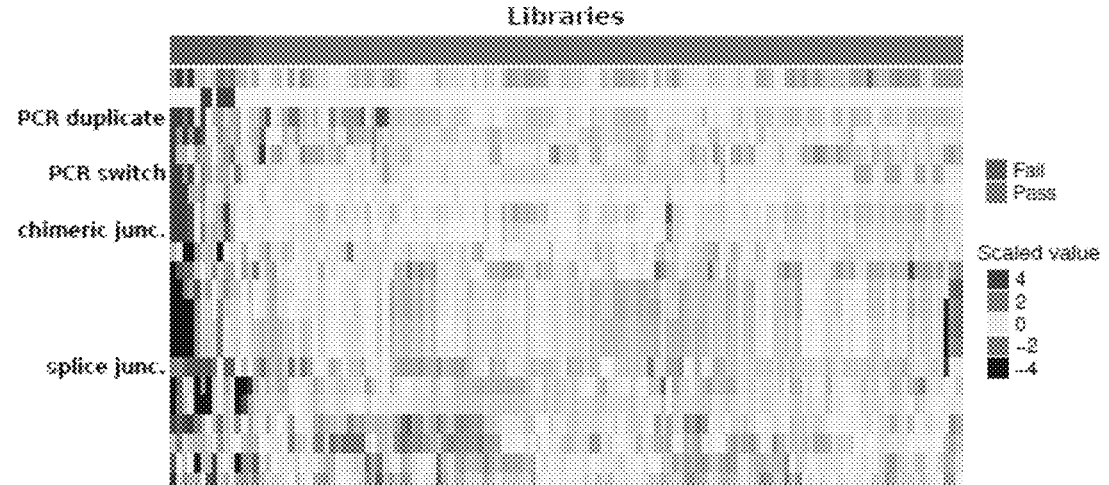
FIG. 7: RNA-seq quality control and assessment of confounding technical parameters. A) Unsupervised clustering of RNA-seq libraries (columns) based on an array of data-driven quality control measures computed from the raw and aligned sequencing data (Methods). B) Estimated admixture of stromal cells within the tumor tissue based on the expression of signature stromal genes from Yoshihara et. al. C) RNA-seq based expression of MKI67 (Ki67), a proliferation marker.
Figure 7:
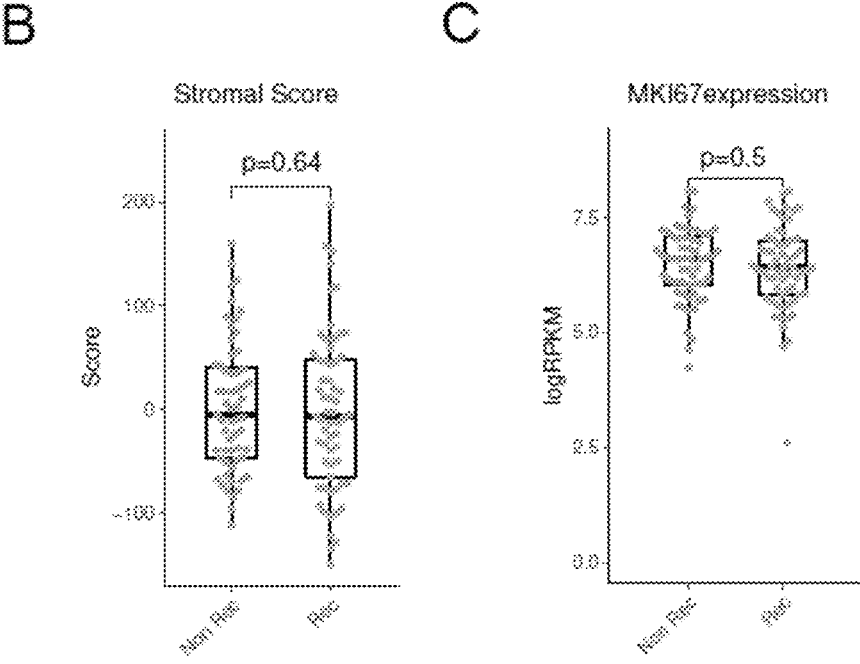

Transcriptomic Profiling of Formalin-Fixed Paraffin-Embedded Tissues in the Discovery Set Pre-treatment formalin-fixed paraffin-embedded (FFPE) blocks of breast cancer tissue collected at the time of primary cancer-directed surgery (lumpectomy or total mastectomy) or diagnosis (core biopsy) were obtained from the hospitals where patients were treated. RNA was successfully extracted from the 134 patients included in this study and used to characterize the molecular and phenotypic characteristics of recurrent and non-recurrent basal breast tumors. Transcriptome profiling of FFPE specimens can be hindered by technical difficulties arising from RNA degradation (31) and cross-linking (32). A hybrid cDNA exome-capture method followed by high-throughput sequencing as an RNA sequencing protocol with improved robustness to RNA degradation and sample fixation was used (33). Therefore, "capture RNA-seq" was performed on all samples in this study. Still, the integrity of RNA extracted from specimens subjected to fixation and long-term storage is expected to be highly variable. In order to identify samples of particularly low quality, a data-driven strategy was used. First, a battery of RNA-seq quality-control (QC) measures, including variables correlating with input RNA quality, library complexity, and in vitro generated molecular artifacts was used (see Methods). Next, the RNA-seq libraries were clustered based on all of these computed QC measures (FIG. 7A). This unsupervised analysis revealed that while no single QC parameter was sufficient to reliably indicate RNA-seq quality, the joint interrogation of multiple QC parameters identified a set of samples with poor or marginal reads for many of them. These samples (n=14) were excluded from all of the following analyses. Next, to verify the accuracy and concordance of the transcriptomic platform, it was tested whether the retained samples recapitulated intrinsic breast cancer gene expression profiles (GEPs). Samples were compared to the TCGA breast cancer cohort comprising basal-like, luminal, HER2-amplified, and normal-like tumors profiled using poly(A)+ RNA-seq (FIG. 1B). IT was found that basal-like cancers from the cohort clustered together with the basal-like TCGA cancers, and 90.8% of the tumors classified as the PAM50 basal-like intrinsic subtype (34,35) (see Methods). Next, it was verified that recurrence status was not confounded by technical covariates. RNA and sequencing library quality, as measured by the number of detected splice junctions (FIG. 7A), did not associate with recurrence. Functional expression signatures can be confounded by tumor purity (36), which can be either caused by biased specimen selection criteria or true underlying biological differences. Computational deconvolution allows for the estimation of non-cancer admixtures from transcriptome data (37). Accordingly, critical parameters such as tumor purity (FIG. 1C) (38) or stromal admixture (FIG. 7B) were estimated (39) and confirmed that these were not significantly associated with recurrence. In addition, neither group of samples showed substantially elevated levels of ER (ESR1), PR (PGR), or HER2 (ERBB2) (FIG. 1D). Importantly, recurrence was not predicted by cell proliferation, as determined by immunohistochemistry and expression profiling (FIG. 7C), motivating more in-depth analyses.

Association of Tumor Molecular Characteristics with Recurrence

Figure 2:
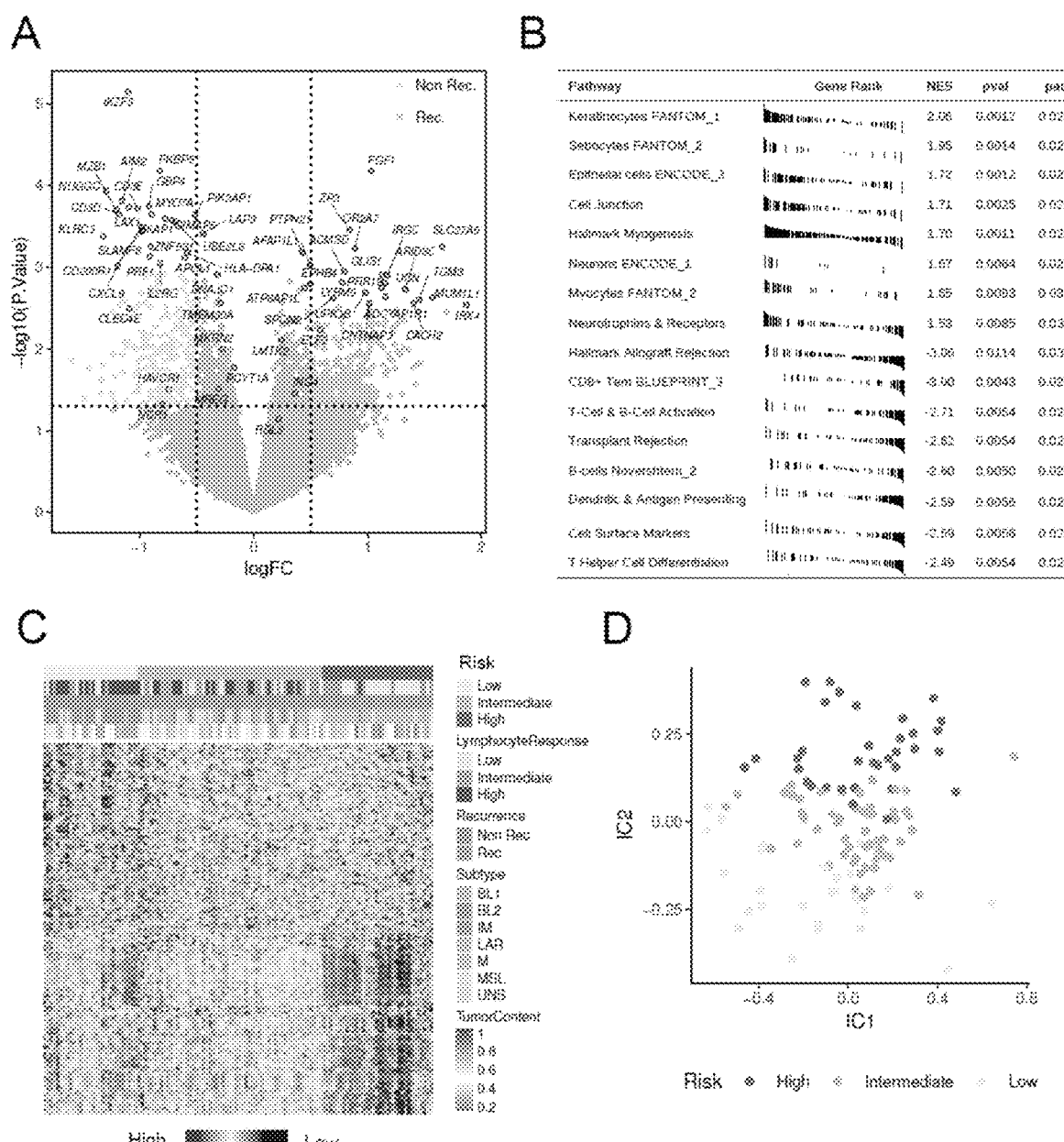
FIG. 2: Transcriptional characteristics of recurrent and non-recurrent BLBC tumors. A) Volcano plot of differentially expressed genes between recurrent and non-recurrent BLBC samples. B) Gene set enrichment analysis of molecular signatures from the top up- and down-regulated significant (padj<0.05) signatures based on the normalized enrichment score (NES) are plotted. In the barcode-plots, genes are plotted left-right from highest to lowest log-fold change. C) Supervised clustering of BLBC tumors based on the expression of genes most significantly associated with recurrence. D) Unsupervised Independent Component Analysis of variably expressed genes across BLBC.
Figure 8:
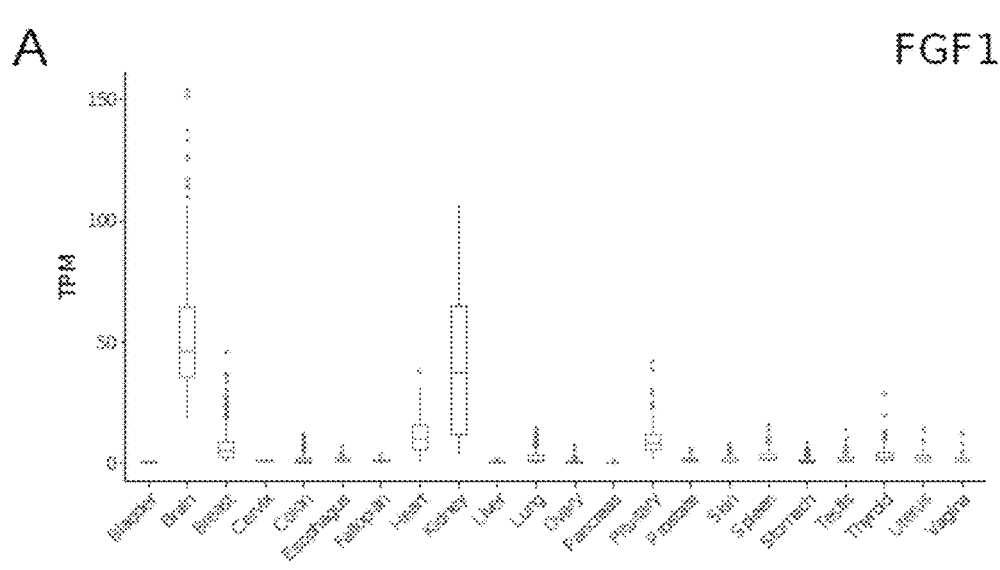
FIG. 8: Expression of FGF1 and SLC27A6 across normal human tissues. A) Expression of FGF1 across the GTEx compendium. B) Expression of SLC27A6 across the GTEx compendium. TPM—transcripts per million. C) Expression of SLC27A6 and MYC in the BRAVO cohort.
Figure 8:
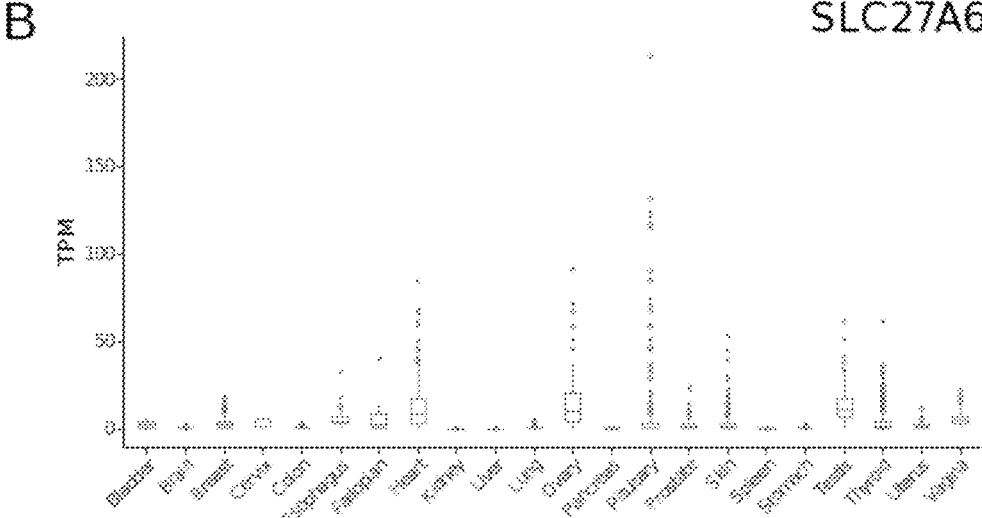
Figure 8:
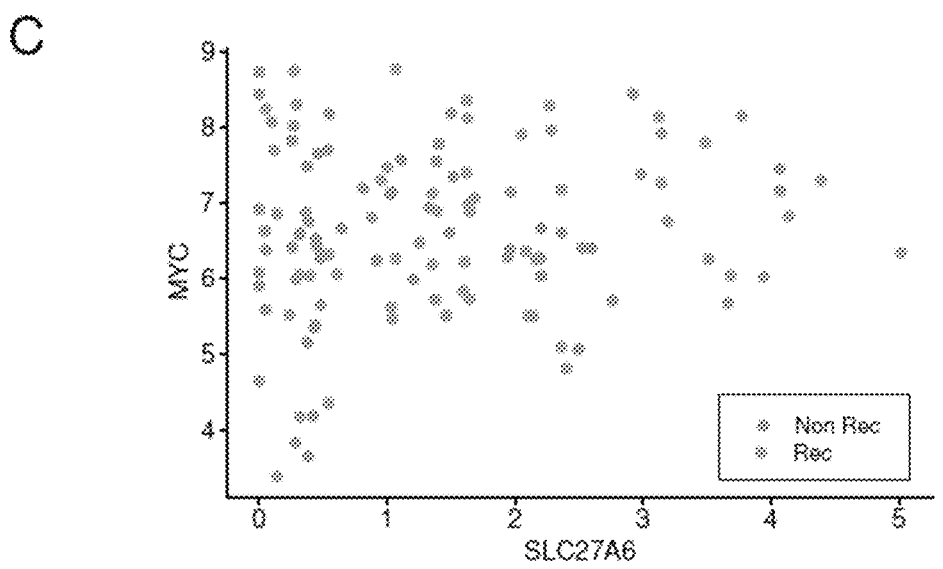

To elucidate the molecular underpinnings of disease recurrence, differential expression (DE) analysis followed by functional analyses of the significant DE genes was performed (FIG. 2). First, in a supervised approach, recurrent vs. non-recurrent tumors were compared (FIG. 2A) and found 560 nominally differentially expressed genes (Table 1) (p<0.05, absolute log(fold-change)>0.5). Overall, similar numbers of genes associated with good prognosis (survival-genes, n=239) and poor prognosis (risk-genes, n=321) were identified. However, slightly more survival-genes than risk-genes (118 vs. 79) met more stringent statistical thresholds (p<0.01). The presence of a large number of genes with moderate effect sizes recommends the development of a compound risk signature. Among the most significant risk-genes were FGF1 and SLC27A6, which highlight multiple cellular origins of transcripts. Notably, both genes have a highly restricted expression profile (FIG. 8A,B). SLC27A6 is a long-chain fatty acid transporter expressed in mammary epithelial cells. Fatty acid uptake from the surrounding adipose-rich breast tissue is critical for TNBC, which rely on fatty acid oxidation as a source of energy (40). The dependence on SLC27A6 has been previously linked to MYC overexpression, however SLC27A6 remains an independent prognostic factor as it is uncorrelated with MYC expression (FIG. 8C). FGF1 is a universal ligand for fibroblast growth factor receptors (FGFRs) and a strong proangiogenic factor (41). Paracrine and autocrine FGFR signaling is also a targetable axis (42) in TNBC due to recurrent genetic aberrations in FGFRs (43-45). Among the most significant survival-genes were IKZF3 (Aiolos) and FKBP5, whose expressions are typically restricted to leukocytes (46) and adipocytes (47), respectively. These and several other examples in Table 1 led to a hypothesis that risk-genes are expressed by cancer cells, while survival-genes arise from constitutive (e.g., adipocytes) or infiltrating (e.g., leukocytes) cells in the breast tumor microenvironment. Gene set enrichment analysis supported this observation (FIG. 2B). Risk-genes were significantly enriched in epithelial markers (NES=1.72, p=0.0012) and their junctions (NES=1.71, p=0.0025) among several cellular differentiation signatures, including keratinocytes, sebocytes, and myogenesis. Survival-genes were strikingly enriched for immune cell markers and immune-related signatures such as lymphocyte activation (NES=−2.71, p=0.0054).

Figure 9:
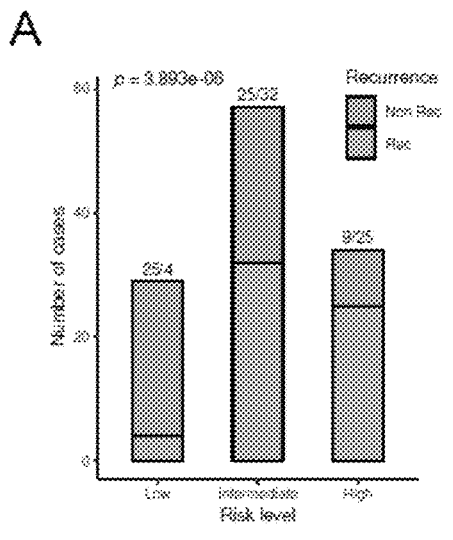
FIG. 9: Differential expression analysis of high-risk vs low-risk BLBC tumors. A) Frequency of recurrence within low/intermediate/high BLBC risk-strata. B) Differential expression between high-risk and low-risk BLBC tumors. C) Gene set enrichment analysis of molecular signatures from genes associated with recurrence risk. D) Functional enrichments for genes associated with positive and negative loadings on independent component 2 (IC2). E) Boxplot of IC2 levels across the three BLBC risk-strata.
Figure 9:
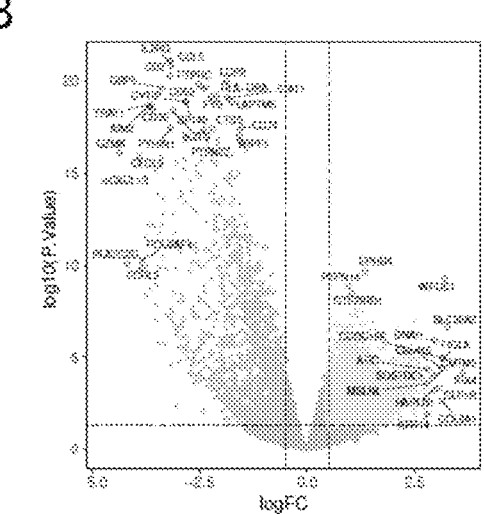
Figure 9:
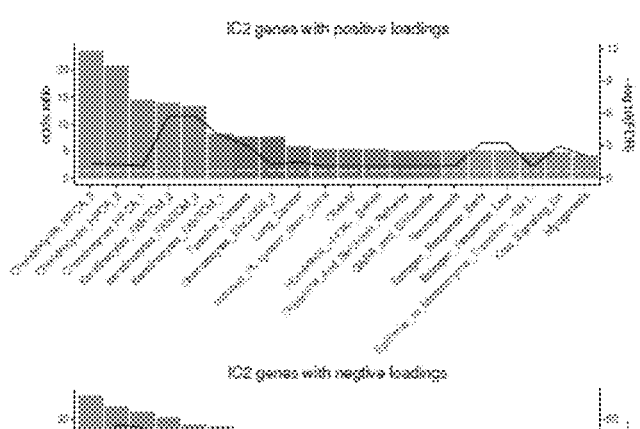
Figure 9:
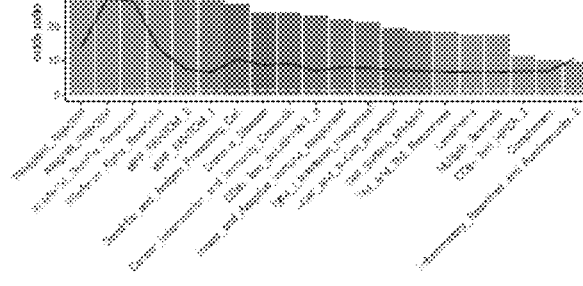

Since BLBC is a heterogeneous disease, it was assessed whether recurrence was associated with distinct molecular or histochemical subtypes. A balanced set of the top differential 100 risk-genes and 100 survival-genes was used to cluster patients based on their expression levels (Table 1, FIG. 2C). This unsupervised clustering guided by risk-associated genes revealed three well-defined reproducible clusters, each accounting for 24%/48%/28% of cases, respectively. Strikingly, recurrence risk varied considerably between those strata, which was termed low-/intermediate-/high-risk (p=3.9e-6, Fisher's test, two-sided), and ranged between 14% and 74% (FIG. 9A). The low-risk stratum had high lymphocyte infiltration, as assessed by pathologic review (odds-ratio=6.50, p=4.0e-5 by Fisher's test), resulting in lower total tumor content, and showed enrichment for two proposed immunological subtypes of TNBC, IM (immunomodulatory) and M (mesenchymal) (odds-ratio=21.80, p=1.1e-9), associated with good outcomes (48,49). Conversely, the high-risk stratum had low immune infiltration (odds-ratio=6.43, p=2.0e-5) and displayed mesenchymal features (odds-ratio=61.9, p=2.3e-15). When contrasted, high- and low-risk groups showed pronounced significant expression differences (FIG. 9B). The high-risk stratum was enriched for stem-like, mesenchymal signatures, and growth factor signaling, while the low-risk stratum was predictably dominated by immune-related expression (FIG. 9C). In a parallel unsupervised analysis, independent components (IC) that explain a large proportion of expression variability across patients were identified (50). IT was found that the first two components were significantly associated with recurrence risk (see Methods) (FIG. 2D). The second IC subsumed immunological (negative loading) and mesenchymal (positive loading) gene sets (FIG. 9D) and was associated with prognosis (FIG. 9E). Together, these data indicate that recurrence risk in BLBC is significantly correlated with transcriptomic phenotypes that integrate cancer-cell intrinsic and immune-cell extrinsic expression patterns.

Immunogenomic Correlates of Recurrence-Free Survival

Figure 3:
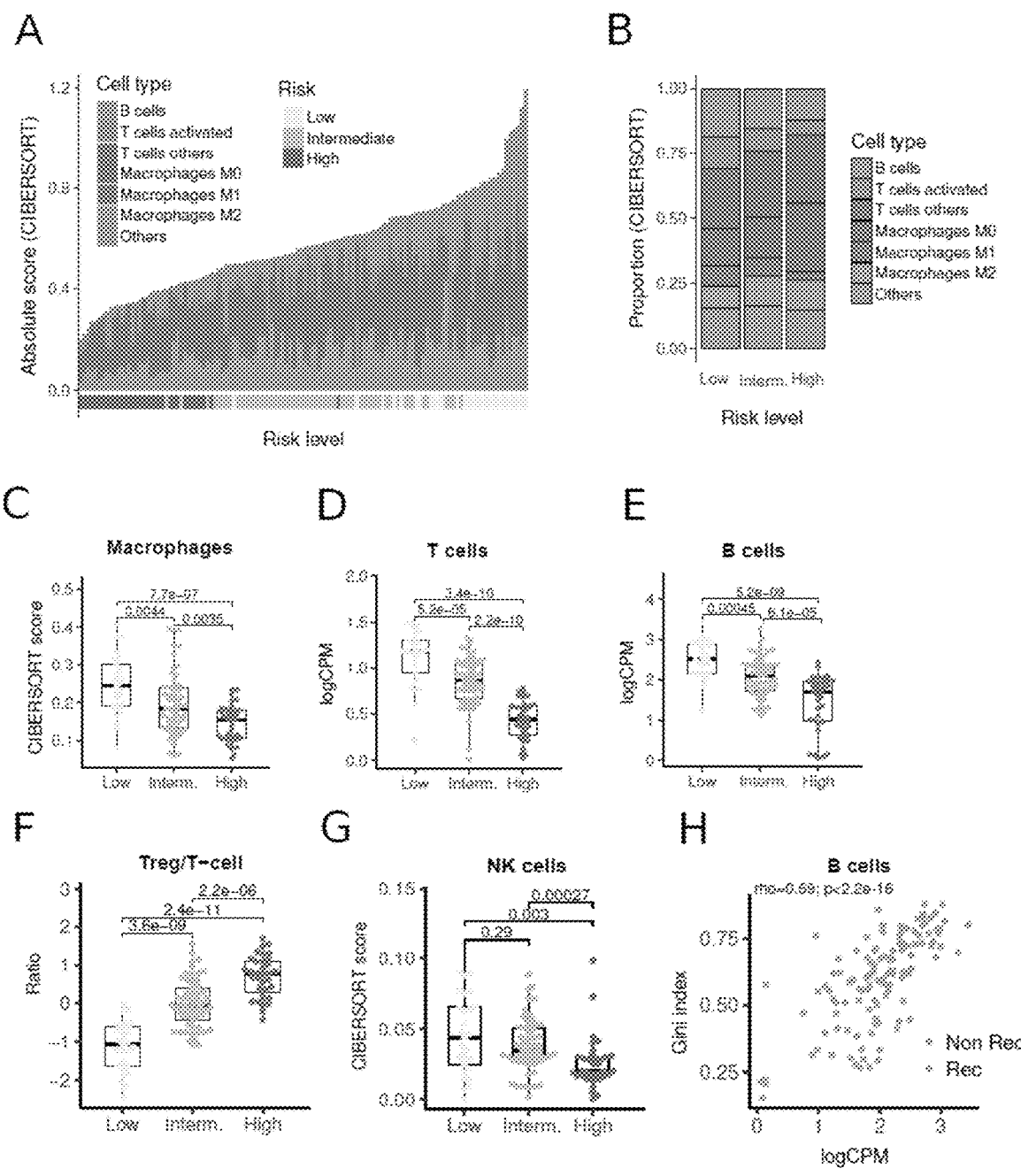
FIG. 3: Immunogenomic correlates of BLBC recurrence risk. A,B) Tumor infiltration by immune cells is associated with a significant reduction in recurrence risk. A) Recurrence risk is highly correlated with magnitude of immune infiltration (CIBERSORT score). B) Differences in immune cell-type composition between low/intermediate/high-risk groups of BLBC. C-G) Association of immune cell subsets with disease recurrence. C) Macrophages and D) T-cells are based on CDR3 sequence abundance; E) B-cells are based on CDR3 sequence abundance. F) Expression ratio of Treg to all T-cells based on marker genes (FOXP3 for Treg; CD3 and CD2 for T-cells). G) NK-cell abundance based on marker gene expression. H) Clonal expansion (Gini index) of T-cells and B-cells is associated with a reduced risk of recurrence.
Figure 10:
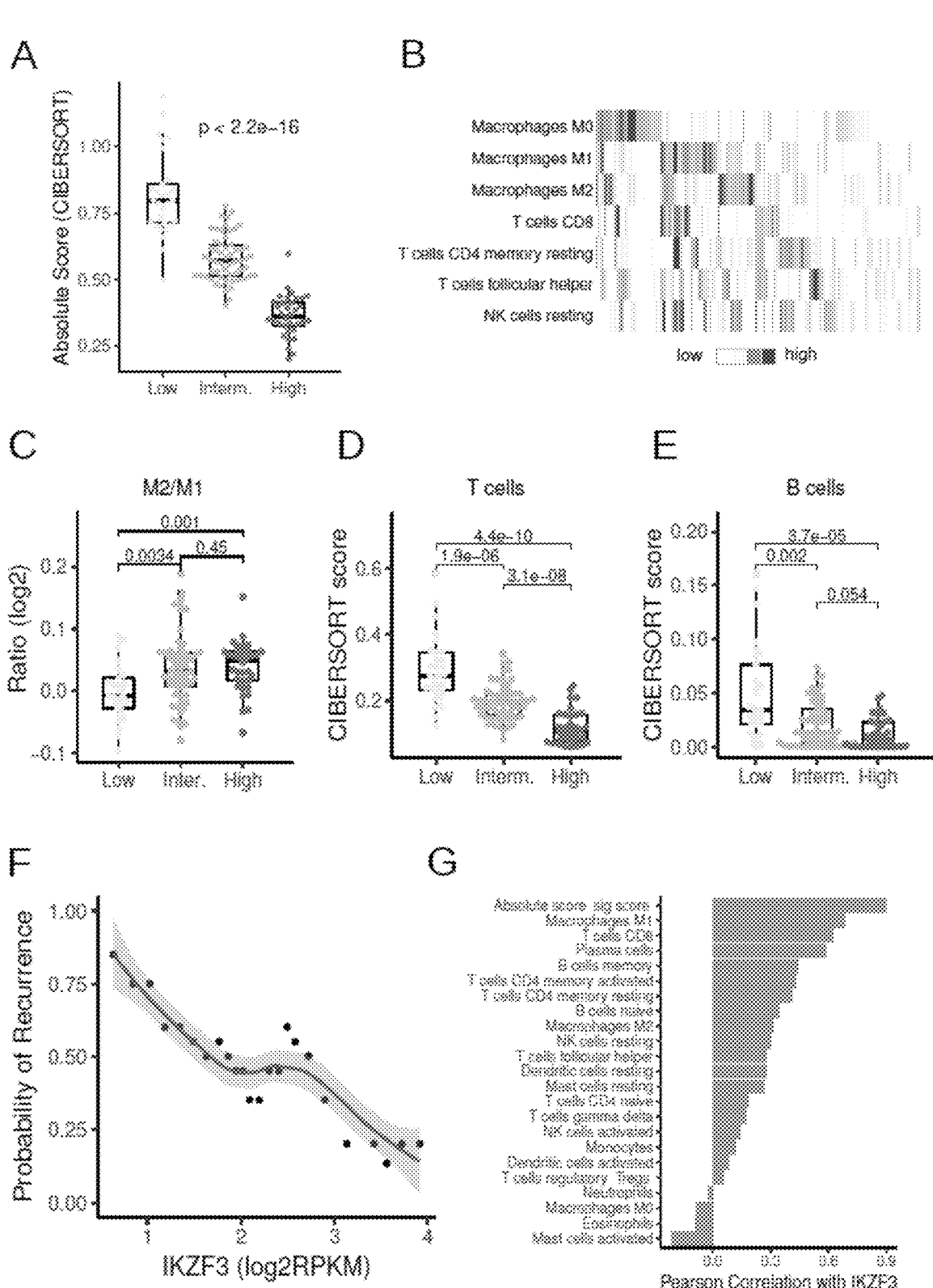
FIG. 10: Additional immunogenomic correlates of BLBC recurrence risk. A) Boxplot of absolute CIBERSORT infiltration scores across BLBC risk groups. B) Association of CIBERSORT-estimated immune cell types with recurrence risk groups. CIBERSORT cell type proportions were averaged across samples within a risk group. C-E) Association of predicted immune cell types with recurrence risk: C) Macrophages, D) T-cells, E) B-cells. F) Probability of recurrence as a function of IKZF3 expression. G) Association (Pearson correlation coefficient) of immune-related pathways with IKZF3 expression levels.

The immunological differences between recurrent and non-recurrent BLBC tumors was investigated in more detail. First, a computational approach, CIBERSORT (51), was used to characterize the tumor microenvironment in terms of magnitude and cellular composition of infiltrating leukocytes, a result later confirmed using T-cell receptor-based profiling. Pronounced immunological heterogeneity was found across the cohort (FIG. 3A, FIG. 10A-E) (49,52). The tumors varied considerably in terms of total levels of immune infiltration as well as compositional characteristics (FIG. 3A,B). Tumors stratified by recurrence risk displayed significant risk group-dependent differences in overall immune infiltration (p<2.2e-16, Kruskal-Wallis test) (FIG. 10A). At the most general level, macrophage polarization (M0/M1/M2) was mutually exclusive across patients (FIG. 10B). High-risk tumors had low macrophage levels and were uncommitted to M0 or polarized towards the immunosuppressive M2 subtype (53,54) (FIG. 3C, FIG. 10C). Conversely, low-risk tumors had a high proportion of pro-inflammatory M1 macrophages and increased estimated levels of tumor-infiltrating T and B lymphocytes (TILs). In addition to the above computational cell-type deconvolution, RNA-seq enables multiple approaches to quantify tumor infiltration by T- and B-cells: marker expression and repertoire assembly (sequencing of the CDR3 complementarity-determining region). Those methods were used to observe risk group-dependent differences in T-cell levels (FIG. 3D), with both methods in agreement (FIG. 10D). An equally significant trend was found for B-cells (FIG. 3E, FIG. 10E) (55). Overall, low-risk tumors showed higher absolute (based on normalized CDR3 numbers) and relative (based on deconvolution) levels of TILs. These increases were mirrored by a lower ratio of regulatory T-cells (Treg) to CD8+ T-cells (fold-change=0.28, p<2.2e-16 by Wilcoxon test, FIG. 3F) and higher abundance of natural killer (NK) cells (fold-change=1.81, p=0.0025 by Wilcoxon test), both indicative of an active anti-tumor immune response in non-recurrent tumors (FIG. 3G).

It was determined whether the observed immune responses are likely tumor-specific. If inflammation is antigen-directed, one would expect expansion of select T- or B-cell clones (56). The Gini index was used as a statistical measure of inequality of the clonotype distribution (57). A significant association between the abundance of TILs and the degree of clonal expansion (lower Gini index) was observed (FIG. 3H), with a particularly strong correlation (rho=0.69; p<2.2e-16) for B-cells. To explore the novel association between B-cell clonal expansion and cancer recurrence, a logistic-regression model was constructed with both T- and B-cell Gini indices as independent covariates (Table 2). Only B-cell clonality remained a significant predictor of recurrence in BLBC (p=0.012). Consistently, among the most significant survival-genes (FIG. 2A), several were markers of B-cells, including IKZF3 (fold-change=2.14, p='7.1e-6), AIM2 (fold-change=2.23, p=0.0016), and SP140 (fold-change=1.56, p=0.0042). Further, expression levels of IKZF3, a key regulator of B-cell activation (46), had a striking expression-dependent association with the likelihood of recurrence (FIG. 10F) and significantly correlated with activated states of T-cells, B-cells, macrophages, and total immune infiltration score (FIG. 10G). Taken together, these data indicate that antigen-directed anti-tumor immune responses are strongly prognostic.

Figure 4:
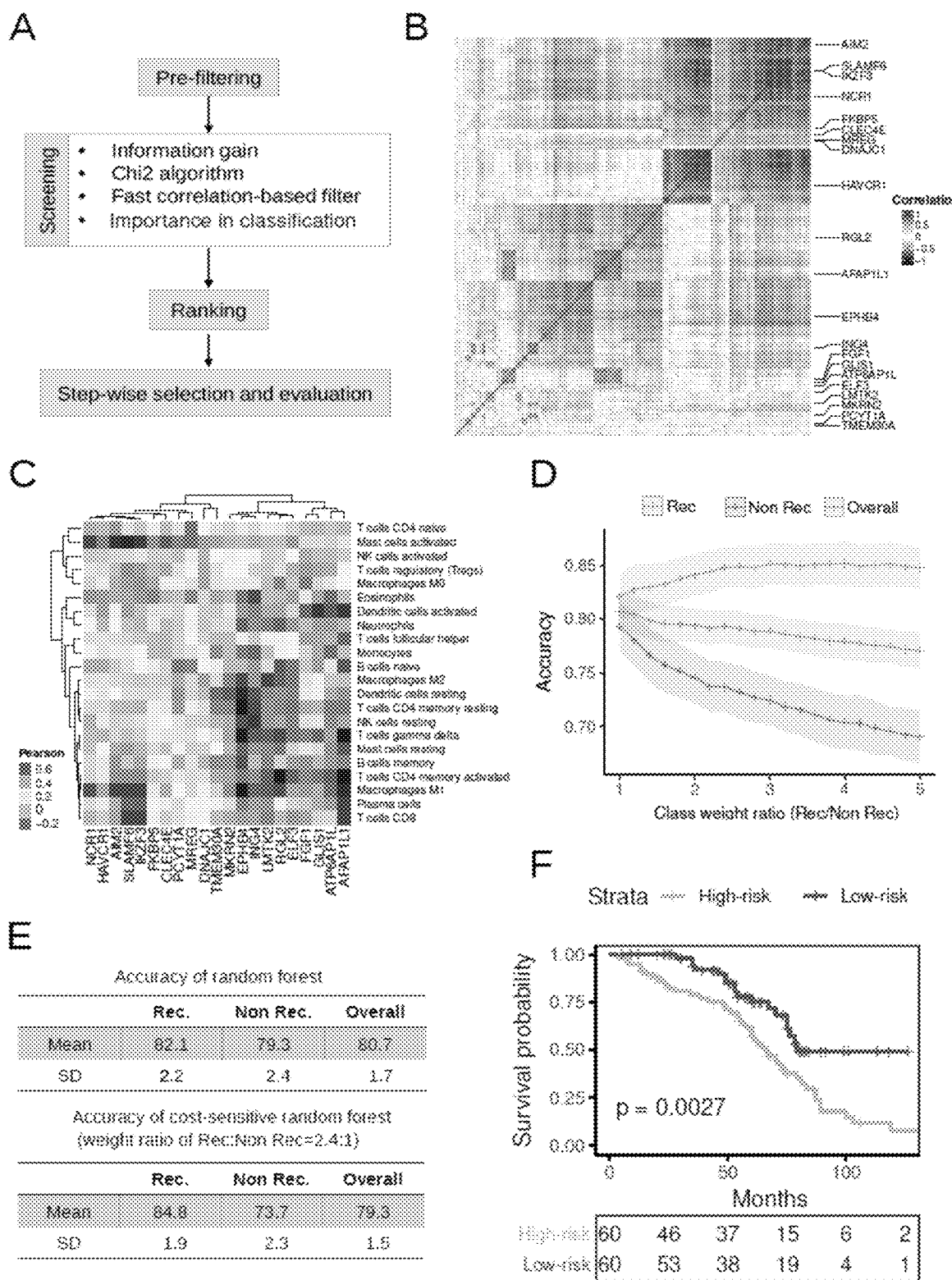
FIG. 4: Development and characterization of a prognostic gene signature. A) Multi-step procedure for the selection of candidate biomarker genes. B) Correlation heatmap for genes differentially expressed between recurrent and non-recurrent BLBC. C) Pearson correlation coefficients of BRAVO-DX marker genes with CIBERSORT estimates of immune cell infiltrates. D) Impact of oversampling recurrent cases during training on average random forest classifier accuracy. E) Accuracy of an unbiased and cost-sensitive random forest classifier trained to predict cancer recurrence based on the expression of BRAVO-DX biomarker genes. F) Kaplan-Meier recurrence-free survival plot dichotomized by BRAVO-DX expression score.
Figure 11:
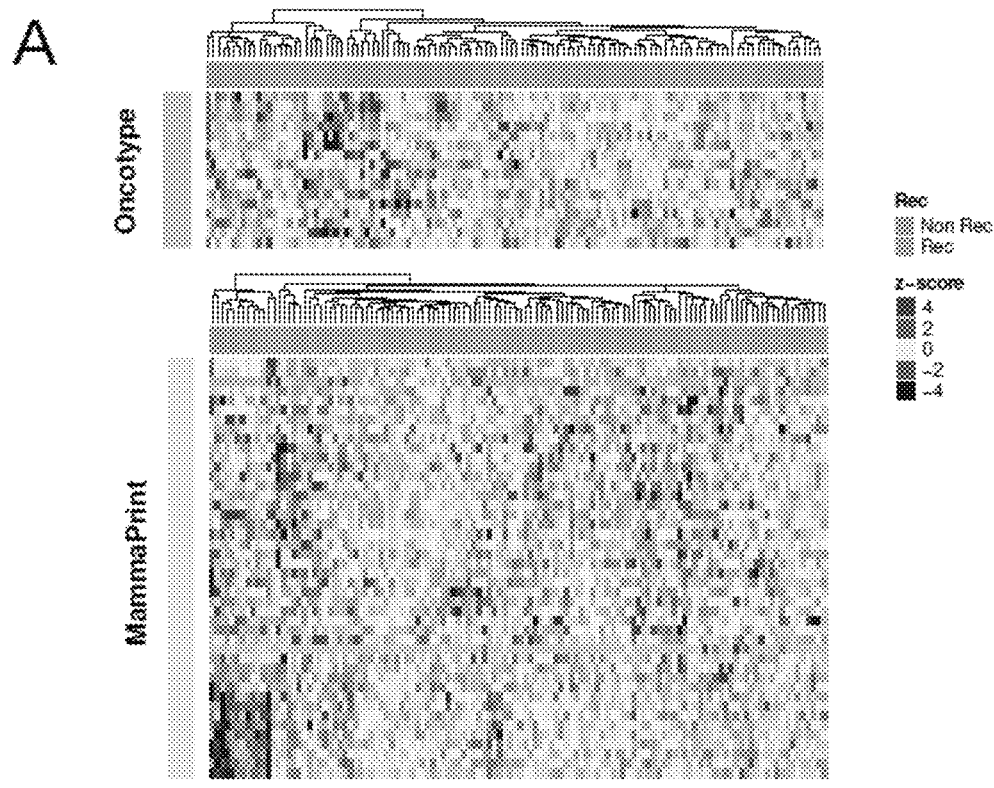
FIG. 11: Patterns of gene expression across the BRAVO cohort. A) Expression of OncoType DX and MammaPrint signature genes in the BRAVO cohort. B) Heatmap representing the correlation between genes associated with recurrence (bottom) and survival (top).
Figure 11:
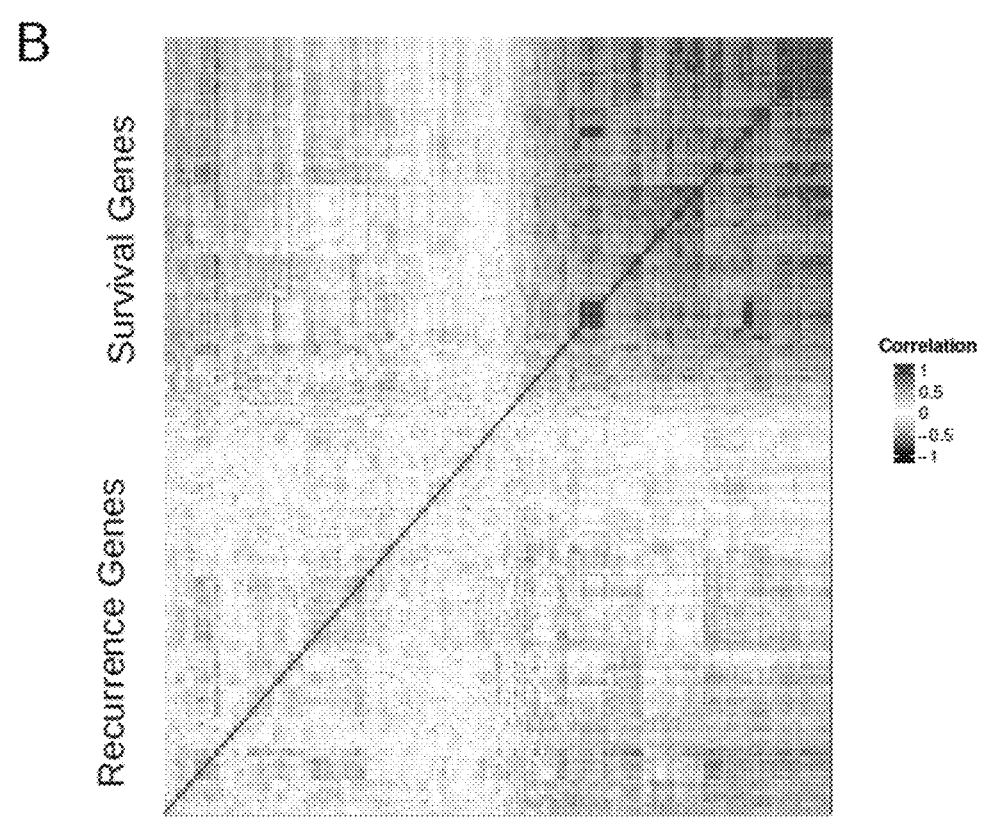

Development and Validation of Robust Models for Recurrence-Free Survival in BLBC and TNBC Given the overall dearth of biomarkers, prognostic stratification remains a challenge in the management of BLBC and TNBC. While expression-based panels, such as MammaPrint (58) and Oncotype DX (59), have transformed clinical decision making for ER+ breast tumors, their performance in TNBC/BLBC is poor. In the BRAVO BLBC cohort, MammaPrint- and Oncotype DX-based classifiers exhibited poor prognostic performance (Table 3), as shown by the lack of differential expression of their constituent genes between recurrent and non-recurrent tumors (FIG. 11A). Further, with the exception of mesenchymal stem-like tumors, existing molecular subtypes of TNBC are only weakly associated with recurrence (FIG. 2C). In cohort described herein, clinical covariates were also unable to independently predict disease recurrence (Table 4). Informed by the pronounced phenotypic and prognostic stratification of BLBC tumors, a robust panel of prognostic genes and an associated classification algorithm to predict cancer recurrence was developed (FIG. 4).

Figure 12:
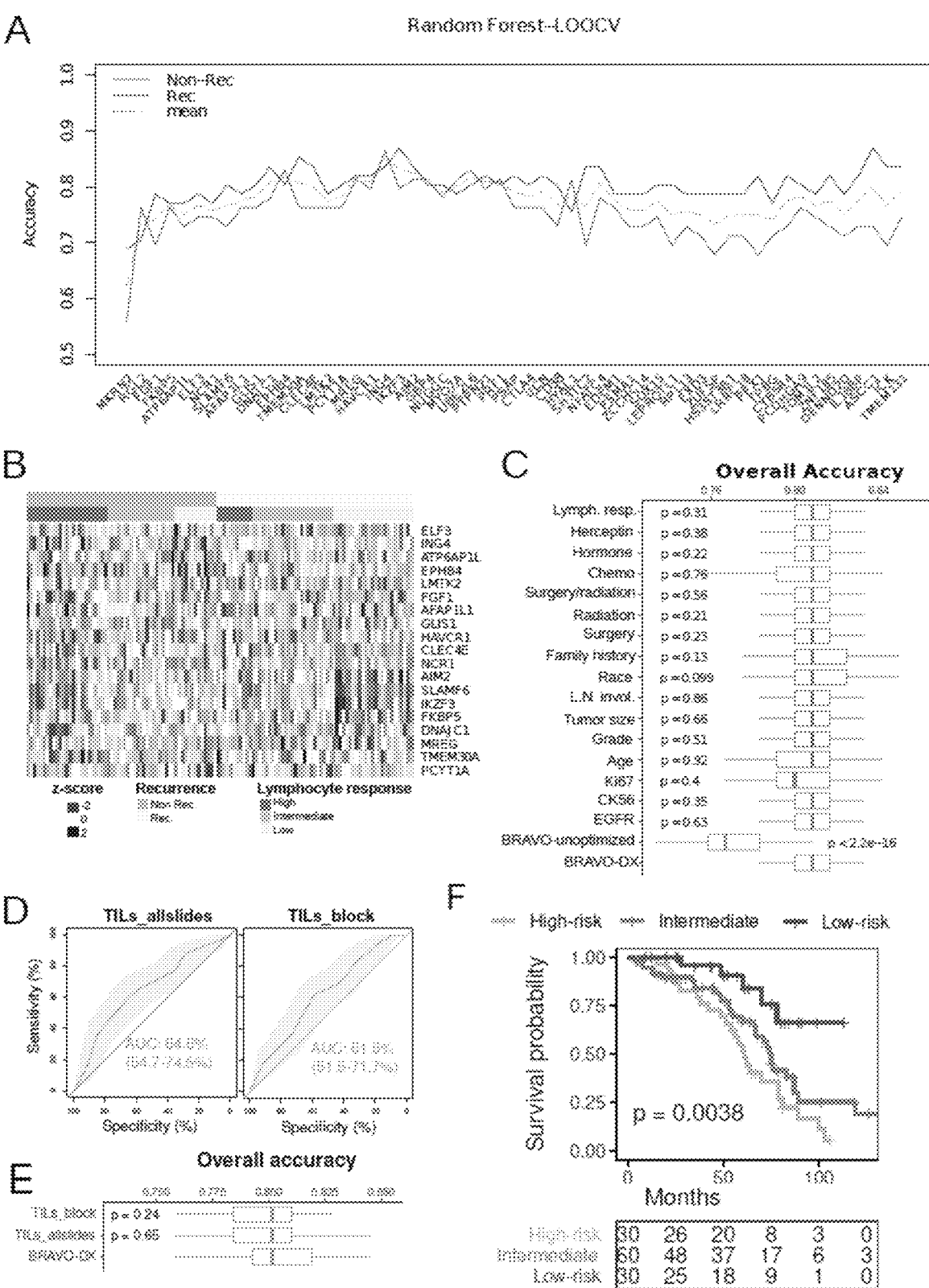
FIG. 12: Optimization of the BRAVO-DX prognostic expression signature. A) Leave-one out cross-validation (LOOCV) of signatures of increasing sizes. B) Heatmap representation of the expression of genes in the BRAVO-DX panel. C) Impact of clinical covariates on the classification accuracy of a random forest model which added each of the clinical variables as well as BRAVO-DX expression levels. D) Receiver operating characteristic (ROC) curves of tumor-infiltrating lymphocytes (TILs) in classifying recurrence and non-recurrence. E) Impact of TILs on the classification accuracy of a random forest model which added TILs. Classification accuracy in C) and D) was estimated by 15-fold cross validation repeated 100 times, and p value was obtained by the Wilcoxon test. F) Kaplan-Meier recurrence-free survival plot stratified into low/medium/high-risk groups based on BRAVO-DX expression score.

The approach took advantage of a balanced cohort design (FIG. 1A) and applied stringent variable selection and cross-validation (CV) (FIG. 4A). First, risk-genes and survival-genes were highly correlated and, hence, of limited utility as independent markers within a prognostic panel (FIG. 11B). To identify non-redundant and uncorrelated marker genes, multiple variable selection algorithms, including information gain (60) and classification importance (61) were used in an ensemble strategy to select a single ranking of most informative features (see Methods). Their application resulted in a ranking of genes based on both their non-redundancy and expected utility in classification (Table 5). To determine a useful panel size, a sequence of random forest (RF) classifiers was trained for increasing the number of genes with leave-one out CV (LOOCV) (FIG. 12A). Average classifier performance started to decline for panels larger than 25 genes, likely due to over-fitting. Therefore, the top-ranked 21 genes were selected as the panel (BRAVO-DX) for further evaluation, as it generalized across different classification algorithms (Table 6). Compared to differentially expressed genes, BRAVO-DX markers were less redundant and were representatives for larger independent sets of genes with correlated expression patterns (FIG. 4B). Notably, BRAVO-DX genes were differentially expressed between recurrent and non-recurrent tumors but did not correlate with histochemical immune responses (FIG. 12B,C). Therefore, to assess whether the panel covered both cancer cell-intrinsic and immune cell-extrinsic expression patterns, the expression of BRAVO-DX genes was correlated with predicted abundances of immune cells (FIG. 4C). Approximately half of the genes showed a negative correlation coefficient with the predicted abundance of immune cells and were not immune cell markers, thus indicating that they were expressed intrinsically by the tumor cells.

Standard classification algorithms optimize classification accuracy by giving equal weight to false-positive and false-negative prediction errors. However, in clinical practice, the sensitivity of picking out cases that are likely to recur (low false-negative) is of utmost importance given the desire to optimize the identification of patients who will develop a recurrence and, thus, have an appreciably elevated risk of death. Therefore, cost-sensitive learning (62,63) was used to train classifiers with the desired classification characteristic (FIG. 4D,E). The baseline RF classifier achieved an overall classification accuracy of 80.7% (15-fold CV) that was balanced in terms of false-positive and false-negative errors. To minimize the number of false-negatives, the ratio of recurrent to non-recurrent cases during training was increased (FIG. 4D). This resulted in a lower number of incorrect negative calls and higher number of false-positives. At the optimal oversampling rate of 2.4, an 84.8% sensitivity in identifying recurrent cases with only a slight decrease in overall accuracy (79.3%) was obtained (FIG. 4E). Importantly, neither sensitivity nor specificity could be further improved by increasing the panel size, incorporating additional clinical covariates (FIG. 12C), including TILs (FIG. 12D,E), or using more sophisticated machine learning algorithms such as xgBoost (Table 7). To confirm the ability of BRAVO-DX to stratify patients, recurrence-free survival (RFS) was evaluated in patient groups defined by BRAVO-DX scores. BRAVO-DX reliably (p=0.0038) identified patient groups with significant differences in RFS when the cohort was split into high/moderate/low-risk groups (FIG. 12F) as well as dichotomized by median (FIG. 4F). A multivariate survival analysis using the Cox model revealed that the prognostic performance of BRAVO-DX score was independent of standard clinical variables as it persisted as a significant predictor with or without inclusion of standard clinical variables in the model (Table 8). In summary, the balanced design and long-term follow-up of the BRAVO cohort allowed for the dichotomization of recurrence status and employment of statistical learning to identify prognostic genes.

To further demonstrate the clinical utility of the 21-gene BRAVO-DX panel, its prognostic performance was tested in independent validation cohorts. Therefore, in addition to the BRAVO-DX 21-gene set, BRAVO-IMMUNE, a subset of BRAVO-DX which comprises the 12-gene set focused on the tumor immune-phenotype was defined (Table 6), along with a minimal subset of BRAVO-DX which included only the three most highly significant risk- and survival-genes (IKZF3, AIM2, and ELF3).

Figure 5:
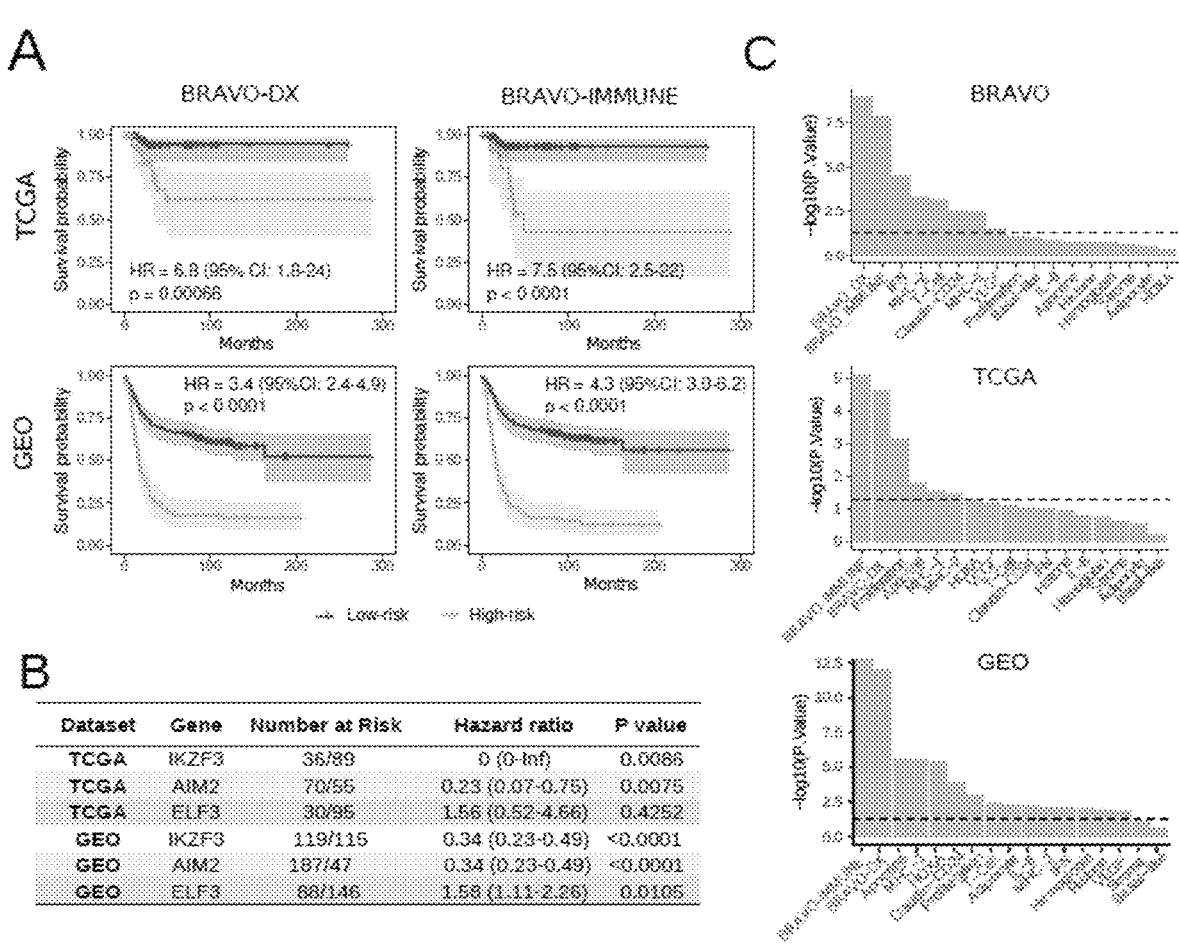
FIG. 5: Validation of the BRAVO-DX gene expression signature. A) Kaplan-Meier plots of survival in the TCGA and Gyorffy (GEO) cohorts. B) Prognostic performance of top intrinsic and immune genes within BRAVO-DX signature. C) Prognostic performance of multiple gene expression signatures in three independent BLBC/TNBC cohorts.
Figure 13:
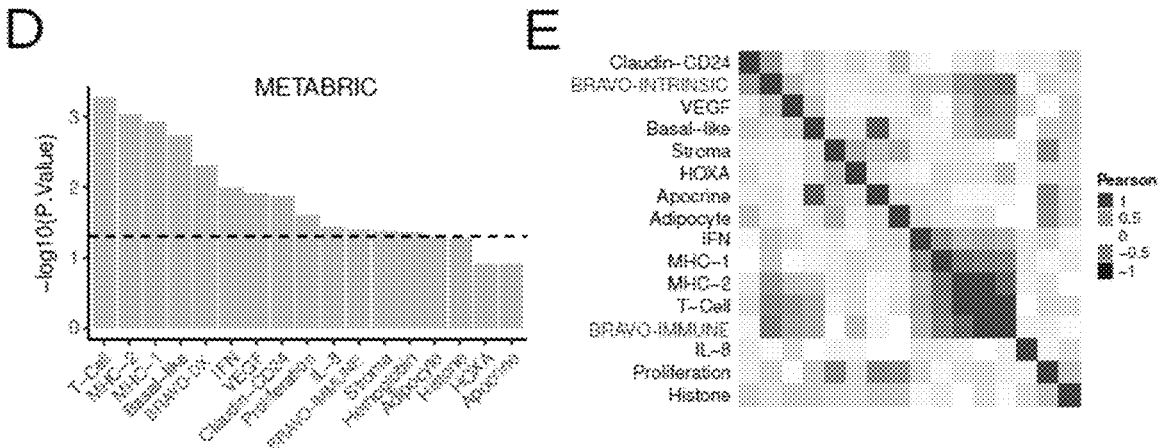
FIG. 13: Independent validation of BRAVO-DX. A) Survival across all TNBC tumors in the METABRIC cohort. B) Same as A) except focused on a subset of patients with the Nottingham Prognostic Index (NPI)<5.4 (favorable prognosis). C) Validation of prognostic utility of three marker genes across the METABRIC cohort. D) Associations with survival of multiple prognostic gene expression signatures across the METABRIC cohort. E) Correlations between summary scores of prognostic gene expression signatures in the BRAVO cohort.
Figures 14, 15:
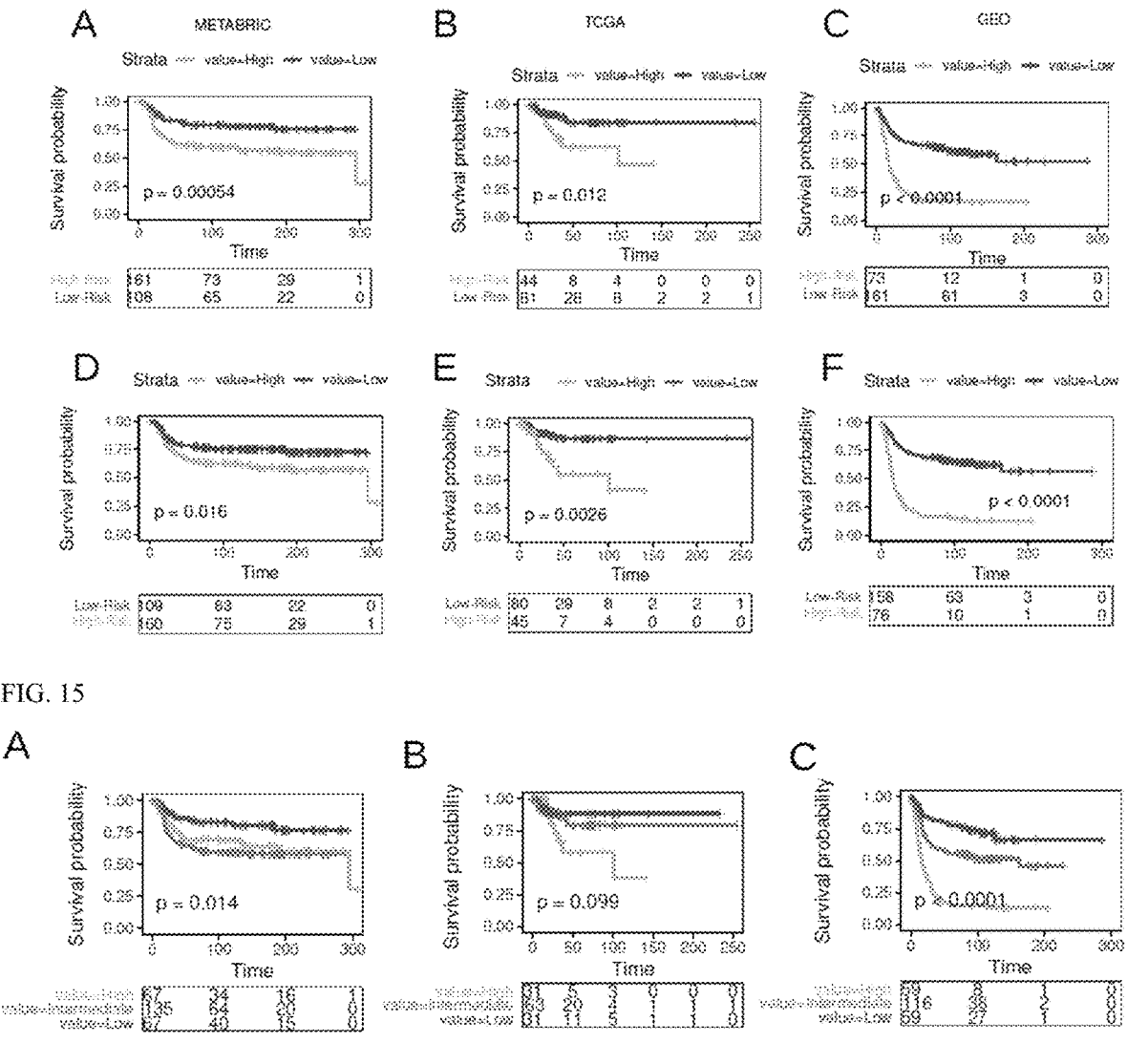
FIG. 14: Recurrence-free survival of BRAVO-DX across validation cohorts. A-C) Recurrence-free survival for patients stratified by the cumulative expression of 21 BRAVO-DX marker genes across the METABRIC A), TCGA B), and GEO C) cohorts. D-F) Analogously, recurrence-free survival for patients stratified by the cumulative expression of 12 BRAVO-IMMUNE marker genes, across the METABRIC D), TCGA E), and GEO F) cohorts.
FIG. 15: Risk-stratified recurrence-free survival of BRAVO-DX across three large validation cohorts. A-C) Recurrence-free survival for patients stratified by the cumulative expression of 21 BRAVO-DX marker genes across the METABRIC (A), TCGA (B), and GEO (C) cohorts.
Figure 16:
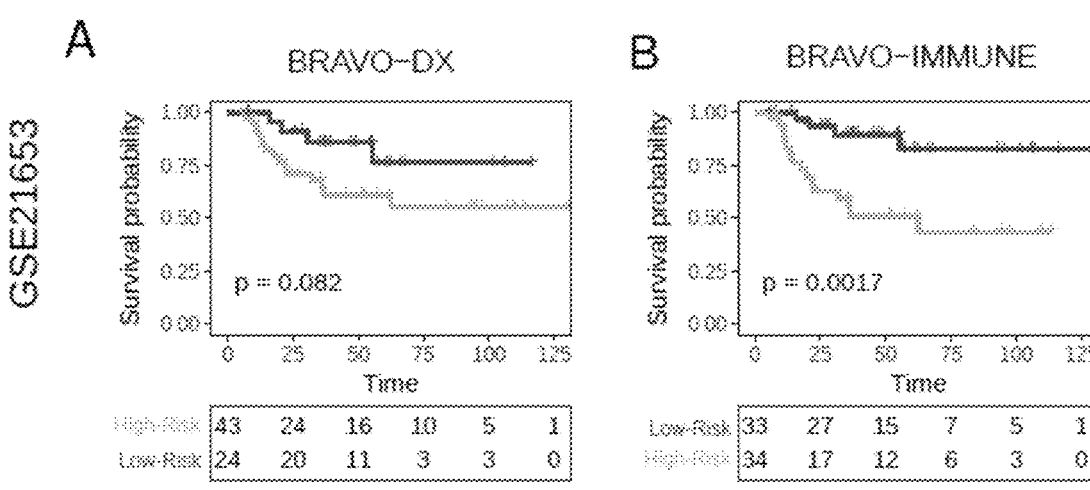
FIG. 16: Recurrence-free survival of BRAVO-DX across two small validation cohorts. Recurrence-free survival for patients stratified by the cumulative expression of 21 BRAVO-DX marker genes across the A) GSE21653 and C) E-MTAB-365 cohorts. Analogously, recurrence-free survival for patients stratified by the cumulative expression (high-risk; low-risk) of 12 BRAVO-IMMUNE marker genes, across the B) GSE21653 and D) E-MTAB-365 cohorts.
Figure 16:
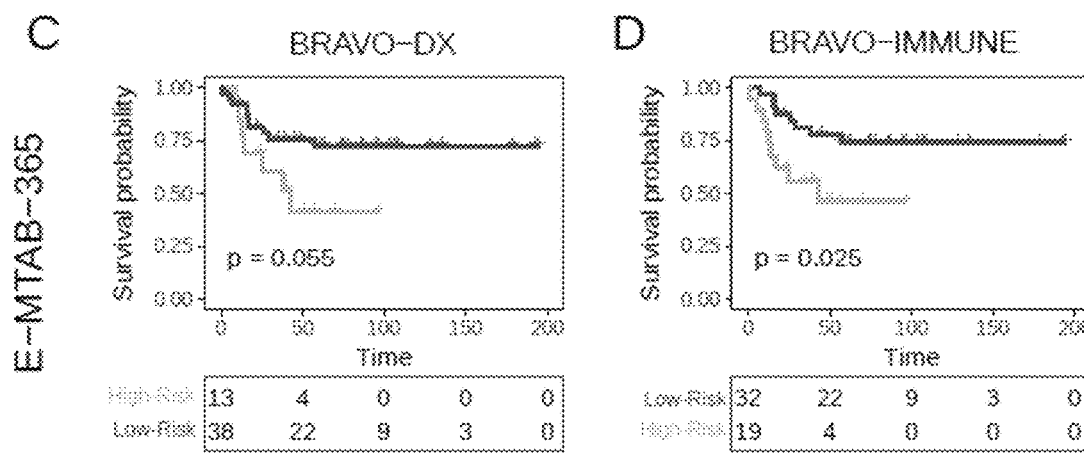

For evaluation, three large primary breast cancer cohorts with long term follow-up were selected (Table 9). The three cohorts utilized different transcriptome profiling platforms (i.e., polyA+ RNA-seq, Affymetrix microarray, and Illumina BeadChip) and, hence, were processed, normalized, and evaluated separately. All patients classified with basal-like or triple-negative diseases were included with no additional inclusion/exclusion criteria. Despite differences in mean follow-up time and event frequency, BRAVO-DX and BRAVO-IMMUNE were highly prognostic for overall survival in all validation cohorts (FIG. 5A, FIG. 13A). Notably, BRAVO-DX was more strongly prognostic in patients with favorable prognosis (NPI<5.4) (FIG. 13B). The three individual genes IKZF3, AIM2, and ELF3 were also significantly (p<0.05) associated with recurrence-free survival in eight out of nine validations (FIG. 5B, FIG. 13C). Overall, BRAVO signatures had the highest predictive performance for the Gyorffy et al. microarray-based cohort (GEO) (BRAVO-DX: HR=3.45, p<0.0001; BRAVO-IMMUNE: HR=4.33, p<0.0001) (Table 10), which highlights their ability to generalize across transcriptomic platforms. Next, it was determined whether BRAVO-DX was analogously predictive of recurrence-free survival in the validation cohorts. It was found that both BRAVO-DX and BRAVO-IMMUNE scores predict recurrence for patients dichotomized by their expression (FIG. 14A-F) and three-group splits (FIG. 15A-C). In two additional smaller cohorts that were evaluated, BRAVO-DX showed similar trends in predicting recurrence-free survival (FIG. 16A,C), while BRAVO-IMMUNE reached statistical significance (FIG. 16B,D).

In order to establish the relative performance of BRAVO-DX, it was compared to state-of-the-art prognostic signatures. A battery of 14 marker panels proposed by Rody et al. (64) was evaluated side-by-side with BRAVO-DX and BRAVO-IMMUNE on the BRAVO cohort and the three large validation cohorts (FIG. 5C, FIG. 13D). BRAVO signatures achieved highest average accuracy in the discovery cohort (FIG. 5C), followed by IFN and MHC-2. In two of the validation cohorts, BRAVO signatures ranked best in terms of prognostic significance, followed by apocrine and MHC-I panels. Notably, a proliferation-based score was highly significant in the treatment-naive TCGA tumors, but was not validated in the other cohorts. To better understand the functional relationships among signatures, their correlation with the BRAVO cohort was investigated (FIG. 13E). As expected, BRAVO-IMMUNE was similar to other signatures probing the tumor immune-phenotype. The remaining BRAVO-INTRINSIC genes correlated most strongly with a signature of claudin-low tumors (65).

Figure 6:
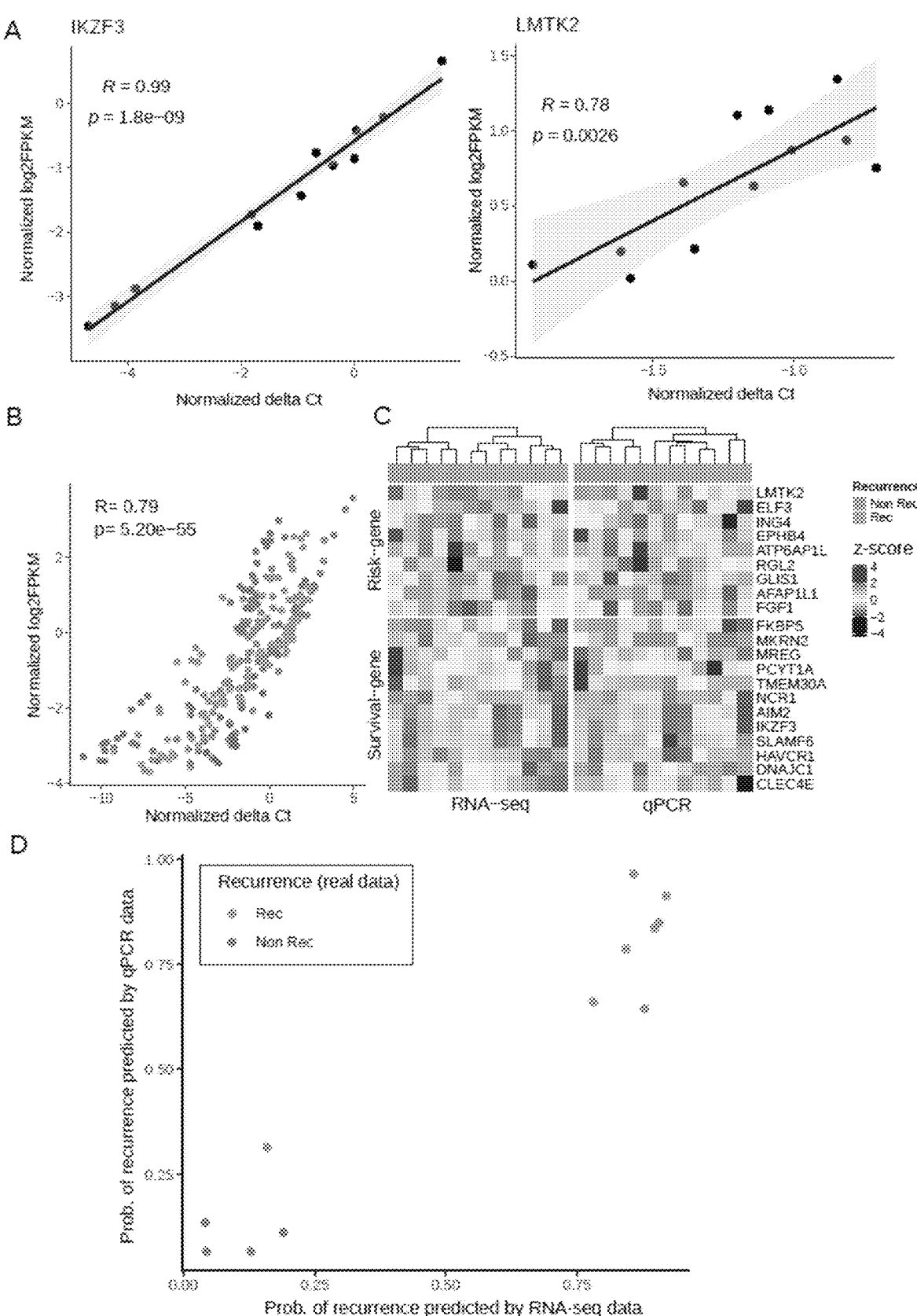
FIG. 6. Validation of BRAVO-DX signature using TaqMan real-time PCR assay. A) Scatter plots showing expression levels of IKZF3 and LMTK2 quantified by RNA-seq and real-time PCR (qPCR). B) Overall correlation (Pearson's) between expression levels from RNA-seq and qPCR across all tested genes and samples. C) Heatmap of gene expression level measured by RNA-seq and qPCR across samples. D) Scatter plot showing probability of recurrence predicted by RNA-seq data and qPCR data, which is highly concordant.

To test the potential use of BRAVO signatures in the clinical realm, an alternative technique based on TaqMan real-time PCR was used to validate selected biomarkers using a subset of tumor samples. Such a method is likely easier to implement due to lower cost, shorter turn-around time, and potentially lower RNA input requirement. Quantification of selected genes by real-time PCR was highly concordant with RNA-seq, with Pearson's correlation ranging from 0.78-0.99 (FIG. 6A, Table 11) for individual genes and 0.79 for all genes (FIG. 6B). The differences between recurrent and non-recurrent cases in expression of risk-genes and survival-genes was well preserved by the TaqMan PCR assay (FIG. 6C). To test the fidelity of qPCR results in predicting recurrence, Ct values were converted into log FPKM using a formula derived from linear regression and used in the random forest model trained from the RNA-seq data. The results indicated that predictions from the two platforms were highly consistent (FIG. 6D). These data demonstrate that the BRAVO-DX panel should perform equally well on a qPCR platform.

TABLE 1

| gene_id | gene_name | Length | logFC | AveExpr | t | P. Value | adj. P. Val | B |
|---------|-----------|--------|-------|---------|---|----------|-------------|---|
| ENSG00000142615.7 | CELA2A | 919 | 0.95 | −1.50 | 2.55 | 0.0120 | 0.6648 | −3.30 |
| ENSG00000215704.9 | CELA2B | 923 | 0.75 | 0.69 | 2.51 | 0.0135 | 0.6804 | −3.21 |
| ENSG00000162461.7 | SLC25A34 | 2986 | 0.75 | 0.84 | 2.70 | 0.0080 | 0.6271 | −2.91 |
| ENSG00000173372.16 | C1QA | 1143 | −0.53 | 5.76 | −2.37 | 0.0194 | 0.7142 | −3.30 |
| ENSG00000173369.15 | C1QB | 1254 | −0.57 | 6.49 | −2.83 | 0.0054 | 0.6040 | −2.28 |
| ENSG00000169442.8 | CD52 | 468 | −0.61 | 3.08 | −2.38 | 0.0189 | 0.7134 | −3.18 |
| ENSG00000060656.19 | PTPRU | 5640 | 0.51 | 6.01 | 2.26 | 0.0258 | 0.7312 | −3.54 |

TABLE 1-continued

| gene_id | gene_name | Length | logFC | AveExpr | t | P. Value | adj. P. Val | B |
|---|---|---|---|---|---|---|---|---|
| ENSG00000189280.3 | GJB5 | 1355 | 1.19 | 0.23 | 2.50 | 0.0139 | 0.6852 | −3.27 |
| ENSG00000154027.18 | AK5 | 4495 | 0.67 | 1.99 | 2.18 | 0.0312 | 0.7404 | −3.57 |
| ENSG00000016490.15 | CLCA1 | 3340 | 1.01 | −2.95 | 2.37 | 0.0194 | 0.7142 | −3.57 |
| ENSG00000143013.12 | LMO4 | 5405 | −0.57 | 5.56 | −2.44 | 0.0162 | 0.6941 | −3.15 |
| ENSG00000143028.8 | SYPL2 | 3624 | 0.85 | −0.90 | 2.31 | 0.0224 | 0.7255 | −3.57 |
| ENSG00000143119.12 | CD53 | 1505 | −0.58 | 6.24 | −3.13 | 0.0021 | 0.5606 | −1.49 |
| ENSG00000198765.11 | SYCP1 | 3525 | −1.34 | −1.92 | −2.28 | 0.0244 | 0.7261 | −3.64 |
| ENSG00000116824.4 | CD2 | 1679 | −0.84 | 4.75 | −3.25 | 0.0015 | 0.5292 | −1.18 |
| ENSG00000183508.4 | FAM46C | 5751 | −0.86 | 5.11 | −3.21 | 0.0017 | 0.5541 | −1.28 |
| ENSG00000173080.5 | RXFP4 | 1240 | 0.97 | −0.29 | 2.36 | 0.0198 | 0.7160 | −3.48 |
| ENSG00000187862.11 | TTC24 | 2005 | −0.83 | 0.35 | −2.09 | 0.0388 | 0.7787 | −3.78 |
| ENSG00000163564.14 | PYHIN1 | 2937 | −0.77 | 3.69 | −2.96 | 0.0037 | 0.5744 | −1.96 |
| ENSG00000196184.8 | OR10J1 | 1090 | −0.74 | −5.04 | −2.00 | 0.0482 | 0.8058 | −3.99 |
| ENSG00000158714.10 | SLAMF8 | 2996 | −0.60 | 2.95 | −2.25 | 0.0263 | 0.7312 | −3.41 |
| ENSG00000026751.16 | SLAMF7 | 2936 | −0.88 | 3.93 | −3.17 | 0.0019 | 0.5544 | −1.44 |
| ENSG00000117152.13 | RGS4 | 3518 | 0.66 | 2.22 | 2.30 | 0.0232 | 0.7255 | −3.37 |
| ENSG00000198771.10 | RCSD1 | 3135 | −0.55 | 4.40 | −2.97 | 0.0036 | 0.5744 | −1.89 |
| ENSG00000134376.14 | CRB1 | 11330 | 1.04 | −0.29 | 2.69 | 0.0080 | 0.6271 | −3.04 |
| ENSG00000081237.18 | PTPRC | 7151 | −0.54 | 7.54 | −2.72 | 0.0075 | 0.6271 | −2.58 |
| ENSG00000163435.15 | ELF3 | 3179 | 0.58 | 6.24 | 2.80 | 0.0058 | 0.6105 | −2.33 |
| ENSG00000133067.17 | LGR6 | 3790 | 1.01 | 4.18 | 2.35 | 0.0203 | 0.7175 | −3.24 |
| ENSG00000188770.9 | OPTC | 1359 | 0.73 | −3.83 | 2.00 | 0.0474 | 0.8040 | −3.97 |
| ENSG00000122188.12 | LAX1 | 3023 | −1.10 | 3.21 | −3.85 | 0.0002 | 0.3351 | 0.18 |
| ENSG00000263961.6 | C1orf186 | 1787 | −1.05 | 1.53 | −2.14 | 0.0339 | 0.7586 | −3.64 |
| ENSG00000054392.12 | HHAT | 6641 | 0.55 | 3.07 | 2.74 | 0.0071 | 0.6271 | −2.50 |
| ENSG00000185155.11 | MIXL1 | 2029 | −0.83 | −1.24 | −2.16 | 0.0331 | 0.7568 | −3.76 |
| ENSG00000187642.9 | PERM1 | 3407 | 0.59 | 1.46 | 2.02 | 0.0456 | 0.7985 | −3.81 |
| ENSG00000205090.8 | TMEM240 | 1380 | 0.77 | 0.62 | 2.27 | 0.0251 | 0.7312 | −3.54 |
| ENSG00000049249.8 | TNFRSF9 | 5970 | −0.86 | 1.68 | −3.20 | 0.0018 | 0.5541 | −1.87 |
| ENSG00000142583.17 | SLC2A5 | 5760 | −0.69 | 2.88 | −2.82 | 0.0056 | 0.6040 | −2.36 |
| ENSG00000116771.5 | AGMAT | 2500 | −0.51 | 1.08 | −2.21 | 0.0288 | 0.7392 | −3.58 |
| ENSG00000117215.14 | PLA2G2D | 2681 | −1.04 | −0.76 | −2.33 | 0.0214 | 0.7189 | −3.54 |
| ENSG00000158014.14 | SLC30A2 | 3264 | 1.15 | −1.20 | 2.34 | 0.0210 | 0.7180 | −3.55 |
| ENSG00000176083.17 | ZNF683 | 1713 | −0.85 | 2.12 | −2.41 | 0.0173 | 0.6941 | −3.20 |
| ENSG00000116985.10 | BMP8B | 5143 | 0.52 | 1.43 | 2.21 | 0.0288 | 0.7392 | −3.56 |
| ENSG00000066185.12 | ZMYND12 | 1775 | 0.74 | 0.92 | 2.18 | 0.0310 | 0.7404 | −3.63 |
| ENSG00000162367.11 | TAL1 | 4642 | 0.72 | 0.66 | 2.45 | 0.0156 | 0.6941 | −3.29 |
| ENSG00000174332.5 | GLIS1 | 2812 | 1.13 | 0.52 | 3.31 | 0.0012 | 0.5186 | −1.95 |
| ENSG00000162654.8 | GBP4 | 6127 | −0.92 | 4.93 | −3.86 | 0.0002 | 0.3351 | 0.60 |
| ENSG00000154451.14 | GBP5 | 2011 | −0.95 | 5.67 | −3.33 | 0.0012 | 0.5186 | −0.95 |
| ENSG00000221986.6 | MYBPHL | 1372 | 0.91 | 0.54 | 2.30 | 0.0233 | 0.7255 | −3.51 |
| ENSG00000177272.8 | KCNA3 | 2569 | −0.68 | 4.28 | −2.29 | 0.0238 | 0.7255 | −3.37 |
| ENSG00000272031.2 | ANKRD34A | 3613 | 0.58 | 2.00 | 2.47 | 0.0149 | 0.6852 | −3.12 |
| ENSG00000163131.10 | CTSS | 4107 | −0.51 | 6.05 | −2.63 | 0.0095 | 0.6449 | −2.73 |
| ENSG00000196407.11 | THEM5 | 984 | 0.76 | 2.80 | 2.64 | 0.0095 | 0.6449 | −2.73 |
| ENSG00000143631.10 | FLG | 12747 | 0.58 | 3.20 | 2.04 | 0.0436 | 0.7916 | −3.76 |
| ENSG00000125462.16 | C1orf61 | 885 | 1.07 | −0.24 | 2.15 | 0.0333 | 0.7586 | −3.73 |
| ENSG00000143297.18 | FCRL5 | 8508 | −1.07 | 3.99 | −2.91 | 0.0043 | 0.5942 | −2.05 |
| ENSG00000163518.10 | FCRL4 | 3459 | −1.12 | −2.58 | −2.64 | 0.0094 | 0.6449 | −3.23 |
| ENSG00000160856.20 | FCRL3 | 2633 | −0.91 | 2.70 | −2.53 | 0.0127 | 0.6761 | −2.94 |
| ENSG00000132704.15 | FCRL2 | 3095 | −0.91 | 1.45 | −2.34 | 0.0210 | 0.7180 | −3.38 |
| ENSG00000163568.13 | AIM2 | 1529 | −1.16 | 2.28 | −3.90 | 0.0002 | 0.3351 | −0.11 |
| ENSG00000162739.13 | SLAMF6 | 2746 | −0.98 | 2.79 | −3.66 | 0.0004 | 0.3614 | −0.47 |
| ENSG00000117090.14 | SLAMF1 | 4089 | −0.76 | 2.86 | −2.76 | 0.0066 | 0.6235 | −2.47 |
| ENSG00000122223.12 | CD244 | 2478 | −0.77 | 0.41 | −2.67 | 0.0087 | 0.6321 | −3.01 |
| ENSG00000198821.10 | CD247 | 1681 | −0.72 | 2.49 | −2.72 | 0.0075 | 0.6271 | −2.61 |
| ENSG00000188404.8 | SELL | 2436 | −0.91 | 3.70 | −3.20 | 0.0017 | 0.5541 | −1.38 |
| ENSG00000118194.18 | TNNT2 | 1224 | 0.80 | 1.20 | 2.40 | 0.0177 | 0.6941 | −3.31 |
| ENSG00000133055.8 | MYBPH | 1805 | 0.94 | 1.75 | 2.21 | 0.0290 | 0.7392 | −3.54 |
| ENSG00000133063.15 | CHIT1 | 2246 | −1.18 | 0.73 | −3.03 | 0.0030 | 0.5744 | −2.38 |
| ENSG00000182795.12 | C1orf116 | 5502 | 0.63 | 5.58 | 2.46 | 0.0152 | 0.6904 | −3.10 |
| ENSG00000168148.3 | HIST3H3 | 481 | 0.74 | 0.18 | 2.03 | 0.0444 | 0.7926 | −3.85 |
| ENSG00000197437.3 | OR13G1 | 924 | −1.01 | −2.54 | −2.16 | 0.0331 | 0.7568 | −3.79 |
| ENSG00000163803.12 | PLB1 | 5181 | 0.50 | 4.09 | 2.49 | 0.0140 | 0.6852 | −2.96 |
| ENSG00000187600.12 | TMEM247 | 680 | 0.95 | −2.29 | 2.56 | 0.0117 | 0.6630 | −3.32 |
| ENSG00000177994.15 | C2orf73 | 2241 | 1.02 | −2.06 | 2.83 | 0.0054 | 0.6040 | −2.95 |
| ENSG00000144031.11 | ANKRD53 | 2185 | 0.58 | 2.08 | 2.07 | 0.0404 | 0.7844 | −3.72 |
| ENSG00000152292.16 | SH2D6 | 2331 | −0.94 | −2.25 | −2.43 | 0.0165 | 0.6941 | −3.47 |
| ENSG00000115523.16 | GNLY | 1090 | −0.97 | 2.43 | −2.71 | 0.0078 | 0.6271 | −2.65 |
| ENSG00000115085.13 | ZAP70 | 2551 | −0.63 | 3.51 | −2.14 | 0.0343 | 0.7610 | −3.60 |
| ENSG00000115607.9 | IL18RAP | 2773 | −0.74 | 1.56 | −2.93 | 0.0041 | 0.5940 | −2.40 |
| ENSG00000136682.14 | CBWD2 | 1900 | 0.62 | −1.37 | 2.48 | 0.0143 | 0.6852 | −3.38 |
| ENSG00000175497.16 | DPP10 | 7441 | 1.42 | −2.16 | 2.24 | 0.0270 | 0.7330 | −3.69 |
| ENSG00000136002.16 | ARHGEF4 | 8325 | 0.51 | 5.01 | 2.00 | 0.0475 | 0.8040 | −3.96 |
| ENSG00000163040.14 | CCDC74A | 1543 | 0.73 | 1.54 | 2.24 | 0.0267 | 0.7312 | −3.51 |
| ENSG00000153086.13 | ACMSD | 1428 | 0.79 | 2.62 | 3.33 | 0.0011 | 0.5186 | −1.32 |
| ENSG00000075884.12 | ARHGAP15 | 1775 | −0.53 | 4.21 | −2.72 | 0.0074 | 0.6271 | −2.47 |
| ENSG00000073737.16 | DHRS9 | 1963 | −0.91 | −0.39 | −2.15 | 0.0335 | 0.7586 | −3.74 |

TABLE 1-continued

| gene_id | gene_name | Length | logFC | AveExpr | t | P. Value | adj. P. Val | B |
|---|---|---|---|---|---|---|---|---|
| ENSG00000144355.14 | DLX1 | 2640 | 1.39 | −1.69 | 2.43 | 0.0166 | 0.6941 | −3.46 |
| ENSG00000138395.14 | CDK15 | 4848 | 0.76 | 0.44 | 2.12 | 0.0361 | 0.7726 | −3.74 |
| ENSG00000163599.14 | CTLA4 | 1977 | −0.86 | 2.34 | −3.31 | 0.0012 | 0.5186 | −1.45 |
| ENSG00000163600.12 | ICOS | 2645 | −0.81 | 1.39 | −2.41 | 0.0175 | 0.6941 | −3.28 |
| ENSG00000072195.14 | SPEG | 2366 | 0.53 | 4.49 | 2.37 | 0.0194 | 0.7142 | −3.23 |
| ENSG00000079263.18 | SP140 | 3577 | −0.64 | 4.24 | −2.91 | 0.0042 | 0.5942 | −2.03 |
| ENSG00000177673.3 | C2orf57 | 1383 | 0.87 | −3.36 | 2.29 | 0.0239 | 0.7255 | −3.67 |
| ENSG00000214842.5 | RAD51AP2 | 3724 | 0.74 | 1.56 | 2.28 | 0.0241 | 0.7255 | −3.45 |
| ENSG00000157884.10 | CIB4 | 773 | 1.10 | −2.15 | 2.69 | 0.0081 | 0.6271 | −3.14 |
| ENSG00000115194.10 | SLC30A3 | 2260 | 0.89 | −1.95 | 2.03 | 0.0441 | 0.7916 | −3.90 |
| ENSG00000163794.6 | UCN | 795 | 1.15 | −0.88 | 3.24 | 0.0015 | 0.5292 | −2.28 |
| ENSG00000171174.13 | RBKS | 2013 | 0.51 | 2.26 | 2.52 | 0.0130 | 0.6761 | −3.01 |
| ENSG00000179270.6 | C2orf71 | 7044 | 1.03 | −1.12 | 2.07 | 0.0410 | 0.7876 | −3.85 |
| ENSG00000179915.20 | NRXN1 | 14071 | 1.04 | 0.15 | 2.12 | 0.0360 | 0.7726 | −3.75 |
| ENSG00000178021.10 | TSPYL6 | 3089 | 0.60 | 2.77 | 2.26 | 0.0255 | 0.7312 | −3.40 |
| ENSG00000244617.2 | ASPRV1 | 2177 | 0.76 | 1.11 | 2.28 | 0.0240 | 0.7255 | −3.48 |
| ENSG00000153563.15 | CD8A | 2873 | −0.88 | 3.00 | −2.64 | 0.0093 | 0.6449 | −2.69 |
| ENSG00000136541.14 | ERMN | 4186 | −0.70 | 1.35 | −2.52 | 0.0131 | 0.6761 | −3.12 |
| ENSG00000115165.9 | CYTIP | 2260 | −0.64 | 5.10 | −2.83 | 0.0054 | 0.6040 | −2.23 |
| ENSG00000119042.16 | SATB2 | 4972 | 0.60 | 3.40 | 2.33 | 0.0214 | 0.7189 | −3.26 |
| ENSG00000135917.13 | SLC19A3 | 3105 | 0.79 | 1.80 | 2.35 | 0.0204 | 0.7175 | −3.33 |
| ENSG00000188389.10 | PDCD1 | 2114 | −1.01 | 0.97 | −3.04 | 0.0029 | 0.5744 | −2.32 |
| ENSG00000206559.7 | ZCWPW2 | 1716 | 0.53 | 0.97 | 2.20 | 0.0294 | 0.7392 | −3.60 |
| ENSG00000183813.6 | CCR4 | 3095 | −0.86 | 2.30 | −2.40 | 0.0177 | 0.6941 | −3.19 |
| ENSG00000240747.7 | KRBOX1 | 2662 | 1.16 | 0.11 | 2.90 | 0.0044 | 0.5978 | −2.69 |
| ENSG00000121807.5 | CCR2 | 3638 | −0.75 | 2.57 | −2.21 | 0.0292 | 0.7392 | −3.49 |
| ENSG00000160791.13 | CCR5 | 3450 | −0.75 | 3.71 | −2.62 | 0.0100 | 0.6498 | −2.71 |
| ENSG00000179564.3 | LSMEM2 | 1494 | 0.82 | −0.17 | 2.20 | 0.0299 | 0.7398 | −3.68 |
| ENSG00000055957.10 | ITIH1 | 3251 | 0.85 | −1.33 | 2.21 | 0.0288 | 0.7392 | −3.70 |
| ENSG00000157388.13 | CACNA1D | 9488 | 0.61 | 4.82 | 2.08 | 0.0392 | 0.7787 | −3.80 |
| ENSG00000163519.13 | TRAT1 | 1919 | −0.94 | 1.42 | −2.70 | 0.0079 | 0.6271 | −2.81 |
| ENSG00000153283.12 | CD96 | 4850 | −0.68 | 4.27 | −2.70 | 0.0079 | 0.6271 | −2.52 |
| ENSG00000144852.16 | NR1I2 | 4560 | −0.80 | −2.09 | −2.00 | 0.0475 | 0.8040 | −3.94 |
| ENSG00000145087.12 | STXBP5L | 9496 | −0.97 | 1.10 | −2.76 | 0.0066 | 0.6235 | −2.76 |
| ENSG00000163833.7 | FBXO40 | 5929 | −0.97 | −3.85 | −2.53 | 0.0128 | 0.6761 | −3.42 |
| ENSG00000173200.12 | PARP15 | 5214 | −0.54 | 4.14 | −2.44 | 0.0160 | 0.6941 | −3.07 |
| ENSG00000170819.4 | BFSP2 | 1558 | −1.05 | 0.27 | −2.99 | 0.0034 | 0.5744 | −2.53 |
| ENSG00000132182.11 | NUP210 | 7193 | −0.51 | 7.63 | −3.05 | 0.0028 | 0.5744 | −1.74 |
| ENSG00000163673.6 | DCLK3 | 5344 | 0.94 | 0.54 | 2.44 | 0.0161 | 0.6941 | −3.32 |
| ENSG00000168329.13 | CX3CR1 | 3655 | 0.58 | 1.93 | 2.14 | 0.0339 | 0.7586 | −3.62 |
| ENSG00000206549.12 | PRSS50 | 2959 | 0.92 | 1.38 | 2.31 | 0.0224 | 0.7255 | −3.42 |
| ENSG00000261603.1 | PRSS46 | 982 | 0.88 | −0.92 | 2.11 | 0.0370 | 0.7787 | −3.80 |
| ENSG00000008300.14 | CELSR3 | 11956 | 0.53 | 5.72 | 2.08 | 0.0393 | 0.7787 | −3.86 |
| ENSG00000114378.16 | HYAL1 | 2381 | 0.74 | 3.31 | 3.02 | 0.0031 | 0.5744 | −1.86 |
| ENSG00000272573.5 | MUSTN1 | 902 | 0.70 | 1.62 | 2.24 | 0.0270 | 0.7330 | −3.51 |
| ENSG00000174844.14 | DNAH12 | 9696 | 0.77 | 2.23 | 2.87 | 0.0048 | 0.6023 | −2.38 |
| ENSG00000178700.7 | DHFRL1 | 4038 | 0.54 | −0.29 | 2.65 | 0.0092 | 0.6449 | −3.11 |
| ENSG00000177494.5 | ZBED2 | 2311 | −0.76 | 2.51 | −2.13 | 0.0354 | 0.7686 | −3.62 |
| ENSG00000163606.10 | CD200R1 | 3905 | −0.99 | 1.45 | −3.70 | 0.0003 | 0.3579 | −0.92 |
| ENSG00000082684.14 | SEMA5B | 5417 | 0.64 | 2.45 | 2.12 | 0.0357 | 0.7712 | −3.63 |
| ENSG00000196542.8 | SPTSSB | 3103 | 0.94 | 0.24 | 2.03 | 0.0446 | 0.7941 | −3.85 |
| ENSG00000163581.13 | SLC2A2 | 3210 | 0.95 | −0.45 | 2.09 | 0.0387 | 0.7787 | −3.81 |
| ENSG00000078081.7 | LAMP3 | 3470 | −0.62 | 4.45 | −2.76 | 0.0066 | 0.6235 | −2.38 |
| ENSG00000172578.11 | KLHL6 | 6298 | −0.64 | 4.48 | −3.30 | 0.0013 | 0.5186 | −1.04 |
| ENSG00000184160.7 | ADRA2C | 2179 | 1.00 | −0.43 | 2.07 | 0.0404 | 0.7844 | −3.83 |
| ENSG00000004468.12 | CD38 | 5668 | −0.95 | 2.67 | −3.07 | 0.0027 | 0.5744 | −1.88 |
| ENSG00000197057.8 | DTHD1 | 3933 | −0.91 | 2.22 | −3.03 | 0.0030 | 0.5744 | −2.07 |
| ENSG00000174145.7 | NWD2 | 8325 | 1.24 | −0.20 | 3.00 | 0.0033 | 0.5744 | −2.58 |
| ENSG00000168421.12 | RHOH | 5154 | −0.76 | 2.80 | −2.96 | 0.0036 | 0.5744 | −2.07 |
| ENSG00000181617.5 | FDCSP | 566 | −1.49 | 3.43 | −2.07 | 0.0409 | 0.7867 | −3.72 |
| ENSG00000187689.9 | AMTN | 1037 | −1.24 | −2.61 | −2.12 | 0.0360 | 0.7726 | −3.83 |
| ENSG00000178522.14 | AMBN | 2009 | −1.25 | −3.35 | −2.98 | 0.0035 | 0.5744 | −2.83 |
| ENSG00000132464.11 | ENAM | 5679 | −1.04 | −0.03 | −2.61 | 0.0101 | 0.6507 | −3.13 |
| ENSG00000169429.10 | CXCL8 | 2003 | 0.76 | 1.82 | 2.00 | 0.0480 | 0.8040 | −3.83 |
| ENSG00000189157.13 | FAM47E | 2050 | 0.73 | 1.19 | 2.35 | 0.0203 | 0.7175 | −3.38 |
| ENSG00000156234.7 | CXCL13 | 1203 | −1.17 | 3.85 | −2.91 | 0.0043 | 0.5942 | −2.07 |
| ENSG00000237136.6 | C4orf51 | 846 | −1.22 | −3.19 | −2.32 | 0.0218 | 0.7238 | −3.62 |
| ENSG00000151615.3 | POU4F2 | 3144 | −0.79 | −4.70 | −2.05 | 0.0424 | 0.7905 | −3.93 |
| ENSG00000250486.3 | FAM218A | 2175 | 0.87 | 0.16 | 2.09 | 0.0390 | 0.7787 | −3.79 |
| ENSG00000159674.11 | SPON2 | 2482 | 0.69 | 5.85 | 3.10 | 0.0024 | 0.5744 | −1.58 |
| ENSG00000130997.16 | POLN | 3253 | 0.51 | 2.80 | 2.27 | 0.0249 | 0.7312 | −3.38 |
| ENSG00000152969.16 | JAKMIP1 | 3433 | −0.83 | 1.63 | −2.58 | 0.0112 | 0.6630 | −2.99 |
| ENSG00000178597.5 | PSAPL1 | 2688 | 1.21 | 0.30 | 2.79 | 0.0061 | 0.6206 | −2.84 |
| ENSG00000109684.14 | CLNK | 6206 | −0.78 | 1.31 | −2.59 | 0.0109 | 0.6630 | −3.01 |
| ENSG00000137441.7 | FGFBP2 | 1168 | 1.16 | −1.14 | 2.38 | 0.0186 | 0.7082 | −3.49 |
| ENSG00000091490.10 | SEL1L3 | 4682 | −0.52 | 6.38 | −3.25 | 0.0015 | 0.5292 | −1.17 |
| ENSG00000121895.7 | TMEM156 | 1935 | −0.99 | 1.33 | −3.15 | 0.0021 | 0.5544 | −2.05 |
| ENSG00000271271.5 | UGT2A2 | 1676 | −0.71 | −5.93 | −2.54 | 0.0123 | 0.6712 | −3.46 |

TABLE 1-continued

| gene_id | gene_name | Length | logFC | AveExpr | t | P. Value | adj. P. Val | B |
|---|---|---|---|---|---|---|---|---|
| ENSG00000132465.10 | JCHAIN | 1438 | −0.96 | 4.93 | −2.74 | 0.0070 | 0.6271 | −2.44 |
| ENSG00000138755.5 | CXCL9 | 2740 | −1.20 | 4.49 | −3.38 | 0.0010 | 0.5186 | −0.84 |
| ENSG00000169245.5 | CXCL10 | 1176 | −0.68 | 4.77 | −2.24 | 0.0267 | 0.7312 | −3.50 |
| ENSG00000145287.10 | PLAC8 | 1447 | −0.67 | 0.49 | −2.17 | 0.0316 | 0.7434 | −3.67 |
| ENSG00000169989.2 | TIGD4 | 2472 | 0.87 | 0.36 | 2.54 | 0.0122 | 0.6667 | −3.19 |
| ENSG00000168685.14 | IL7R | 4908 | −0.77 | 5.13 | −3.14 | 0.0021 | 0.5544 | −1.45 |
| ENSG00000113088.5 | GZMK | 1509 | −1.16 | 1.55 | −3.09 | 0.0025 | 0.5744 | −2.11 |
| ENSG00000145649.7 | GZMA | 894 | −0.96 | 1.48 | −2.66 | 0.0088 | 0.6323 | −2.87 |
| ENSG00000164309.14 | CMYA5 | 12847 | 0.59 | 6.99 | 2.81 | 0.0057 | 0.6040 | −2.33 |
| ENSG00000164308.16 | ERAP2 | 5888 | −0.59 | 5.63 | −2.81 | 0.0057 | 0.6040 | −2.30 |
| ENSG00000113396.12 | SLC27A6 | 3219 | 1.66 | 1.57 | 3.54 | 0.0006 | 0.4557 | −1.23 |
| ENSG00000243232.4 | PCDHAC2 | 6112 | 0.67 | 1.63 | 2.05 | 0.0422 | 0.7905 | −3.76 |
| ENSG00000120328.6 | PCDHB12 | 3875 | 0.63 | 3.22 | 2.23 | 0.0275 | 0.7349 | −3.44 |
| ENSG00000113248.5 | PCDHB15 | 4017 | 0.52 | 3.16 | 2.04 | 0.0439 | 0.7916 | −3.76 |
| ENSG00000253537.2 | PCDHGA7 | 5443 | 0.60 | 4.73 | 2.17 | 0.0323 | 0.7524 | −3.64 |
| ENSG00000183775.10 | KCTD16 | 2313 | 1.09 | −1.32 | 2.70 | 0.0079 | 0.6271 | −3.10 |
| ENSG00000113263.12 | ITK | 4528 | −0.72 | 3.49 | −2.70 | 0.0079 | 0.6271 | −2.54 |
| ENSG00000113430.9 | IRX4 | 2540 | 1.87 | 0.49 | 3.04 | 0.0029 | 0.5744 | −2.41 |
| ENSG00000215217.6 | C5orf49 | 2385 | 0.93 | −2.27 | 2.39 | 0.0185 | 0.7082 | −3.52 |
| ENSG00000145626.11 | UGT3A1 | 7920 | −0.84 | −5.32 | −2.33 | 0.0214 | 0.7189 | −3.67 |
| ENSG00000082074.15 | FYB | 4977 | −0.55 | 7.03 | −3.03 | 0.0030 | 0.5744 | −1.79 |
| ENSG00000173930.8 | SLCO4C1 | 5334 | −0.82 | 0.51 | −2.10 | 0.0375 | 0.7787 | −3.75 |
| ENSG00000170476.15 | MZB1 | 825 | −1.30 | 2.94 | −3.98 | 0.0001 | 0.3351 | 0.40 |
| ENSG00000249751.3 | ECSCR | 1035 | 0.58 | 0.60 | 2.08 | 0.0393 | 0.7787 | −3.77 |
| ENSG00000256453.1 | DND1 | 1605 | 0.82 | −0.07 | 2.51 | 0.0133 | 0.6762 | −3.27 |
| ENSG00000113578.17 | FGF1 | 4992 | 1.03 | 1.54 | 4.13 | 0.0001 | 0.3351 | 0.06 |
| ENSG00000164266.10 | SPINK1 | 1478 | 0.93 | −1.88 | 2.07 | 0.0405 | 0.7844 | −3.86 |
| ENSG00000169247.11 | SH3TC2 | 6261 | 1.03 | 1.94 | 2.94 | 0.0039 | 0.5908 | −2.30 |
| ENSG00000113249.12 | HAVCR1 | 2147 | −0.74 | 0.20 | −2.18 | 0.0311 | 0.7404 | −3.68 |
| ENSG00000137265.14 | IRF4 | 5331 | −0.82 | 3.79 | −2.62 | 0.0100 | 0.6498 | −2.70 |
| ENSG00000204657.3 | OR2H2 | 1584 | 0.99 | −0.17 | 2.38 | 0.0187 | 0.7089 | −3.45 |
| ENSG00000204482.10 | LST1 | 1041 | −0.52 | 2.81 | −2.48 | 0.0145 | 0.6852 | −3.02 |
| ENSG00000204287.13 | HLA-DRA | 1280 | −0.52 | 7.98 | −2.89 | 0.0045 | 0.6023 | −2.16 |
| ENSG00000196735.11 | HLA-DQA1 | 1591 | −0.75 | 6.11 | −2.52 | 0.0132 | 0.6761 | −3.00 |
| ENSG00000240065.7 | PSMB9 | 921 | −0.68 | 3.95 | −2.96 | 0.0037 | 0.5744 | −1.92 |
| ENSG00000223865.7 | HLA-DPB1 | 1560 | −0.51 | 6.00 | −3.08 | 0.0025 | 0.5744 | −1.62 |
| ENSG00000124713.5 | GNMT | 1072 | 0.62 | 2.14 | 2.16 | 0.0328 | 0.7536 | −3.59 |
| ENSG00000203972.9 | GLYATL3 | 1113 | 0.99 | −4.54 | 2.52 | 0.0131 | 0.6761 | −3.45 |
| ENSG00000188820.12 | FAM26F | 1140 | −0.75 | 1.59 | −2.40 | 0.0177 | 0.6941 | −3.26 |
| ENSG00000182747.4 | SLC35D3 | 2359 | −0.78 | −4.21 | −2.08 | 0.0394 | 0.7787 | −3.90 |
| ENSG00000203727.3 | SAMD5 | 6089 | 0.78 | 0.37 | 2.18 | 0.0310 | 0.7404 | −3.67 |
| ENSG00000112530.11 | PACRG | 1659 | 0.93 | −0.87 | 2.68 | 0.0082 | 0.6271 | −3.09 |
| ENSG00000145949.9 | MYLK4 | 5806 | 0.60 | 1.08 | 2.14 | 0.0341 | 0.7586 | −3.67 |
| ENSG00000124827.6 | GCM2 | 2441 | 0.95 | 0.77 | 2.46 | 0.0153 | 0.6916 | −3.27 |
| ENSG00000111913.15 | FAM65B | 7839 | −0.55 | 4.51 | −2.33 | 0.0214 | 0.7189 | −3.31 |
| ENSG00000204542.2 | C6orf15 | 1140 | 1.43 | −1.35 | 2.45 | 0.0156 | 0.6941 | −3.41 |
| ENSG00000227507.2 | LTB | 899 | −0.73 | 2.57 | −2.67 | 0.0085 | 0.6309 | −2.68 |
| ENSG00000196126.10 | HLA-DRB1 | 1304 | −0.60 | 5.97 | −2.58 | 0.0109 | 0.6630 | −2.84 |
| ENSG00000179344.16 | HLA-DQB1 | 1666 | −0.71 | 5.46 | −2.81 | 0.0057 | 0.6040 | −2.30 |
| ENSG00000168394.10 | TAP1 | 2959 | −0.57 | 7.33 | −2.77 | 0.0065 | 0.6235 | −2.44 |
| ENSG00000204252.12 | HLA-DOA | 3489 | −0.53 | 3.22 | −2.35 | 0.0201 | 0.7175 | −3.22 |
| ENSG00000231389.7 | HLA-DPA1 | 1704 | −0.58 | 6.54 | −3.49 | 0.0007 | 0.4759 | −0.49 |
| ENSG00000124678.17 | TCP11 | 2703 | 0.88 | −1.43 | 2.09 | 0.0386 | 0.7787 | −3.83 |
| ENSG00000096060.14 | FKBP5 | 10628 | −0.82 | 6.25 | −4.13 | 0.0001 | 0.3351 | 1.52 |
| ENSG00000164627.17 | KIF6 | 9447 | 0.78 | 0.01 | 2.06 | 0.0413 | 0.7905 | −3.82 |
| ENSG00000171462.14 | DLK2 | 1572 | 0.61 | 2.76 | 2.11 | 0.0373 | 0.7787 | −3.65 |
| ENSG00000174156.13 | GSTA3 | 1025 | 1.01 | −4.14 | 2.62 | 0.0098 | 0.6449 | −3.31 |
| ENSG00000124749.16 | COL21A1 | 4543 | 0.91 | 1.64 | 2.59 | 0.0109 | 0.6630 | −2.97 |
| ENSG00000146285.13 | SCML4 | 4038 | −0.96 | 1.46 | −3.29 | 0.0013 | 0.5230 | −1.74 |
| ENSG00000249853.7 | HS3ST5 | 3901 | 0.89 | −0.88 | 2.34 | 0.0208 | 0.7175 | −3.53 |
| ENSG00000172673.10 | THEMIS | 4309 | −0.81 | 3.71 | −2.92 | 0.0041 | 0.5940 | −2.03 |
| ENSG00000164483.16 | SAMD3 | 2790 | −0.63 | 3.08 | −2.86 | 0.0049 | 0.6023 | −2.23 |
| ENSG00000279968.1 | RP3-509119.11 | 2685 | 0.64 | −2.60 | 2.18 | 0.0314 | 0.7411 | −3.77 |
| ENSG00000178199.13 | ZC3H12D | 6029 | −0.56 | 2.69 | −2.65 | 0.0090 | 0.6424 | −2.71 |
| ENSG00000105877.17 | DNAH11 | 14194 | 0.69 | 5.22 | 2.10 | 0.0378 | 0.7787 | −3.80 |
| ENSG00000176532.3 | PRR15 | 1678 | 0.97 | 0.04 | 2.21 | 0.0289 | 0.7392 | −3.65 |
| ENSG00000078549.14 | ADCYAP1R1 | 6575 | 1.15 | 0.10 | 3.11 | 0.0023 | 0.5744 | −2.35 |
| ENSG00000185811.16 | IKZF1 | 7868 | −0.51 | 5.11 | −2.72 | 0.0075 | 0.6271 | −2.51 |
| ENSG00000188372.14 | ZP3 | 2505 | 0.84 | 3.38 | 3.67 | 0.0004 | 0.3614 | −0.24 |
| ENSG00000243566.6 | UPK3B | 2538 | 0.98 | 1.42 | 3.15 | 0.0021 | 0.5544 | −2.04 |
| ENSG00000128536.15 | CDHR3 | 3813 | 0.92 | 1.67 | 2.45 | 0.0158 | 0.6941 | −3.19 |
| ENSG00000128573.22 | FOXP2 | 8575 | 0.65 | 2.35 | 2.19 | 0.0304 | 0.7404 | −3.53 |
| ENSG00000214102.7 | WEE2 | 3061 | 0.69 | 2.36 | 2.98 | 0.0035 | 0.5744 | −2.14 |
| ENSG00000221858.2 | OR2A12 | 1046 | 1.08 | −0.30 | 2.86 | 0.0049 | 0.6023 | −2.79 |
| ENSG00000221989.2 | OR2A2 | 1051 | 0.79 | 0.05 | 2.01 | 0.0469 | 0.8040 | −3.88 |
| ENSG00000221938.3 | OR2A14 | 1422 | 1.22 | −0.65 | 2.82 | 0.0055 | 0.6040 | −2.88 |
| ENSG00000225932.3 | CTAGE4 | 2588 | 0.74 | −3.67 | 2.50 | 0.0139 | 0.6852 | −3.45 |
| ENSG00000050327.14 | ARHGEF5 | 5766 | 0.50 | 2.64 | 2.97 | 0.0036 | 0.5744 | −2.09 |

TABLE 1-continued

| gene_id | gene_name | Length | logFC | AveExpr | t | P. Value | adj. P. Val | B |
|---|---|---|---|---|---|---|---|---|
| ENSG00000179144.4 | GIMAP7 | 1256 | −0.51 | 3.65 | −2.08 | 0.0397 | 0.7817 | −3.71 |
| ENSG00000133574.9 | GIMAP4 | 2102 | −0.53 | 4.81 | −3.01 | 0.0032 | 0.5744 | −1.80 |
| ENSG00000196329.10 | GIMAP5 | 2291 | −0.68 | 4.47 | −3.74 | 0.0003 | 0.3351 | 0.18 |
| ENSG00000157927.16 | RADIL | 3689 | 0.84 | 2.31 | 2.67 | 0.0087 | 0.6320 | −2.74 |
| ENSG00000146530.11 | VWDE | 5297 | 0.77 | 4.55 | 2.45 | 0.0155 | 0.6941 | −3.06 |
| ENSG00000171243.7 | SOSTDC1 | 2473 | 1.35 | 1.91 | 2.60 | 0.0103 | 0.6529 | −2.91 |
| ENSG00000183742.12 | MACC1 | 9159 | 0.55 | 5.83 | 2.29 | 0.0237 | 0.7255 | −3.46 |
| ENSG00000106004.4 | HOXA5 | 1657 | 0.68 | 1.46 | 2.04 | 0.0435 | 0.7905 | −3.78 |
| ENSG00000106006.6 | HOXA6 | 989 | 0.86 | 1.29 | 2.25 | 0.0264 | 0.7312 | −3.52 |
| ENSG00000106633.15 | GCK | 3067 | −0.84 | −3.85 | −2.15 | 0.0331 | 0.7570 | −3.82 |
| ENSG00000106078.17 | COBL | 9090 | 0.53 | 6.62 | 2.00 | 0.0473 | 0.8040 | −4.05 |
| ENSG00000152926.14 | ZNF117 | 9083 | 0.52 | 5.78 | 2.33 | 0.0212 | 0.7189 | −3.37 |
| ENSG00000196275.13 | GTF2IRD2 | 4215 | 0.59 | −2.47 | 2.24 | 0.0267 | 0.7312 | −3.69 |
| ENSG00000186472.19 | PCLO | 5400 | 0.77 | 5.39 | 2.92 | 0.0041 | 0.5940 | −2.02 |
| ENSG00000240720.7 | LRRD1 | 4373 | 0.75 | 0.63 | 2.19 | 0.0307 | 0.7404 | −3.65 |
| ENSG00000106327.12 | TFR2 | 3135 | 0.71 | 2.59 | 2.48 | 0.0145 | 0.6852 | −3.04 |
| ENSG00000077080.9 | ACTL6B | 1537 | 0.86 | −0.58 | 2.32 | 0.0220 | 0.7255 | −3.55 |
| ENSG00000128564.6 | VGF | 2575 | 0.93 | 0.79 | 2.74 | 0.0070 | 0.6271 | −2.85 |
| ENSG00000185055.10 | EFCAB10 | 2242 | 0.52 | 1.23 | 2.02 | 0.0453 | 0.7985 | −3.82 |
| ENSG00000243896.3 | OR2A7 | 1116 | 0.89 | −0.21 | 3.53 | 0.0006 | 0.4557 | −1.71 |
| ENSG00000204947.8 | ZNF425 | 3220 | 0.54 | 2.23 | 2.30 | 0.0234 | 0.7255 | −3.37 |
| ENSG00000130675.14 | MNX1 | 2743 | 0.99 | 0.87 | 2.10 | 0.0380 | 0.7787 | −3.74 |
| ENSG00000158815.10 | FGF17 | 1742 | 0.79 | −1.64 | 2.04 | 0.0433 | 0.7905 | −3.89 |
| ENSG00000134028.14 | ADAMDEC1 | 2348 | −0.70 | 3.33 | −2.07 | 0.0402 | 0.7844 | −3.71 |
| ENSG00000168081.8 | PNOC | 1341 | −0.79 | −1.30 | −2.04 | 0.0434 | 0.7905 | −3.88 |
| ENSG00000131203.12 | IDO1 | 2097 | −0.93 | 4.49 | −2.64 | 0.0093 | 0.6449 | −2.66 |
| ENSG00000164879.6 | CA3 | 1753 | 0.85 | 0.96 | 2.47 | 0.0150 | 0.6852 | −3.24 |
| ENSG00000123119.11 | NECAB1 | 5553 | 0.61 | 0.95 | 2.19 | 0.0303 | 0.7404 | −3.62 |
| ENSG00000164920.9 | OSR2 | 2393 | 0.63 | 3.97 | 2.85 | 0.0051 | 0.6040 | −2.18 |
| ENSG00000181790.10 | ADGRB1 | 5527 | −0.87 | 3.17 | −2.40 | 0.0177 | 0.6941 | −3.13 |
| ENSG00000036565.14 | SLC18A1 | 2957 | −0.78 | −3.29 | −2.04 | 0.0430 | 0.7905 | −3.92 |
| ENSG00000168453.14 | HR | 6336 | 0.61 | 5.06 | 2.26 | 0.0257 | 0.7312 | −3.49 |
| ENSG00000120885.19 | CLU | 3366 | −0.63 | 6.88 | −2.11 | 0.0368 | 0.7787 | −3.86 |
| ENSG00000189233.11 | NUGGC | 3887 | −1.21 | 1.78 | −3.83 | 0.0002 | 0.3351 | −0.49 |
| ENSG00000196166.3 | C8orf86 | 2250 | 0.95 | −3.25 | 2.41 | 0.0176 | 0.6941 | −3.53 |
| ENSG00000165061.14 | ZMAT4 | 2478 | 1.13 | −2.90 | 2.46 | 0.0154 | 0.6930 | −3.46 |
| ENSG00000034239.10 | EFCAB1 | 3750 | 0.88 | −1.37 | 2.09 | 0.0386 | 0.7787 | −3.83 |
| ENSG00000181195.10 | PENK | 2102 | 0.99 | −2.84 | 2.11 | 0.0372 | 0.7787 | −3.85 |
| ENSG00000175946.8 | KLHL38 | 1982 | 0.87 | 1.04 | 2.04 | 0.0432 | 0.7905 | −3.80 |
| ENSG00000122735.15 | DNAI1 | 2599 | 1.10 | 0.93 | 2.73 | 0.0073 | 0.6271 | −2.85 |
| ENSG00000167157.10 | PRRX2 | 1311 | 0.53 | 2.01 | 2.14 | 0.0345 | 0.7629 | −3.62 |
| ENSG00000188523.8 | C9orf171 | 2147 | 0.73 | −2.00 | 2.00 | 0.0479 | 0.8040 | −3.94 |
| ENSG00000123454.10 | DBH | 2763 | −0.99 | 0.32 | −2.78 | 0.0062 | 0.6206 | −2.84 |
| ENSG00000107317.11 | PTGDS | 807 | −0.62 | 3.31 | −2.32 | 0.0219 | 0.7254 | −3.28 |
| ENSG00000170122.5 | FOXD4 | 1974 | 0.66 | −3.12 | 2.23 | 0.0273 | 0.7345 | −3.72 |
| ENSG00000177047.6 | IFNW1 | 1932 | 0.78 | −4.03 | 2.25 | 0.0264 | 0.7312 | −3.73 |
| ENSG00000205143.2 | ARID3C | 1411 | 1.33 | −0.36 | 3.18 | 0.0019 | 0.5544 | −2.31 |
| ENSG00000168828.5 | OR13J1 | 1339 | 1.00 | −1.59 | 2.16 | 0.0323 | 0.7524 | −3.76 |
| ENSG00000106714.17 | CNTNAP3 | 7056 | 1.01 | −0.92 | 3.05 | 0.0028 | 0.5744 | −2.57 |
| ENSG00000154529.14 | CNTNAP3B | 9895 | 0.97 | −2.35 | 2.93 | 0.0041 | 0.5940 | −2.84 |
| ENSG00000107282.7 | APBA1 | 6534 | 0.54 | 3.84 | 2.02 | 0.0459 | 0.7986 | −3.83 |
| ENSG00000148082.9 | SHC3 | 9929 | 0.65 | 1.92 | 2.39 | 0.0183 | 0.7067 | −3.25 |
| ENSG00000165140.9 | FBP1 | 1668 | −1.02 | 2.81 | −3.36 | 0.0010 | 0.5186 | −1.20 |
| ENSG00000188483.7 | IER5L | 2711 | 0.58 | 4.28 | 2.46 | 0.0152 | 0.6904 | −3.03 |
| ENSG00000196990.8 | FAM163B | 1353 | −0.89 | −3.84 | −2.09 | 0.0387 | 0.7787 | −3.88 |
| ENSG00000228570.7 | NUTM2E | 3292 | 0.87 | −3.89 | 2.35 | 0.0206 | 0.7175 | −3.62 |
| ENSG00000204021.3 | LIPK | 1230 | 0.96 | −1.09 | 2.40 | 0.0180 | 0.7005 | −3.47 |
| ENSG00000173239.13 | LIPM | 1511 | −1.01 | −0.56 | −2.39 | 0.0185 | 0.7082 | −3.46 |
| ENSG00000095596.11 | CYP26A1 | 2245 | 1.06 | −1.33 | 2.07 | 0.0403 | 0.7844 | −3.85 |
| ENSG00000119946.10 | CNNM1 | 5959 | 0.96 | 1.06 | 2.11 | 0.0371 | 0.7787 | −3.72 |
| ENSG00000120051.14 | CFAP58 | 3548 | 0.72 | 0.76 | 2.31 | 0.0226 | 0.7255 | −3.48 |
| ENSG00000043591.5 | ADRB1 | 2853 | 1.22 | −0.25 | 2.67 | 0.0086 | 0.6320 | −3.07 |
| ENSG00000134460.15 | IL2RA | 3176 | −0.55 | 3.12 | −2.57 | 0.0113 | 0.6630 | −2.82 |
| ENSG00000204175.5 | GPRIN2 | 1968 | 0.74 | 2.52 | 2.05 | 0.0427 | 0.7905 | −3.74 |
| ENSG00000277758.4 | ABC7-42404400C24.1 | 5526 | 0.82 | 0.71 | 2.43 | 0.0164 | 0.6941 | −3.31 |
| ENSG00000165383.10 | LRRC18 | 1631 | −0.59 | 1.80 | −2.22 | 0.0279 | 0.7392 | −3.51 |
| ENSG00000183230.16 | CTNNA3 | 10762 | 0.74 | −0.11 | 2.05 | 0.0420 | 0.7905 | −3.84 |
| ENSG00000180644.6 | PRF1 | 2534 | −0.91 | 2.94 | −3.46 | 0.0007 | 0.5078 | −0.92 |
| ENSG00000156042.17 | CFAP70 | 3775 | 0.50 | 3.02 | 2.15 | 0.0334 | 0.7586 | −3.57 |
| ENSG00000133661.15 | SFTPD | 1281 | 0.96 | −0.50 | 2.35 | 0.0206 | 0.7175 | −3.51 |
| ENSG00000152766.5 | ANKRD22 | 1596 | −0.62 | 1.71 | −2.06 | 0.0413 | 0.7905 | −3.74 |
| ENSG00000119938.8 | PPP1R3C | 2524 | 0.69 | 1.83 | 2.00 | 0.0472 | 0.8040 | −3.82 |
| ENSG00000155629.14 | PIK3AP1 | 5238 | −0.52 | 5.39 | −3.79 | 0.0002 | 0.3351 | 0.42 |
| ENSG00000172987.12 | HPSE2 | 4421 | 1.18 | −0.99 | 2.53 | 0.0127 | 0.6761 | −3.30 |
| ENSG00000151892.14 | GFRA1 | 9231 | 1.21 | 0.44 | 2.50 | 0.0136 | 0.6850 | −3.24 |
| ENSG00000175018.12 | TEX36 | 922 | −0.71 | −5.38 | −2.08 | 0.0394 | 0.7787 | −3.91 |
| ENSG00000181023.6 | OR56B1 | 975 | −1.02 | 0.94 | −2.48 | 0.0147 | 0.6852 | −3.23 |
| ENSG00000181074.3 | OR52N4 | 1037 | −1.01 | 1.34 | −2.22 | 0.0281 | 0.7392 | −3.55 |

TABLE 1-continued

| gene_id | gene_name | Length | logFC | AveExpr | t | P. Value | adj. P. Val | B |
|---|---|---|---|---|---|---|---|---|
| ENSG00000180988.2 | OR52N2 | 1035 | −1.45 | −1.79 | −2.41 | 0.0175 | 0.6941 | −3.48 |
| ENSG00000180974.3 | OR52E4 | 1030 | −1.60 | −2.94 | −2.49 | 0.0140 | 0.6852 | −3.42 |
| ENSG00000152270.8 | PDE3B | 6076 | −0.60 | 5.08 | −2.80 | 0.0059 | 0.6146 | −2.31 |
| ENSG00000187398.11 | LUZP2 | 5109 | 0.87 | −2.41 | 2.09 | 0.0387 | 0.7787 | −3.85 |
| ENSG00000242689.2 | CNTF | 1894 | 0.64 | 1.36 | 2.02 | 0.0458 | 0.7985 | −3.82 |
| ENSG00000166840.13 | GLYATL1 | 2339 | 0.93 | 1.02 | 2.32 | 0.0220 | 0.7255 | −3.44 |
| ENSG00000110042.7 | DTX4 | 5701 | 0.51 | 5.03 | 2.29 | 0.0236 | 0.7255 | −3.42 |
| ENSG00000162174.12 | ASRGL1 | 2239 | −0.82 | 1.71 | −2.74 | 0.0070 | 0.6271 | −2.70 |
| ENSG00000149021.6 | SCGB1A1 | 582 | 0.85 | −3.14 | 2.26 | 0.0259 | 0.7312 | −3.70 |
| ENSG00000162188.5 | GNG3 | 882 | 0.53 | 1.93 | 2.21 | 0.0290 | 0.7392 | −3.53 |
| ENSG00000133321.10 | RARRES3 | 1271 | −0.58 | 3.95 | −2.52 | 0.0130 | 0.6761 | −2.90 |
| ENSG00000172818.9 | OVOL1 | 3356 | 0.78 | 2.55 | 1.99 | 0.0493 | 0.8108 | −3.83 |
| ENSG00000172543.7 | CTSW | 1383 | −0.55 | 3.46 | −2.51 | 0.0133 | 0.6762 | −2.92 |
| ENSG00000244411.3 | KRTAP5-7 | 1408 | 1.04 | −0.24 | 2.74 | 0.0070 | 0.6271 | −2.96 |
| ENSG00000137474.19 | MYO7A | 7832 | −0.78 | 4.75 | −3.76 | 0.0003 | 0.3351 | 0.29 |
| ENSG00000023445.13 | BIRC3 | 4356 | −0.79 | 6.35 | −3.32 | 0.0012 | 0.5186 | −0.98 |
| ENSG00000198851.9 | CD3E | 1548 | −1.02 | 3.57 | −3.84 | 0.0002 | 0.3351 | 0.29 |
| ENSG00000160654.9 | CD3G | 2690 | −0.86 | 0.71 | −2.56 | 0.0115 | 0.6630 | −3.12 |
| ENSG00000172425.10 | TTC36 | 874 | 0.78 | −0.87 | 2.29 | 0.0235 | 0.7255 | −3.59 |
| ENSG00000137709.9 | POU2F3 | 3081 | 0.78 | 2.02 | 2.41 | 0.0176 | 0.6941 | −3.22 |
| ENSG00000197309.2 | OR10D3 | 1030 | −1.24 | −5.08 | −2.56 | 0.0116 | 0.6630 | −3.41 |
| ENSG00000197849.5 | OR8G1 | 936 | −1.10 | −5.53 | −2.69 | 0.0081 | 0.6271 | −3.27 |
| ENSG00000255298.2 | OR8G5 | 1041 | −1.06 | −5.36 | −2.63 | 0.0096 | 0.6449 | −3.34 |
| ENSG00000181009.4 | OR52N5 | 1034 | −1.25 | −2.35 | −2.13 | 0.0353 | 0.7683 | −3.81 |
| ENSG00000181001.1 | OR52N1 | 963 | −1.33 | −0.57 | −2.45 | 0.0158 | 0.6941 | −3.38 |
| ENSG00000205409.3 | OR52E6 | 982 | −1.35 | −3.24 | −2.13 | 0.0348 | 0.7649 | −3.82 |
| ENSG00000183269.5 | OR52E8 | 1061 | −1.21 | −3.28 | −1.98 | 0.0495 | 0.8108 | −3.97 |
| ENSG00000148948.7 | LRRC4C | 4210 | 0.94 | 1.18 | 2.43 | 0.0166 | 0.6941 | −3.27 |
| ENSG00000156587.15 | UBE2L6 | 1796 | −0.72 | 5.39 | −3.75 | 0.0003 | 0.3351 | 0.28 |
| ENSG00000168070.11 | C11orf85 | 1273 | 0.93 | −0.93 | 2.21 | 0.0288 | 0.7392 | −3.69 |
| ENSG00000175592.8 | FOSL1 | 1840 | 0.65 | 2.95 | 2.25 | 0.0259 | 0.7312 | −3.40 |
| ENSG00000132744.7 | ACY3 | 1300 | −0.91 | −0.63 | −2.06 | 0.0415 | 0.7905 | −3.84 |
| ENSG00000149243.15 | KLHL35 | 1938 | 0.51 | 2.83 | 2.47 | 0.0150 | 0.6852 | −3.04 |
| ENSG00000178795.9 | GDPD4 | 2533 | −0.98 | −0.61 | −2.62 | 0.0098 | 0.6449 | −3.15 |
| ENSG00000204397.7 | CARD16 | 834 | −0.54 | 1.94 | −2.18 | 0.0311 | 0.7404 | −3.57 |
| ENSG00000110777.11 | POU2AF1 | 3295 | −1.14 | 3.19 | −3.08 | 0.0026 | 0.5744 | −1.76 |
| ENSG00000160593.17 | AMICA1 | 2404 | −0.56 | 3.42 | −2.70 | 0.0079 | 0.6271 | −2.55 |
| ENSG00000167286.9 | CD3D | 861 | −1.18 | 1.96 | −3.80 | 0.0002 | 0.3351 | −0.49 |
| ENSG00000196341.2 | OR8D1 | 1026 | −0.82 | −5.32 | −2.09 | 0.0383 | 0.7787 | −3.90 |
| ENSG00000197263.3 | OR8D2 | 936 | −1.15 | −4.73 | −2.38 | 0.0191 | 0.7134 | −3.61 |
| ENSG00000139044.10 | B4GALNT3 | 5068 | 0.63 | 5.19 | 2.03 | 0.0443 | 0.7916 | −3.92 |
| ENSG00000172322.13 | CLEC12A | 2302 | −0.79 | 1.38 | −2.65 | 0.0091 | 0.6425 | −2.90 |
| ENSG00000134539.16 | KLRD1 | 15713 | −0.90 | 1.77 | −3.15 | 0.0021 | 0.5544 | −1.95 |
| ENSG00000134538.2 | SLCO1B1 | 2229 | −1.23 | −2.76 | −2.05 | 0.0424 | 0.7905 | −3.90 |
| ENSG00000090382.6 | LYZ | 1764 | −0.85 | 5.78 | −3.31 | 0.0012 | 0.5186 | −1.01 |
| ENSG00000122971.8 | ACADS | 2090 | 0.51 | 2.45 | 2.15 | 0.0337 | 0.7586 | −3.59 |
| ENSG00000111254.7 | AKAP3 | 3340 | 1.00 | 1.77 | 2.72 | 0.0074 | 0.6271 | −2.73 |
| ENSG00000111644.7 | ACRBP | 2015 | 0.54 | 2.22 | 2.06 | 0.0412 | 0.7905 | −3.72 |
| ENSG00000177575.12 | CD163 | 4388 | −0.59 | 6.86 | −3.26 | 0.0014 | 0.5292 | −1.14 |
| ENSG00000171847.10 | FAM90A1 | 2342 | 0.82 | −1.53 | 2.25 | 0.0259 | 0.7312 | −3.65 |
| ENSG00000166523.7 | CLEC4E | 2234 | −1.10 | 0.04 | −3.00 | 0.0032 | 0.5744 | −2.53 |
| ENSG00000110848.8 | CD69 | 2124 | −0.77 | 2.35 | −2.63 | 0.0095 | 0.6449 | −2.79 |
| ENSG00000213809.8 | KLRK1 | 1553 | −0.61 | 3.29 | −2.39 | 0.0186 | 0.7082 | −3.16 |
| ENSG00000183542.5 | KLRC4 | 930 | −0.88 | −0.40 | −2.48 | 0.0146 | 0.6852 | −3.34 |
| ENSG00000205810.8 | KLRC3 | 1148 | −1.33 | 0.29 | −3.62 | 0.0004 | 0.3749 | −1.42 |
| ENSG00000205809.9 | KLRC2 | 1401 | −1.14 | −1.76 | −2.70 | 0.0079 | 0.6271 | −3.11 |
| ENSG00000134545.13 | KLRC1 | 1798 | −0.83 | −0.56 | −2.13 | 0.0350 | 0.7649 | −3.76 |
| ENSG00000173208.3 | ABCD2 | 6238 | −0.67 | 2.22 | −2.34 | 0.0209 | 0.7175 | −3.30 |
| ENSG00000169884.13 | WNT10B | 2274 | −0.78 | 0.10 | −2.49 | 0.0141 | 0.6852 | −3.29 |
| ENSG00000170465.9 | KRT6C | 2289 | 0.94 | −3.42 | 2.24 | 0.0271 | 0.7330 | −3.72 |
| ENSG00000170374.5 | SP7 | 3151 | −0.74 | −2.44 | −1.99 | 0.0493 | 0.8108 | −3.96 |
| ENSG00000135426.14 | TESPA1 | 4484 | −0.69 | 3.15 | −2.22 | 0.0281 | 0.7392 | −3.45 |
| ENSG00000198673.10 | FAM19A2 | 4208 | 0.75 | −2.29 | 2.17 | 0.0316 | 0.7434 | −3.76 |
| ENSG00000135678.11 | CPM | 6699 | −0.62 | 4.72 | −3.18 | 0.0019 | 0.5544 | −1.37 |
| ENSG00000185046.18 | ANKS1B | 7446 | 0.55 | 4.87 | 2.86 | 0.0049 | 0.6023 | −2.16 |
| ENSG00000172458.4 | IL17D | 1861 | 0.97 | −0.60 | 2.73 | 0.0073 | 0.6271 | −3.01 |
| ENSG00000132932.16 | ATP8A2 | 9662 | 0.89 | 0.06 | 2.35 | 0.0201 | 0.7175 | −3.47 |
| ENSG00000132970.12 | WASF3 | 5004 | 0.59 | 4.26 | 2.69 | 0.0081 | 0.6271 | −2.54 |
| ENSG00000185352.8 | HS6ST3 | 7806 | 1.26 | −0.92 | 2.60 | 0.0105 | 0.6577 | −3.21 |
| ENSG00000132975.7 | GPR12 | 1981 | 1.30 | −0.06 | 2.12 | 0.0361 | 0.7726 | −3.76 |
| ENSG00000122025.14 | FLT3 | 3842 | −0.70 | 1.91 | −2.62 | 0.0100 | 0.6498 | −2.88 |
| ENSG00000136167.13 | LCP1 | 4043 | −0.60 | 6.77 | −3.24 | 0.0015 | 0.5292 | −1.20 |
| ENSG00000102547.18 | CAB39L | 3940 | 0.59 | 2.93 | 2.47 | 0.0149 | 0.6852 | −3.03 |
| ENSG00000280165.1 | PCDH20 | 4778 | 1.24 | −0.61 | 2.41 | 0.0176 | 0.6941 | −3.44 |
| ENSG00000215277.8 | RNF212B | 903 | 0.65 | 2.73 | 2.23 | 0.0273 | 0.7345 | −3.44 |
| ENSG00000166090.8 | IL25 | 1367 | −0.97 | −4.97 | −2.76 | 0.0066 | 0.6235 | −3.17 |
| ENSG00000139914.6 | FITM1 | 1355 | 0.79 | −0.37 | 1.99 | 0.0482 | 0.8058 | −3.91 |
| ENSG00000184227.7 | ACOT1 | 1713 | 0.88 | −2.99 | 2.03 | 0.0440 | 0.7916 | −3.92 |

TABLE 1-continued

| gene_id | gene_name | Length | logFC | AveExpr | t | P. Value | adj. P. Val | B |
|---|---|---|---|---|---|---|---|---|
| ENSG00000140057.8 | AK7 | 4329 | 0.89 | −0.99 | 2.24 | 0.0269 | 0.7330 | −3.66 |
| ENSG00000036530.8 | CYP46A1 | 2259 | 0.73 | −0.18 | 2.21 | 0.0286 | 0.7392 | −3.65 |
| ENSG00000179627.9 | ZBTB42 | 1411 | 0.64 | 2.85 | 2.34 | 0.0209 | 0.7175 | −3.26 |
| ENSG00000131979.18 | GCH1 | 2951 | −0.51 | 4.24 | −2.73 | 0.0072 | 0.6271 | −2.45 |
| ENSG00000070182.17 | SPTB | 10483 | 0.65 | 2.47 | 2.14 | 0.0341 | 0.7586 | −3.60 |
| ENSG00000165555.9 | NOXRED1 | 1857 | 0.56 | 1.32 | 2.12 | 0.0363 | 0.7731 | −3.69 |
| ENSG00000140093.9 | SERPINA10 | 5467 | 1.31 | −2.40 | 2.63 | 0.0097 | 0.6449 | −3.24 |
| ENSG00000186910.3 | SERPINA11 | 1476 | 1.04 | −3.90 | 2.44 | 0.0160 | 0.6941 | −3.51 |
| ENSG00000165953.9 | SERPINA12 | 2061 | 1.02 | −2.61 | 2.03 | 0.0441 | 0.7916 | −3.91 |
| ENSG00000168350.7 | DEGS2 | 4352 | 0.76 | 1.70 | 2.36 | 0.0199 | 0.7167 | −3.32 |
| ENSG00000237289.9 | CKMT1B | 1986 | 1.28 | 0.24 | 2.56 | 0.0115 | 0.6630 | −3.17 |
| ENSG00000223572.9 | CKMT1A | 1802 | 1.17 | −0.21 | 2.57 | 0.0113 | 0.6630 | −3.20 |
| ENSG00000140284.10 | SLC27A2 | 2746 | −0.76 | 0.62 | −2.06 | 0.0416 | 0.7905 | −3.80 |
| ENSG00000182950.2 | ODF3L1 | 1196 | 0.80 | 0.32 | 2.12 | 0.0358 | 0.7714 | −3.74 |
| ENSG00000183476.12 | SH2D7 | 2750 | 0.78 | −1.18 | 2.14 | 0.0340 | 0.7586 | −3.77 |
| ENSG00000169684.13 | CHRNA5 | 3623 | −0.61 | 2.87 | −2.22 | 0.0285 | 0.7392 | −3.47 |
| ENSG00000235711.4 | ANKRD34C | 4951 | 0.92 | −4.74 | 2.38 | 0.0186 | 0.7082 | −3.60 |
| ENSG00000156222.11 | SLC28A1 | 3445 | 1.13 | 0.85 | 2.64 | 0.0094 | 0.6449 | −3.00 |
| ENSG00000140527.14 | WDR93 | 3745 | 0.74 | 2.64 | 2.50 | 0.0136 | 0.6850 | −2.99 |
| ENSG00000140443.13 | IGF1R | 11803 | 0.52 | 7.34 | 2.81 | 0.0057 | 0.6040 | −2.33 |
| ENSG00000175265.17 | GOLGA8A | 4810 | 0.51 | 2.11 | 2.46 | 0.0152 | 0.6904 | −3.12 |
| ENSG00000140279.12 | DUOX2 | 6537 | 0.77 | 1.92 | 2.07 | 0.0404 | 0.7844 | −3.72 |
| ENSG00000137875.4 | BCL2L10 | 1319 | 0.81 | −1.58 | 2.08 | 0.0392 | 0.7787 | −3.84 |
| ENSG00000205502.3 | C2CD4B | 1579 | 0.94 | −1.40 | 2.07 | 0.0405 | 0.7846 | −3.85 |
| ENSG00000175318.11 | GRAMD2 | 3281 | 0.92 | 3.15 | 2.82 | 0.0056 | 0.6040 | −2.33 |
| ENSG00000103740.9 | ACSBG1 | 6777 | 0.75 | −0.23 | 2.08 | 0.0395 | 0.7787 | −3.81 |
| ENSG00000140543.13 | DET1 | 2337 | 0.55 | 3.97 | 2.67 | 0.0086 | 0.6320 | −2.59 |
| ENSG00000183971.5 | NPW | 1016 | 0.93 | −1.53 | 2.57 | 0.0115 | 0.6630 | −3.28 |
| ENSG00000008517.16 | IL32 | 1524 | −0.53 | 5.20 | −2.34 | 0.0209 | 0.7175 | −3.33 |
| ENSG00000228146.6 | CASP16 | 1433 | 0.67 | 1.67 | 2.18 | 0.0314 | 0.7411 | −3.59 |
| ENSG00000175267.14 | VWA3A | 4672 | 0.71 | 0.14 | 2.06 | 0.0418 | 0.7905 | −3.82 |
| ENSG00000166501.12 | PRKCB | 8205 | −0.62 | 3.98 | −2.25 | 0.0261 | 0.7312 | −3.43 |
| ENSG00000005844.17 | ITGAL | 5213 | −0.65 | 5.19 | −3.00 | 0.0033 | 0.5744 | −1.82 |
| ENSG00000156886.11 | ITGAD | 3912 | −0.63 | 1.86 | −2.18 | 0.0309 | 0.7404 | −3.57 |
| ENSG00000159618.15 | ADGRG5 | 3932 | −0.74 | 1.58 | −2.08 | 0.0391 | 0.7787 | −3.72 |
| ENSG00000257017.8 | HP | 1828 | 0.69 | 1.62 | 2.28 | 0.0242 | 0.7256 | −3.44 |
| ENSG00000261701.6 | HPR | 1244 | 0.76 | 1.94 | 2.27 | 0.0252 | 0.7312 | −3.44 |
| ENSG00000154099.17 | DNAAF1 | 2379 | 0.84 | 0.64 | 2.68 | 0.0085 | 0.6309 | −2.97 |
| ENSG00000103175.10 | WFDC1 | 1911 | 1.14 | −0.06 | 2.85 | 0.0051 | 0.6040 | −2.79 |
| ENSG00000225614.2 | ZNF469 | 13287 | 0.61 | 8.32 | 2.62 | 0.0098 | 0.6449 | −2.81 |
| ENSG00000167523.13 | SPATA33 | 3448 | 0.61 | 1.80 | 2.38 | 0.0190 | 0.7134 | −3.29 |
| ENSG00000162006.9 | MSLNL | 2109 | 1.46 | 1.11 | 2.47 | 0.0148 | 0.6852 | −3.22 |
| ENSG00000167971.15 | CASKIN1 | 5759 | 0.65 | 2.71 | 2.30 | 0.0231 | 0.7255 | −3.34 |
| ENSG00000172382.9 | PRSS27 | 1130 | 0.57 | 2.48 | 2.17 | 0.0323 | 0.7524 | −3.56 |
| ENSG00000185338.4 | SOCS1 | 1225 | −0.78 | 1.72 | −2.32 | 0.0217 | 0.7235 | −3.37 |
| ENSG00000102886.14 | GDPD3 | 1397 | 0.51 | 2.74 | 2.15 | 0.0335 | 0.7586 | −3.58 |
| ENSG00000099365.9 | STX1B | 4892 | 0.51 | 1.40 | 2.08 | 0.0393 | 0.7787 | −3.73 |
| ENSG00000176723.9 | ZNF843 | 4564 | 0.78 | −0.25 | 2.29 | 0.0237 | 0.7255 | −3.57 |
| ENSG00000103023.11 | PRSS54 | 1810 | 0.90 | −2.80 | 2.19 | 0.0307 | 0.7404 | −3.76 |
| ENSG00000154102.10 | C16orf74 | 1616 | 1.04 | −0.48 | 2.78 | 0.0062 | 0.6206 | −2.92 |
| ENSG00000262664.2 | OVCA2 | 1122 | 0.73 | −0.11 | 2.52 | 0.0130 | 0.6761 | −3.26 |
| ENSG00000167720.12 | SRR | 2728 | 0.53 | 3.07 | 2.16 | 0.0326 | 0.7536 | −3.56 |
| ENSG00000182327.7 | GLTPD2 | 1023 | 0.92 | 1.01 | 2.60 | 0.0104 | 0.6537 | −3.03 |
| ENSG00000108515.17 | ENO3 | 1521 | 0.57 | 2.35 | 2.18 | 0.0308 | 0.7404 | −3.54 |
| ENSG00000183914.14 | DNAH2 | 15960 | 0.92 | 4.91 | 2.85 | 0.0051 | 0.6040 | −2.19 |
| ENSG00000188803.14 | SHISA6 | 7575 | 0.86 | −0.06 | 1.99 | 0.0490 | 0.8106 | −3.91 |
| ENSG00000275302.1 | CCL4 | 904 | −0.69 | −0.63 | −2.20 | 0.0297 | 0.7398 | −3.69 |
| ENSG00000141744.3 | PNMT | 1457 | 0.94 | −1.37 | 2.75 | 0.0069 | 0.6271 | −3.03 |
| ENSG00000073861.2 | TBX21 | 2572 | −0.81 | 1.66 | −2.14 | 0.0346 | 0.7637 | −3.64 |
| ENSG00000075461.5 | CACNG4 | 3380 | 0.98 | 3.09 | 2.18 | 0.0312 | 0.7404 | −3.53 |
| ENSG00000108984.13 | MAP2K6 | 3127 | −0.51 | 3.16 | −2.61 | 0.0100 | 0.6498 | −2.73 |
| ENSG00000083454.21 | P2RX5 | 2812 | −0.77 | 2.80 | −3.02 | 0.0030 | 0.5744 | −1.95 |
| ENSG00000129194.7 | SOX15 | 1541 | 0.93 | 0.71 | 2.55 | 0.0121 | 0.6648 | −3.15 |
| ENSG00000240505.8 | TNFRSF13B | 1499 | −0.89 | −1.03 | −2.76 | 0.0066 | 0.6235 | −2.99 |
| ENSG00000232859.9 | LYRM9 | 807 | 0.78 | 0.03 | 3.24 | 0.0015 | 0.5292 | −2.17 |
| ENSG00000109107.13 | ALDOC | 1982 | 0.54 | 3.27 | 2.14 | 0.0347 | 0.7649 | −3.60 |
| ENSG00000205045.8 | SLFN12L | 2766 | −0.52 | 4.61 | −2.37 | 0.0195 | 0.7143 | −3.24 |
| ENSG00000271503.5 | CCL5 | 1365 | −0.62 | 4.81 | −2.41 | 0.0176 | 0.6941 | −3.17 |
| ENSG00000274736.4 | CCL23 | 626 | −0.90 | −4.22 | −2.43 | 0.0167 | 0.6941 | −3.54 |
| ENSG00000277363.4 | SRCIN1 | 7058 | 0.55 | 3.97 | 2.13 | 0.0354 | 0.7686 | −3.65 |
| ENSG00000161405.16 | IKZF3 | 10008 | −1.10 | 4.72 | −4.69 | 0.0000 | 0.1263 | 3.29 |
| ENSG00000186847.5 | KRT14 | 1662 | 1.19 | 2.68 | 2.10 | 0.0378 | 0.7787 | −3.66 |
| ENSG00000267060.5 | PTGES3L | 1781 | 0.53 | 0.96 | 2.08 | 0.0395 | 0.7787 | −3.76 |
| ENSG00000141293.15 | SKAP1 | 1534 | −0.90 | 2.96 | −3.79 | 0.0002 | 0.3351 | −0.06 |
| ENSG00000007312.12 | CD79B | 1272 | −0.89 | 0.54 | −2.45 | 0.0157 | 0.6941 | −3.30 |
| ENSG00000173762.7 | CD7 | 2478 | −0.86 | 1.64 | −2.83 | 0.0054 | 0.6040 | −2.56 |
| ENSG00000197632.8 | SERPINB2 | 2171 | 1.70 | −0.53 | 2.97 | 0.0036 | 0.5744 | −2.65 |
| ENSG00000134765.9 | DSC1 | 4271 | 0.81 | 0.62 | 2.27 | 0.0247 | 0.7298 | −3.53 |

TABLE 1-continued

| gene_id | gene_name | Length | logFC | AveExpr | t | P. Value | adj. P. Val | B |
|---|---|---|---|---|---|---|---|---|
| ENSG00000206181.5 | TCEB3B | 3050 | 0.50 | 1.96 | 1.98 | 0.0495 | 0.8108 | −3.84 |
| ENSG00000184828.9 | ZBTB7C | 5383 | 1.03 | 2.62 | 2.87 | 0.0048 | 0.6023 | −2.30 |
| ENSG00000172232.9 | AZU1 | 1783 | 1.03 | −2.02 | 2.21 | 0.0287 | 0.7392 | −3.71 |
| ENSG00000104953.18 | TLE6 | 2334 | 0.88 | 0.25 | 2.04 | 0.0434 | 0.7905 | −3.84 |
| ENSG00000130377.13 | ACSBG2 | 2778 | 0.73 | 2.03 | 2.69 | 0.0082 | 0.6271 | −2.74 |
| ENSG00000130173.13 | C19orf80 | 1223 | 0.78 | 1.49 | 2.80 | 0.0060 | 0.6169 | −2.65 |
| ENSG00000141854.7 | CTB-5506.8 | 1600 | 0.54 | 1.87 | 2.00 | 0.0479 | 0.8040 | −3.82 |
| ENSG00000221946.7 | FXYD7 | 823 | 0.79 | 0.93 | 2.10 | 0.0379 | 0.7787 | −3.74 |
| ENSG00000105369.9 | CD79A | 1258 | −0.80 | 1.80 | −2.05 | 0.0427 | 0.7905 | −3.76 |
| ENSG00000188368.9 | PRR19 | 2454 | 1.12 | 1.29 | 3.19 | 0.0018 | 0.5541 | −1.98 |
| ENSG00000124449.6 | IRGC | 1662 | 1.17 | −3.25 | 3.30 | 0.0012 | 0.5186 | −2.37 |
| ENSG00000130208.9 | APOC1 | 841 | −0.67 | 2.48 | −2.55 | 0.0120 | 0.6648 | −2.92 |
| ENSG00000142549.9 | IGLON5 | 2606 | 0.97 | −1.83 | 2.18 | 0.0311 | 0.7404 | −3.74 |
| ENSG00000104970.10 | KIR3DX1 | 3325 | −0.90 | −3.43 | −2.13 | 0.0349 | 0.7649 | −3.83 |
| ENSG00000189430.12 | NCR1 | 1628 | −0.80 | −0.69 | −2.00 | 0.0476 | 0.8040 | −3.91 |
| ENSG00000196263.7 | ZNF471 | 6287 | 0.71 | 3.64 | 2.22 | 0.0282 | 0.7392 | −3.47 |
| ENSG00002268182.5 | SMIM17 | 1076 | 0.73 | 0.14 | 2.26 | 0.0257 | 0.7312 | −3.58 |
| ENSG00000099625.12 | C19orf26 | 4346 | 0.85 | 1.12 | 2.85 | 0.0051 | 0.6040 | −2.62 |
| ENSG00000087903.12 | RFX2 | 3993 | 0.70 | 2.78 | 2.73 | 0.0073 | 0.6271 | −2.56 |
| ENSG00000104883.7 | PEX11G | 1415 | 0.63 | 1.08 | 2.20 | 0.0294 | 0.7392 | −3.59 |
| ENSG00000174667.3 | OR7D4 | 1022 | −0.80 | −5.03 | −2.23 | 0.0273 | 0.7345 | −3.76 |
| ENSG00000198003.11 | CCDC151 | 2217 | 0.96 | −0.71 | 2.21 | 0.0293 | 0.7392 | −3.68 |
| ENSG00000160951.3 | PTGER1 | 1421 | 1.01 | −0.79 | 2.99 | 0.0034 | 0.5744 | −2.65 |
| ENSG00000130518.16 | KIAA1683 | 4442 | 0.58 | 5.24 | 2.04 | 0.0430 | 0.7905 | −3.90 |
| ENSG00000161249.20 | DMKN | 2865 | 1.01 | 3.49 | 2.58 | 0.0112 | 0.6630 | −2.80 |
| ENSG00000189001.10 | SBSN | 1986 | 1.44 | 0.71 | 2.78 | 0.0062 | 0.6206 | −2.79 |
| ENSG00000196381.10 | ZNF781 | 3147 | 0.66 | 0.89 | 2.24 | 0.0267 | 0.7312 | −3.55 |
| ENSG00000160396.8 | HIPK4 | 2452 | 0.83 | −0.46 | 2.30 | 0.0230 | 0.7255 | −3.56 |
| ENSG00000130201.7 | EXOC3L2 | 1725 | 0.62 | 2.34 | 2.76 | 0.0067 | 0.6251 | −2.57 |
| ENSG00000230510.6 | PPP5D1 | 1882 | 0.74 | −1.91 | 2.04 | 0.0430 | 0.7905 | −3.89 |
| ENSG00000142233.11 | NTN5 | 1836 | 0.90 | 0.34 | 2.58 | 0.0111 | 0.6630 | −3.14 |
| ENSG00000196337.10 | CGB7 | 3386 | 0.87 | −0.53 | 2.14 | 0.0345 | 0.7629 | −3.76 |
| ENSG00000105374.9 | NKG7 | 935 | −0.73 | 2.10 | −2.57 | 0.0114 | 0.6630 | −2.94 |
| ENSG00000105366.15 | SIGLEC8 | 2951 | −0.85 | −0.07 | −2.03 | 0.0441 | 0.7916 | −3.86 |
| ENSG00000254415.3 | SIGLEC14 | 2035 | −0.65 | 1.53 | −2.01 | 0.0461 | 0.8003 | −3.81 |
| ENSG00000198300.12 | PEG3 | 8759 | 1.28 | 5.46 | 2.90 | 0.0044 | 0.5942 | −2.06 |
| ENSG00000125780.11 | TGM3 | 2642 | 1.45 | −2.12 | 3.08 | 0.0025 | 0.5744 | −2.61 |
| ENSG00000101331.15 | CCM2L | 2523 | 0.66 | 1.27 | 2.24 | 0.0270 | 0.7330 | −3.53 |
| ENSG00000124203.5 | ZNF831 | 9404 | −0.91 | 4.29 | −3.54 | 0.0006 | 0.4557 | −0.41 |
| ENSG00000089012.14 | SIRPG | 1870 | −0.83 | 0.57 | −2.23 | 0.0275 | 0.7349 | −3.59 |
| ENSG00000125864.11 | BFSP1 | 2874 | 0.63 | 2.17 | 2.47 | 0.0147 | 0.6852 | −3.09 |
| ENSG00000175121.11 | WFDC5 | 1018 | 0.92 | −2.25 | 2.25 | 0.0261 | 0.7312 | −3.68 |
| ENSG00000124256.14 | ZBP1 | 2570 | −0.72 | 3.61 | −2.68 | 0.0084 | 0.6309 | −2.58 |
| ENSG00000198054.11 | DSCR8 | 552 | −1.16 | −5.16 | −2.56 | 0.0118 | 0.6639 | −3.42 |
| ENSG00000188992.11 | LIPI | 1744 | 0.69 | 0.81 | 2.22 | 0.0284 | 0.7392 | −3.59 |
| ENSG00000159261.10 | CLDN14 | 2350 | 0.86 | 0.62 | 2.24 | 0.0266 | 0.7312 | −3.57 |
| ENSG00000171587.14 | DSCAM | 8577 | 0.97 | −1.30 | 2.03 | 0.0444 | 0.7924 | −3.89 |
| ENSG00000221864.4 | KRTAP12-2 | 739 | −0.80 | −4.75 | −2.20 | 0.0299 | 0.7398 | −3.79 |
| ENSG00000099957.16 | P2RX6 | 3687 | 0.80 | −1.35 | 2.12 | 0.0359 | 0.7726 | −3.80 |
| ENSG00000254709.6 | IGLL5 | 2343 | −1.32 | 5.61 | −3.33 | 0.0012 | 0.5186 | −0.95 |
| ENSG00000221963.5 | APOL6 | 10121 | −0.56 | 5.74 | −2.90 | 0.0044 | 0.5942 | −2.08 |
| ENSG00000100342.20 | APOL1 | 3116 | −0.61 | 5.11 | −3.45 | 0.0008 | 0.5084 | −0.62 |
| ENSG00000239713.7 | APOBEC3G | 1851 | −0.55 | 3.49 | −2.56 | 0.0116 | 0.6630 | −2.82 |
| ENSG00000100218.11 | RSPH14 | 1456 | 1.26 | −2.13 | 2.87 | 0.0049 | 0.6023 | −2.91 |
| ENSG00000128242.12 | GAL3ST1 | 1976 | 1.32 | −0.90 | 2.90 | 0.0044 | 0.5942 | −2.78 |
| ENSG00000128284.19 | APOL3 | 3800 | −0.58 | 4.90 | −3.08 | 0.0026 | 0.5744 | −1.62 |
| ENSG00000100336.17 | APOL4 | 3854 | −0.54 | 3.55 | −2.86 | 0.0049 | 0.6023 | −2.18 |
| ENSG00000100385.13 | IL2RB | 4113 | −0.69 | 4.41 | −2.86 | 0.0050 | 0.6023 | −2.15 |
| ENSG00000056487.15 | PHF21B | 3917 | 0.94 | −2.37 | 2.14 | 0.0341 | 0.7586 | −3.80 |
| ENSG00000101916.11 | TLR8 | 4353 | −0.58 | 3.79 | −2.04 | 0.0430 | 0.7905 | −3.78 |
| ENSG00000189186.10 | DCAF8L2 | 2354 | −0.96 | −5.04 | −2.42 | 0.0168 | 0.6941 | −3.56 |
| ENSG00000102053.12 | ZC3H12B | 7256 | 0.52 | 3.29 | 2.18 | 0.0309 | 0.7404 | −3.52 |
| ENSG00000184210.5 | DGAT2L6 | 1553 | 0.84 | −0.46 | 2.33 | 0.0212 | 0.7189 | −3.52 |
| ENSG00000204195.3 | AWAT1 | 1365 | 0.65 | 0.58 | 2.03 | 0.0441 | 0.7916 | −3.83 |
| ENSG00000126733.20 | DACH2 | 2512 | 1.40 | −2.45 | 3.05 | 0.0028 | 0.5744 | −2.68 |
| ENSG00000157502.12 | MUM1L1 | 4343 | 1.57 | 0.05 | 3.11 | 0.0023 | 0.5744 | −2.36 |
| ENSG00000183918.14 | SH2D1A | 2450 | −0.86 | 1.23 | −2.35 | 0.0203 | 0.7175 | −3.38 |
| ENSG00000165509.13 | MAGEC3 | 2763 | 1.45 | −1.51 | 2.99 | 0.0034 | 0.5744 | −2.71 |
| ENSG00000198681.6 | MAGEA1 | 1710 | −0.99 | −5.44 | −2.52 | 0.0130 | 0.6761 | −3.47 |
| ENSG00000147003.5 | TMEM27 | 1578 | 0.66 | 0.47 | 2.09 | 0.0382 | 0.7787 | −3.77 |
| ENSG00000132446.6 | FTHL17 | 813 | −1.13 | −4.52 | −2.05 | 0.0426 | 0.7905 | −3.93 |
| ENSG00000102096.9 | PIM2 | 2075 | −0.65 | 5.30 | −2.82 | 0.0055 | 0.6040 | −2.26 |
| ENSG00000165349.11 | SLC7A3 | 2265 | 1.07 | −3.10 | 2.10 | 0.0379 | 0.7787 | −3.86 |
| ENSG00000147168.12 | IL2RG | 1534 | −0.82 | 4.89 | −3.40 | 0.0009 | 0.5186 | −0.75 |
| ENSG00000186810.7 | CXCR3 | 1868 | −0.61 | 2.98 | −2.29 | 0.0236 | 0.7255 | −3.34 |
| ENSG00000179300.3 | ZCCHC5 | 2648 | 0.91 | −2.45 | 2.26 | 0.0254 | 0.7312 | −3.67 |
| ENSG00000072133.10 | RPS6KA6 | 8258 | 0.86 | 2.78 | 2.38 | 0.0190 | 0.7134 | −3.20 |
| ENSG00000188828.11 | GLRA4 | 1795 | 0.82 | −2.26 | 2.05 | 0.0421 | 0.7905 | −3.89 |

TABLE 1-continued

| gene__id | gene__name | Length | logFC | AveExpr | t | P. Value | adj. P. Val | B |
|---|---|---|---|---|---|---|---|---|
| ENSG00000123570.3 | RAB9B | 3748 | 0.67 | 1.04 | 2.23 | 0.0279 | 0.7386 | −3.57 |
| ENSG00000147223.5 | RIPPLY1 | 1190 | 0.99 | −2.67 | 2.69 | 0.0082 | 0.6271 | −3.18 |
| ENSG00000176076.7 | KCNE5 | 1473 | 1.10 | −2.28 | 2.65 | 0.0091 | 0.6447 | −3.21 |
| ENSG00000009694.13 | TENM1 | 12896 | −0.63 | 4.02 | −2.66 | 0.0089 | 0.6336 | −2.61 |
| ENSG00000046774.9 | MAGEC2 | 1991 | −0.96 | −4.86 | −2.02 | 0.0458 | 0.7985 | −3.97 |
| ENSG00000155961.4 | RAB39B | 3505 | −0.68 | −0.19 | −2.02 | 0.0456 | 0.7985 | −3.88 |
| ENSG00000278817.1 | DGCR6 | 1213 | 0.88 | −2.31 | 2.19 | 0.0301 | 0.7404 | −3.74 |

TABLE 2

Logistic Regression Coefficients

| | Estimate | Std. Error | z value | Pr(>|z|) |
|---|---|---|---|---|
| (Intercept) | 2.2231 | 0.8065 | 2.756 | 0.00584 ** |
| Bcell.gini | −3.012 | 1.1949 | −2.521 | 0.01171 * |
| Tcell.gini | −0.9211 | 1.1548 | −0.798 | 0.42506 |

TABLE 3

Classification Accuracy of Existing Gene Signatures

| | OncotypeDX | | MammaPrint | |
|---|---|---|---|---|
| | mean | sd | mean | sd |
| Xgboost | 0.500 | 0.177 | 0.533 | 0.192 |
| Random forest | 0.475 | 0.165 | 0.525 | 0.184 |
| SVM | 0.500 | 0.170 | 0.550 | 0.162 |

* 15-fold cross validation

TABLE 4

Association of Clinical Covariates with Recurrence

| Clinical variable | Level | Non-Recurrent | Recurrent | p-value (Fisher's test) |
|---|---|---|---|---|
| Lymphocyte response | Low | 13 | 25 | 0.0083 |
| | Intermediate | 21 | 25 | |
| | High | 25 | 11 | |
| EGFR lab result | negative | 15 | 21 | 0.3227 |
| | positive | 44 | 40 | |
| CK56 lab result | negative | 13 | 9 | 0.3507 |
| | positive | 46 | 52 | |
| Ki67 lab result | 0-14% | 4 | 6 | 0.5214 |
| | >14% | 55 | 50 | |
| AJCC group stage | I | 14 | 16 | 0.9721 |
| | II | 25 | 26 | |
| | III | 20 | 19 | |
| Tumor size | <=2 cm | 21 | 20 | 0.8254 |
| | 2.1-5.0 cm | 29 | 29 | |
| | >5.0 cm | 8 | 11 | |
| Lymph node Involvement | no | 29 | 29 | 1.0000 |
| | yes | 30 | 32 | |
| Race | Asian/Pacific Island | 1 | 4 | 0.3204 |
| | black | 2 | 4 | |
| | Hispanic white | 0 | 1 | |
| | white | 56 | 52 | |
| Familial history 1st deg | yes | 11 | 17 | 0.2817 |
| | no | 47 | 43 | |

TABLE 5

Marker Genes Selected by at Least Two Algorithms to Characterize Recurrent and Non-recurrent Cases

| Gene id | Gene name | Frequency of selection | P value (Rec. vs Non Rec.) |
|---|---|---|---|
| ENSG00000075975.15 | MKRN2 | 5 | 0.0100 |
| ENSG00000237441.9 | RGL2 | 5 | 0.0718 |
| ENSG00000113578.17 | FGF1 | 4 | 0.0001 |
| ENSG00000096060.14 | FKBP5 | 4 | 0.0001 |
| ENSG00000205464.11 | ATP6AP1L | 4 | 0.0018 |
| ENSG00000163435.15 | ELF3 | 4 | 0.0058 |
| ENSG00000189430.12 | NCR1 | 4 | 0.0476 |
| ENSG00000162739.13 | SLAMF6 | 3 | 0.0004 |
| ENSG00000157510.13 | AFAP1L1 | 3 | 0.0009 |
| ENSG00000174332.5 | GLIS1 | 3 | 0.0012 |
| ENSG00000136770.10 | DNAJC1 | 3 | 0.0012 |
| ENSG00000196411.9 | EPHB4 | 3 | 0.0016 |
| ENSG00000112697.15 | TMEM30A | 3 | 0.0028 |
| ENSG00000166523.7 | CLEC4E | 3 | 0.0032 |
| ENSG00000164715.5 | LMTK2 | 3 | 0.0077 |
| ENSG00000161217.11 | PCYT1A | 3 | 0.0168 |
| ENSG00000118242.15 | MREG | 3 | 0.0307 |
| ENSG00000113249.12 | HAVCR1 | 3 | 0.0311 |
| ENSG00000111653.19 | ING4 | 3 | 0.0350 |
| ENSG00000161405.16 | IKZF3 | 2 | 0.0000 |
| ENSG00000163568.13 | AIM2 | 2 | 0.0002 |
| ENSG00000162654.8 | GBP4 | 2 | 0.0002 |
| ENSG00000189233.11 | NUGGC | 2 | 0.0002 |
| ENSG00000137474.19 | MYO7A | 2 | 0.0003 |
| ENSG00000156587.15 | UBE2L6 | 2 | 0.0003 |
| ENSG00000070778.12 | PTPN21 | 2 | 0.0007 |
| ENSG00000180644.6 | PRF1 | 2 | 0.0007 |
| ENSG00000197746.13 | PSAP | 2 | 0.0012 |
| ENSG00000163599.14 | CTLA4 | 2 | 0.0012 |
| ENSG00000163794.6 | UCN | 2 | 0.0015 |
| ENSG00000004468.12 | CD38 | 2 | 0.0027 |
| ENSG00000114378.16 | HYAL1 | 2 | 0.0031 |
| ENSG00000169247.11 | SH3TC2 | 2 | 0.0039 |
| ENSG00000100968.13 | NFATC4 | 2 | 0.0055 |
| ENSG00000134109.10 | EDEM1 | 2 | 0.0056 |
| ENSG00000129084.17 | PSMA1 | 2 | 0.0102 |
| ENSG00000140948.11 | ZCCHC14 | 2 | 0.0110 |
| ENSG00000129194.7 | SOX15 | 2 | 0.0121 |
| ENSG00000104660.17 | LEPROTL1 | 2 | 0.0131 |
| ENSG00000167526.13 | RPL13 | 2 | 0.0132 |
| ENSG00000187609.15 | EXD3 | 2 | 0.0134 |
| ENSG00000153975.9 | ZUFSP | 2 | 0.0160 |
| ENSG00000125430.8 | HS3ST3B1 | 2 | 0.0233 |
| ENSG00000165383.10 | LRRC18 | 2 | 0.0279 |
| ENSG00000127980.15 | PEX1 | 2 | 0.0425 |
| ENSG00000146242.8 | TPBG | 2 | 0.0433 |
| ENSG00000065615.13 | CYB5R4 | 2 | 0.0437 |
| ENSG00000261934.2 | PCDHGA9 | 2 | 0.0478 |
| ENSG00000175662.17 | TOM1L2 | 2 | 0.0701 |
| ENSG00000147394.18 | ZNF185 | 2 | 0.0710 |
| ENSG00000162777.16 | DENND2D | 2 | 0.0712 |
| ENSG00000137496.17 | IL18BP | 2 | 0.0909 |
| ENSG00000138303.17 | ASCC1 | 2 | 0.0915 |
| ENSG00000112144.15 | ICK | 2 | 0.0942 |
| ENSG00000075568.16 | TMEM131 | 2 | 0.0975 |

TABLE 6

BRAVO-DX Gene Information

| Gene id | Gene name | Frequency of selection | P value (Rec. vs Non Rec.) | Gene description | Gene type | Marker category | BRAVO-IMMUNE |
|---|---|---|---|---|---|---|---|
| ENSG00000075975.15 | MKRN2 | 5 | 0.0100 | makorin ring finger protein 2 | other | immune | Yes |
| ENSG00000237441.9 | RGL2 | 5 | 0.0718 | ral guanine nucleotide dissociation stimulator like 2 | other | intrinsic | No |
| ENSG00000113578.17 | FGF1 | 4 | 0.0001 | fibroblast growth factor 1 | growth factor | intrinsic | No |
| ENSG00000096060.14 | FKBP5 | 4 | 0.0001 | FK506 binding protein 5 | enzyme | immune | Yes |
| ENSG00000205464.11 | ATP6AP1L | 4 | 0.0018 | ATPase H+ transporting accessory protein 1 like | other | intrinsic | No |
| ENSG00000163435.15 | ELF3 | 4 | 0.0058 | E74 like ETS transcription factor 3 | transcription regulator | intrinsic | No |
| ENSG00000189430.12 | NCR1 | 4 | 0.0476 | natural cytotoxicity triggering receptor 1 | transmembrane receptor | immune | Yes |
| ENSG00000162739.13 | SLAMF6 | 3 | 0.0004 | SLAM family member 6 | transmembrane receptor | immune | Yes |
| ENSG00000157510.13 | AFAP1L1 | 3 | 0.0009 | actin filament associated protein 1 like 1 | other | intrinsic | No |
| ENSG00000174332.5 | GLIS1 | 3 | 0.0012 | GLIS family zinc finger 1 | transcription regulator | intrinsic | No |
| ENSG00000136770.10 | DNAJC1 | 3 | 0.0012 | DnaJ heat shock protein family (Hsp40) member C1 | other | immune | Yes |
| ENSG00000196411.9 | EPHB4 | 3 | 0.0016 | EPH receptor B4 | kinase | intrinsic | No |
| ENSG00000112697.15 | TMEM30A | 3 | 0.0028 | transmembrane protein 30A | other | immune | Yes |
| ENSG00000166523.7 | CLEC4E | 3 | 0.0032 | C-type lectin domain family 4 member E | other | immune | Yes |
| ENSG00000164715.5 | LMTK2 | 3 | 0.0077 | lemur tyrosine kinase 2 | kinase | intrinsic | No |
| ENSG00000161217.11 | PCYT1A | 3 | 0.0168 | phosphate cytidylyltransferase 1, choline, alpha | enzyme | immune | Yes |
| ENSG00000118242.15 | MREG | 3 | 0.0307 | melanoregulin | other | immune | Yes |
| ENSG00000113249.12 | HAVCR1 | 3 | 0.0311 | hepatitis A virus cellular receptor 1 | other | immune | Yes |
| ENSG00000111653.19 | ING4 | 3 | 0.0350 | inhibitor of growth family member 4 | transcription regulator | intrinsic | No |
| ENSG00000161405.16 | IKZF3 | 2 | 0.0000 | IKAROS family zinc finger 3 | transcription regulator | immune | Yes |
| ENSG00000163568.13 | AIM2 | 2 | 0.0002 | absent in melanoma 2, Interferon-Inducible Protein | other | immune | Yes |

TABLE 7

Performance of Classification Algorithms

| Algorithm | Mean accuracy | Standard deviation |
|---|---|---|
| Randomforest | 0.770 | 0.015 |
| SVM | 0.718 | 0.014 |
| XGBoost | 0.647 | 0.037 |

* 500 runs of 15-fold cross-validation, 55-gene set classification accuracy

TABLE 8A

Variable Signifiance Using Different Cox Models

| | Model 1 | Model 2 | Model 3 |
|---|---|---|---|
| BRAVO score | 7.43E−05 | 0.000277 | NA |
| age | NA | 0.019884 | 0.0167 |
| racegr_cssblack | NA | 0.235679 | 0.387 |
| racegr_cssHispanic white | NA | 0.310774 | 0.2941 |
| racegr_csswhite | NA | 0.609065 | 0.2422 |
| grpajccII | NA | 0.493511 | 0.4919 |
| grpajccIII | NA | 0.295865 | 0.2759 |
| tumorsize | NA | 0.654147 | 0.2775 |
| lymphnode_involyes | NA | 0.459064 | 0.5213 |

TABLE 8B

Comparison Between Models

| | p value (chi square) |
|---|---|
| Model 1 vs Model 2 | 0.3082 |
| Model 2 vs Model 3 | 0.0001204 |

TABLE 11-continued

Probes of Customized TaqMan Real-Time PCR Assay

| Gene | Probe* | Correlation with FPKM from RNA-seq |
|---|---|---|
| HAVCR1 | Hs00273334_m1 | below detection limit |
| IKZF3 | Hs00232635_m1 | 0.9881 |

TABLE 9

External Datasets Used for Validation

| Study | Sample size* | Platform | Survival analysis | Median follow-up (Months)* | Reference |
|---|---|---|---|---|---|
| TCGA | 125 | RNA-seq | Overall survival | 30 | Nature 490.7418 (2012): 61. |
| Gyorffy | 234 | Microarray (Affymetrix HGU133A and HGU133 + 2) | Recurrence-free survival | 68 | Breast Cancer Research and Treatment 123.3 (2010): 725-731 |
| METABRIC | 269 | Microarray (Illumina HT-12 v3) | Overall survival | 110 | Nature 486.7403 (2012): 346. |
| GSE21653 | 67 | Microarray (Affymetrix HGU133 Plus 2.0) | Recurrence-free survival | 52 | Breast Cancer Res Treat 2011 April; 126(2): 407-20 |
| E-MTAB-365 | 51 | Microarray (Affymetrix HGU133 Plus 2.0) | Recurrence-free survival | 51 | Bioinformatics 29(9): 1149 (2013) |

*only include samples with PAM50 classification as Basal

TABLE 10

Survival Status of Low- and High-risk Patient Groups Stratified by Biomarker Gene Sets

| | Gene-set | Number of Low-risk group | Number of High-risk group | 5-year survival | Hazard ratio | Lower limit of hazard ratio | Upper limit of hazard ratio | P value |
|---|---|---|---|---|---|---|---|---|
| TCGA | BRAVO_DX | 75 | 50 | 0.946/0.619* | 6.79 | 1.89 | 24.37 | 0.0007 |
| | BRAVO_IMMUNE | 93 | 32 | 0.932/0.43* | 7.50 | 2.50 | 22.49 | <0.0001 |
| GEO | BRAVO_DX | 161 | 73 | 0.665/0.178 | 3.45 | 2.41 | 4.93 | <0.0001 |
| | BRAVO_IMMUNE | 158 | 76 | 0.684/0.158 | 4.33 | 3.02 | 6.20 | <0.0001 |
| METABRIC | BRAVO_DX | 103 | 166 | 0.771/0.621 | 1.70 | 1.16 | 2.49 | 0.0055 |
| | BRAVO_IMMUNE | 155 | 114 | 0.731/0.606 | 1.46 | 1.03 | 2.06 | 0.0332 |
| METABRIC (NPI <5.4, low-grade) | BRAVO_DX | 100 | 137 | 0.827/0.628 | 1.91 | 1.26 | 2.88 | 0.0018 |
| | BRAVO_IMMUNE | 136 | 101 | 0.784/0.615 | 1.69 | 1.15 | 2.49 | 0.0064 |

TABLE 11

Probes of Customized TaqMan Real-Time PCR Assay

| Gene | Probe* | Correlation with FPKM from RNA-seq |
|---|---|---|
| AFAP1L1 | Hs00827027_m1 | 0.9858 |
| AIM2 | Hs00915710_m1 | 0.983 |
| AIM2 | Hs00175457_m1 | 0.9692 |
| ATP6AP1L | Hs01372641_m1 | 0.9491 |
| ATP6AP1L | Hs01372640_m1 | 0.8393 |
| CLEC4E | Hs00372017_m1 | 0.8359 |
| DNAJC1 | Hs01550854_m1 | 0.9103 |
| DNAJC1 | Hs01550849_m1 | 0.8903 |
| ELF3 | Hs00963881_m1 | 0.986 |
| ELF3 | Hs00231786_m1 | 0.9825 |
| EPHB4 | Hs01119118_g1 | 0.9422 |
| EPHB4 | Hs00174752_m1 | 0.8286 |
| FGF1 | Hs00265254_m1 | 0.8547 |
| FGF1 | Hs01092738_m1 | 0.738 |
| FKBP5 | Hs01561003_m1 | 0.976 |
| FKBP5 | Hs01561006_m1 | 0.9585 |
| GLIS1 | Hs00377690_m1 | 0.925 |
| HAVCR1 | Hs00930379_g1 | 0.8137 |

TABLE 11-continued

Probes of Customized TaqMan Real-Time PCR Assay

| Gene | Probe* | Correlation with FPKM from RNA-seq |
|---|---|---|
| IKZF3 | Hs00918017_m1 | 0.978 |
| ING4 | Hs00211773_m1 | 0.8782 |
| ING4 | Hs01088027_g1 | 0.7332 |
| LMTK2 | Hs00905745_m1 | 0.7828 |
| LMTK2 | Hs00208698_m1 | 0.6208 |
| MKRN2 | Hs00274055_m1 | 0.8412 |
| MREG | Hs00215942_m1 | 0.9422 |
| MREG | Hs01066515_m1 | 0.8877 |
| NCR1 | Hs00950809_g1 | 0.9483 |
| NCR1 | Hs00183118_m1 | 0.9179 |
| PCYT1A | Hs00192339_m1 | 0.9098 |
| PCYT1A | Hs02564656_s1 | 0.9079 |
| RGL2 | Hs00191084_m1 | 0.8906 |
| SLAMF6 | Hs00372941_m1 | 0.9488 |
| SLAMF6 | Hs01559920_m1 | 0.9382 |
| TMEM30A | Hs01092148_m1 | 0.8262 |
| TMEM30A | Hs01097969_m1 | 0.3723 |
| EIF2B1 | Hs00426752_m1 | NA |

TABLE 11-continued

Probes of Customized TaqMan Real-Time PCR Assay

| Gene | Probe* | Correlation with FPKM from RNA-seq |
|------|--------|-------------------------------------|
| CASC3 | Hs00201226_m1 | NA |
| HMBS | Hs00609296_g1 | NA |
| POP4 | Hs00198357_m1 | NA |
| Casc3 | Mm01296308_m1 | NA |
| Hmbs | Mm01143545_m1 | NA |

REFERENCES

1. Perou C M, Sørlie T, Eisen M B, van de Rijn M, Jeffrey S S, Rees C A, et al. Molecular portraits of human breast tumours. Nature. 2000; 406:747-52.
2. The Cancer Genome Atlas Network. Comprehensive molecular portraits of human breast tumours. Nature. 2012; 490:61-70.
3. Curtis C, Shah S P, Chin S-F, Turashvili G, Rueda O M, Dunning M J, et al. The genomic and transcriptomic architecture of 2,000 breast tumours reveals novel subgroups. Nature. 2012; 486:346-52.
4. Sørlie T, Perou C M, Tibshirani R, Aas T, Geisler S, Johnsen H, et al. Gene expression patterns of breast carcinomas distinguish tumor subclasses with clinical implications. Proc Natl Acad Sci USA. 2001; 98:10869-74.
5. Trivers K F, Lund M J, Porter P L, Liff J M, Flagg E W, Coates R J, et al. The epidemiology of triple-negative breast cancer, including race. Cancer Causes Control. 2009; 20:1071-82.
6. Dent R, Trudeau M, Pritchard K I, Hanna W M, Kahn H K, Sawka C A, et al. Triple-negative breast cancer: clinical features and patterns of recurrence. Clin Cancer Res. 2007; 13:4429-34.
7. Sorlie T, Tibshirani R, Parker J, Hastie T, Marron J S, Nobel A, et al. Repeated observation of breast tumor subtypes in independent gene expression data sets. Proc Natl Acad Sci USA. National Academy of Sciences; 2003; 100:8418-23.
8. Gonzalez-Angulo A M, Timms K M, Liu S, Chen H, Litton J K, Potter J, et al. Incidence and outcome of BRCA mutations in unselected patients with triple receptor-negative breast cancer. Clin Cancer Res. 2011; 17:1082-9.
9. Kawazu M, Kojima S, Ueno T, Totoki Y, Nakamura H, Kunita A, et al. Integrative analysis of genomic alterations in triple-negative breast cancer in association with homologous recombination deficiency. PLoS Genet. 2017; 13:e1006853.
10. Shah S P, Roth A, Goya R, Oloumi A, Ha G, Zhao Y, et al. The clonal and mutational evolution spectrum of primary triple-negative breast cancers. Nature. 2012; 486: 395-9.
11. Lin N U, Vanderplas A, Hughes M E, Theriault R L, Edge S B, Wong Y-N, et al. Clinicopathologic features, patterns of recurrence, and survival among women with triple-negative breast cancer in the National Comprehensive Cancer Network. Cancer. Wiley Online Library; 2012; 118:5463-72.
12. Voorwerk L, Slagter M, Horlings H M, Sikorska K, van de Vijver K K, de Maaker M, et al. Immune induction strategies in metastatic triple-negative breast cancer to enhance the sensitivity to PD-1 blockade: the TONIC trial. Nat Med. 2019; 25:920-8.
13. Schmid P, Cortes J, Pusztai L, McArthur H, Kummel S, Bergh J, et al. Pembrolizumab for Early Triple-Negative Breast Cancer. N Engl J Med. 2020; 382:810-21.
14. Adams S, Gray R J, Demaria S, Goldstein L, Perez E A, Shulman L N, et al. Prognostic value of tumor-infiltrating lymphocytes in triple-negative breast cancers from two phase III randomized adjuvant breast cancer trials: ECOG 2197 and ECOG 1199. J Clin Oncol. ncbi.nlm.nih.gov; 2014; 32:2959-66.
15. Loi S, Sirtaine N, Piette F, Salgado R, Viale G, Van Eenoo F, et al. Prognostic and predictive value of tumor-infiltrating lymphocytes in a phase III randomized adjuvant breast cancer trial in node-positive breast cancer comparing the addition of docetaxel to doxorubicin with doxorubicin-based chemotherapy: BIG 02-98. J Clin Oncol. 2013; 31:860-7.
16. Liu S, Lachapelle J, Leung S, Gao D, Foulkes W D, Nielsen T O. CD8+ lymphocyte infiltration is an independent favorable prognostic indicator in basal-like breast cancer. Breast Cancer Res. 2012; 14:R48.
17. Dieci M V, Criscitiello C, Goubar A, Viale G, Conte P, Guarneri V, et al. Prognostic value of tumor-infiltrating lymphocytes on residual disease after primary chemotherapy for triple-negative breast cancer: a retrospective multicenter study. Ann Oncol. 2014; 25:611-8.
18. Denkert C, Loibl S, Noske A, Roller M, Müller B M, Komor M, et al. Tumor-associated lymphocytes as an independent predictor of response to neoadjuvant chemotherapy in breast cancer. J Clin Oncol. 2010; 28:105-13.
19. Denkert C, Von Minckwitz G, Brase J C, Sinn B V, Gade S, Kronenwett R, et al. Tumor-infiltrating lymphocytes and response to neoadjuvant chemotherapy with or without carboplatin in human epidermal growth factor receptor 2-positive and triple-negative primary breast cancers. J Clin Oncol. American Society of Clinical Oncology; 2014; 33:983-91.
20. Ono M, Tsuda H, Shimizu C, Yamamoto S, Shibata T, Yamamoto H, et al. Tumor-infiltrating lymphocytes are correlated with response to neoadjuvant chemotherapy in triple-negative breast cancer. Breast Cancer Res Treat. Springer; 2012; 132:793-805.
21. Li X, Krishnamurti U, Bhattarai S, Klimov S, Reid M, Aneja R. Biomarkers Predicting Pathological Complete Response to Neoadjuvant Chemotherapy in Breast Cancer. LABORATORY INVESTIGATION. NATURE PUBLISHING GROUP 75 VARICK ST, 9TH FLR, NEW YORK, NY 10013-1917 USA; 2016. page 54A-54A.
22. Pelekanou V, Carvajal-Hausdorf D E, Altan M, Wasserman B, Carvajal-Hausdorf C, Wimberly H, et al. Effect of neoadjuvant chemotherapy on tumor-infiltrating lymphocytes and PD-L1 expression in breast cancer and its clinical significance. Breast Cancer Res. 2017; 19:91.
23. Pelekanou V, Barlow W E, von Wahlde M-K, Wasserman B, Lo Y-C, Hayes D F, et al. Effects of neoadjuvant chemotherapy (NAC) on tumor infiltrating lymphocytes (TIL) and PD-L1 expression in the SWOG 50800 clinical trial. J Clin Orthod. American Society of Clinical Oncology; 2017; 35:519-519.
24. Kitano A, Ono M, Yoshida M, Noguchi E, Shimomura A, Shimoi T, et al. Tumour-infiltrating lymphocytes are correlated with higher expression levels of PD-1 and PD-L1 in early breast cancer. ESMO Open. 2017; 2:e000150.
25. Brockhoff G, Seitz S, Weber F, Zeman F, Klinkhammer-Schalke M, Ortmann O, et al. The presence of PD-1 positive tumor infiltrating lymphocytes in triple negative breast cancers is associated with a favorable outcome of disease. Oncotarget. 2018; 9:6201-12.

26. Nanda R, Liu M C, Yau C, Asare S, Hylton N, Veer L V, et al. Pembrolizumab plus standard neoadjuvant therapy for high-risk breast cancer (BC): Results from I-SPY 2. J Clin Orthod. American Society of Clinical Oncology; 2017; 35:506-506.

27. Schmid P, Adams S, Rugo H S, Schneeweiss A, Barrios C H, Iwata H, et al. Atezolizumab and Nab-Paclitaxel in Advanced Triple-Negative Breast Cancer. N Engl J Med. 2018; 379:2108-21.

28. Lee H J, Lee J-J, Song I H, Park I A, Kang J, Yu J H, et al. Prognostic and predictive value of NanoString-based immune-related gene signatures in a neoadjuvant setting of triple-negative breast cancer: relationship to tumor-infiltrating lymphocytes. Breast Cancer Res Treat. 2015; 151:619-27.

29. Gyorffy B, Lanczky A, Eklund A C, Denkert C, Budczies J, Li Q, et al. An online survival analysis tool to rapidly assess the effect of 22,277 genes on breast cancer prognosis using microarray data of 1,809 patients. Breast Cancer Res Treat. 2010; 123:725-31.

30. Baglia M L, Cook L S, Mei-Tzu C, Wiggins C, Hill D, Porter P, et al. Alcohol, smoking, and risk of Her2-overexpressing and triple-negative breast cancer relative to estrogen receptor-positive breast cancer. International Journal of Cancer. 2018; 143:1849-57.

31. Sigurgeirsson B, Emanuelsson O, Lundeberg J. Sequencing degraded RNA addressed by 3' tag counting. PLoS One. 2014; 9:e91851.

32. Karmakar S, Harcourt E M, Hewings D S, Scherer F, Lovejoy A F, Kurtz D M, et al. Organocatalytic removal of formaldehyde adducts from RNA and DNA bases. Nat Chem. 2015; 7:752-8.

33. Cieslik M, Chugh R, Wu Y-M, Wu M, Brennan C, Lonigro R, et al. The use of exome capture RNA-seq for highly degraded RNA with application to clinical cancer sequencing. Genome Res. 2015; 25:1372-81.

34. Paquet E R, Hallett M T. Absolute assignment of breast cancer intrinsic molecular subtype. J Natl Cancer Inst. 2015; 107:357.

35. Perou C M, Parker J S, Prat A, Ellis M J, Bernard P S. Clinical implementation of the intrinsic subtypes of breast cancer. Lancet Oncol. 2010. page 718-9; author reply 720-1.

36. Petralia F, Wang L, Peng J, Yan A, Zhu J, Wang P. A new method for constructing tumor specific gene co-expression networks based on samples with tumor purity heterogeneity. Bioinformatics. 2018; 34:i528-36.

37. Yadav V K, De S. An assessment of computational methods for estimating purity and clonality using genomic data derived from heterogeneous tumor tissue samples. Brief Bioinform. 2015; 16:232-41.

38. Aran D, Sirota M, Butte A J. Systematic pan-cancer analysis of tumour purity. Nat Commun. 2015; 6:8971.

39. Yoshihara K, Shahmoradgoli M, Martinez E, Vegesna R, Kim H, Tones-Garcia W, et al. Inferring tumour purity and stromal and immune cell admixture from expression data. Nature Communications. 2013; 4:1-11.

40. Camarda R, Zhou A Y, Kohnz R A, Balakrishnan S, Mahieu C, Anderton B, et al. Inhibition of fatty acid oxidation as a therapy for MYC-overexpressing triple-negative breast cancer. Nat Med. 2016; 22:427-32.

41. Mori S, Tran V, Nishikawa K, Kaneda T, Hamada Y, Kawaguchi N, et al. A dominant-negative FGF1 mutant (the R50E mutant) suppresses tumorigenesis and angiogenesis. PLoS One. 2013; 8:e57927.

42. Babina I S, Turner N C. Advances and challenges in targeting FGFR signalling in cancer. Nat Rev Cancer. 2017; 17:318-32.

43. Wu Y-M, Su F, Kalyana-Sundaram S, Khazanov N, Ateeq B, Cao X, et al. Identification of targetable FGFR gene fusions in diverse cancers. Cancer Discov. 2013; 3:636-47.

44. Meyer K B, O'Reilly M, Michailidou K, Carlebur S, Edwards S L, French J D, et al. Fine-scale mapping of the FGFR2 breast cancer risk locus: putative functional variants differentially bind FOXA1 and E2F1. Am J Hum Genet. 2013; 93:1046-60.

45. Turner N, Pearson A, Sharpe R, Lambros M, Geyer F, Lopez-Garcia M A, et al. FGFR1 amplification drives endocrine therapy resistance and is a therapeutic target in breast cancer. Cancer Res. 2010; 70:2085-94.

46. Wang J H, Avitahl N, Cariappa A, Friedrich C, Ikeda T, Renold A, et al. Aiolos regulates B cell activation and maturation to effector state. Immunity. 1998; 9:543-53.

47. Pereira M J, Palming J, Svensson M K, Rizell M, Dalenbäck J, Hammar M, et al. FKBP5 expression in human adipose tissue increases following dexamethasone exposure and is associated with insulin resistance. Metabolism. 2014; 63:1198-208.

48. Ring B Z, Hout D R, Morris S W, Lawrence K, Schweitzer B L, Bailey D B, et al. Generation of an algorithm based on minimal gene sets to clinically subtype triple negative breast cancer patients. BMC Cancer. 2016; 16:143.

49. Lehmann B D, Jovanović B, Chen X, Estrada M V, Johnson K N, Shyr Y, et al. Refinement of Triple-Negative Breast Cancer Molecular Subtypes: Implications for Neoadjuvant Chemotherapy Selection. PLoS One. Public Library of Science; 2016; 11:e0157368.

50. Lee T-W. Biomedical Applications of ICA [Internet]. Independent Component Analysis. 1998. page 145-66. Available from: http://dx.doi.org/10.1007/978-1-4757-2851-4_7

51. Newman A M, Liu C L, Green M R, Gentles A J, Feng W, Xu Y, et al. Robust enumeration of cell subsets from tissue expression profiles. Nat Methods. 2015; 12:453-7.

52. Jiang Y-Z, Ma D, Suo C, Shi J, Xue M, Hu X, et al. Genomic and Transcriptomic Landscape of Triple-Negative Breast Cancers: Subtypes and Treatment Strategies. Cancer Cell. Elsevier; 2019; 35:428-40.

53. Hollmén M, Roudnicky F, Karaman S, Detmar M. Characterization of macrophage—cancer cell crosstalk in estrogen receptor positive and triple-negative breast cancer. Sci Rep. 2015; 5:9188.

54. Sousa S, Brion R, Lintunen M, Kronqvist P, Sandholm J, Mönkkonen J, et al. Human breast cancer cells educate macrophages toward the M2 activation status. Breast Cancer Res. 2015; 17:101.

55. Gentles A J, Newman A M, Liu C L, Bratman S V, Feng W, Kim D, et al. The prognostic landscape of genes and infiltrating immune cells across human cancers. Nat Med. 2015; 21:938-45.

56. Wells A D, Gudmundsdottir H, Turka L A. Following the fate of individual T cells throughout activation and clonal expansion. Signals from T cell receptor and CD28 differentially regulate the induction and duration of a proliferative response. J Clin Invest. 1997; 100:3173-83.

57. Kirsch I, Vignali M, Robins H. T-cell receptor profiling in cancer. Mol Oncol. Wiley Online Library; 2015; 9:2063-70.

58. Drukker C A, Bueno-de-Mesquita J M, Retèl V P, van Harten W H, van Tinteren H, Wesseling J, et al. A prospective evaluation of a breast cancer prognosis signature in the observational RASTER study. Int J Cancer. 2013; 133:929-36.

59. Cobleigh M A, Tabesh B, Bitterman P, Baker J, Cronin M, Liu M-L, et al. Tumor Gene Expression and Prognosis in Breast Cancer Patients with 10 or More Positive Lymph Nodes. Clin Cancer Res. American Association for Cancer Research; 2005; 11:8623-31.

60. Dai J, Xu Q. Attribute selection based on information gain ratio in fuzzy rough set theory with application to tumor classification. Appl Soft Comput. 2013; 13:211-21.

61. Liaw A, Wiener M. Classification and regression by randomForest. R news [Internet]. researchgate.net; 2002; Available from: https://www.researchgate.net/profile/Andy_Liaw/publication/228451484_Classification_and_Regression_by_RandomForest/links/53fb24cc0cf20a45497047ab/Classification-and-Regression-by-RandomForest.pdf 62. Elkan C. The foundations of cost-sensitive learning. International joint conference on artificial intelligence. Lawrence Erlbaum Associates Ltd; 2001. page 973-8.

63. Schaefer G, Nakashima T, Yokota Y. Cost-Sensitive Classification for Medical Diagnosis [Internet]. Encyclopedia of Healthcare Information Systems. Available from: http://dx.doi.org/10.4018/9781599048895.ch040

64. Rody A, Karn T, Liedtke C, Pusztai L, Ruckhaeberle E, Hanker L, et al. A clinically relevant gene signature in triple negative and basal-like breast cancer. Breast Cancer Res. 2011; 13:R97.

65. Kardos J, Chai S, Mose L E, Selitsky S R, Krishnan B, Saito R, et al. Claudin-low bladder tumors are immune infiltrated and actively immune suppressed. JCI Insight. 2016; 1:e85902.

66. Sparano J A, Gray R J, Makower D F, Pritchard K I, Albain K S, Hayes D F, et al. Prospective Validation of a 21-Gene Expression Assay in Breast Cancer. N Engl J Med. 2015; 373:2005-14.

67. Sparano J A, Gray R J, Makower D F, Pritchard K I, Albain K S, Hayes D F, et al. Adjuvant Chemotherapy Guided by a 21-Gene Expression Assay in Breast Cancer. N Engl J Med. 2018; 379:111-21.

68. Gluz O, Nitz U A, Christgen M, Kates R E, Shak S, Clemens M, et al. West German Study Group Phase III PlanB Trial: first prospective outcome data for the 21-gene recurrence score assay and concordance of prognostic markers by central and local pathology assessment. J Clin Oncol. 2016; 34:2341-9.

69. Parker J S, Mullins M, Cheang M C U, Leung S, Voduc D, Vickery T, et al. Supervised risk predictor of breast cancer based on intrinsic subtypes. J Clin Oncol. 2009; 27:1160-7.

70. Dubsky P, Brase J C, Jakesz R, Rudas M, Singer C F, Greil R, et al. The EndoPredict score provides prognostic information on late distant metastases in ER+/HER2– breast cancer patients. Br J Cancer. 2013; 109:2959-64.

71. Sgroi D C, Carney E, Zarrella E, Steffel L, Binns S N, Finkelstein D M, et al. Prediction of late disease recurrence and extended adjuvant letrozole benefit by the HOXB13/IL17BR biomarker. J Natl Cancer Inst. 2013; 105:1036-42.

72. Harris L N, Ismaila N, McShane L M, Andre F, Collyar D E, Gonzalez-Angulo A M, et al. Use of Biomarkers to Guide Decisions on Adjuvant Systemic Therapy for Women With Early-Stage Invasive Breast Cancer: American Society of Clinical Oncology Clinical Practice Guideline. J Clin Orthod. American Society of Clinical Oncology; 2016; 34:1134-50.

73. Krop I, Ismaila N, Stearns V. Use of biomarkers to guide decisions on adjuvant systemic therapy for women with early-stage invasive breast cancer: American Society of Clinical Oncology clinical practice focused update guideline summary. J Oncol Pract. American Society of Clinical Oncology; 2017; 13:763-6.

74. Cabrita R, Lauss M, Sanna A, Donia M, Skaarup Larsen M, Mitra S, et al. Tertiary lymphoid structures improve immunotherapy and survival in melanoma. Nature [Internet]. 2020; Available from: https://doi.org/10.1038/s41586-019-1914-8

75. Petitprez F, de Reyniès A, Keung E Z, Chen T W-W, Sun C-M, Calderaro J, et al. B cells are associated with survival and immunotherapy response in sarcoma. Nature [Internet]. 2020; Available from: https://doi.org/10.1038/s41586-019-1906-8

76. Helmink B A, Reddy S M, Gao J, Zhang S, Basar R, Thakur R, et al. B cells and tertiary lymphoid structures promote immunotherapy response. Nature [Internet]. 2020; Available from: https://doi.org/10.1038/s41586-019-1922-8

77. Robinson D, Van Allen E M, Wu Y-M, Schultz N, Lonigro R J, Mosquera J-M, et al. Integrative clinical genomics of advanced prostate cancer. Cell. 2015; 161: 1215-28.

78. Robinson D R, Wu Y-M, Lonigro R J, Vats P, Cobain E, Everett J, et al. Integrative clinical genomics of metastatic cancer. Nature. 2017; 548:297-303.

79. Dobin A, Davis C A, Schlesinger F, Drenkow J, Zaleski C, Jha S, et al. STAR: ultrafast universal RNA-seq aligner. Bioinformatics. 2013; 29:15-21.

80. Searle S, Frankish A, Bignell A, Aken B, Derrien T, Diekhans M, et al. The GENCODE human gene set. Genome Biol. 2010; 11:1-1.

81. Liao Y, Smyth G K, Shi W. featureCounts: an efficient general purpose program for assigning sequence reads to genomic features. Bioinformatics. 2013; btt656.

82. Robinson M D, Oshlack A. A scaling normalization method for differential expression analysis of RNA-seq data. Genome Biol. 2010; 11:R25.

83. Ciriello G, Gatza M L, Beck A H, Wilkerson M D, Rhie S K, Pastore A, et al. Comprehensive Molecular Portraits of Invasive Lobular Breast Cancer. Cell. 2015; 163:506-19.

84. Gendoo D M A, Ratanasirigulchai N, Schroder M S, Pare L, Parker J S, Prat A, et al. Genefu: an R/Bioconductor package for computation of gene expression-based signatures in breast cancer. Bioinformatics. 2016; 32:1097-9.

85. Ritchie M E, Phipson B, Wu D, Hu Y, Law C W, Shi W, et al. limma powers differential expression analyses for RNA-sequencing and microarray studies. Nucleic Acids Res. 2015; 43:e47.

86. Law C W, Chen Y, Shi W, Smyth G K. voom: precision weights unlock linear model analysis tools for RNA-seq read counts. Genome Biol. 2014; 15:R29.

87. Sergushichev A. An algorithm for fast preranked gene set enrichment analysis using cumulative statistic calculation [Internet]. bioRxiv. 2016 [cited 2017 Nov. 20]. page 060012. Available from: http://biorxiv.org/content/early/2016/06/20/060012

88. Liberzon A, Birger C, Thorvaldsdóttir H, Ghandi M, Mesirov J P, Tamayo P. The Molecular Signatures Database (MSigDB) hallmark gene set collection. Cell Syst. 2015; 1:417-25.

89. Aran D, Hu Z, Butte A J. xCell: digitally portraying the tissue cellular heterogeneity landscape. Genome Biol. 2017; 18:220.

90. Helwig N E. ica: Independent Component Analysis. R package version; 2015.

91. Bolotin D A, Poslaysky S, Mitrophanov I, Shugay M, Mamedov I Z, Putintseva E V, et al. MiXCR: software for comprehensive adaptive immunity profiling. Nat Methods. 2015; 12:380-1.

92. Wang Y, Tetko I V, Hall M A, Frank E, Facius A, Mayer K F X, et al. Gene selection from microarray data for cancer classification—a machine learning approach. Comput Biol Chem. 2005; 29:37-46.

93. Yu L, Liu H. Feature selection for high-dimensional data: A fast correlation-based filter solution. Proceedings of the 20th international conference on machine learning (ICML-03). 2003. page 856-63.

94. Novoselova N, Wang J, Pessler F, Klawonn F. Biocomb: Feature Selection and Classification with the Embedded Validation Procedures for Biomedical Data Analysis. R Package Version 0 4 Available online: https://CRAN R-project org/package=Biocomb (accessed on 1 Oct. 2018). 2018;

95. Chen T, He T. Xgboost: extreme gradient boosting. R package version 0 4-2 [Internet]. 2015; Available from: http://cran.fhcrc.org/web/packages/xgboost/vignettes/xgboost.pdf 96. Bischl B, Lang M, Kotthoff L, Schiffner J, Richter J, Studerus E, et al. mlr: Machine learning in R. J Mach Learn Res. 2016; 17:1-5.

97. Dunning M J, Smith M L, Ritchie M E, Tavaré S. beadarray: R classes and methods for Illumina bead-based data. Bioinformatics. 2007; 23:2183-4.

98. Sabatier R, Finetti P, Cervera N, Lambaudie E, Esterni B, Mamessier E, et al. A gene expression signature identifies two prognostic subgroups of basal breast cancer. Breast Cancer Res Treat. 2011; 126:407-20.

99. Davis S, Meltzer P S. GEOquery: a bridge between the Gene Expression Omnibus (GEO) and BioConductor. Bioinformatics. 2007; 23:1846-7.

100. Guedj M, Marisa L, de Reynies A, Orsetti B, Schiappa R, Bibeau F, et al. A refined molecular taxonomy of breast cancer. Oncogene. 2012; 31:1196-206.

101. Grambsch P M, Therneau T M. Modeling survival data: extending the Cox model. Stat Biol Health. 2000

We claim:

1. A method of detecting expression levels of cancer markers, consisting of:
   assaying the level of expression of makorin ring finger protein 2 (MKRN2), ral guanine nucleotide dissociation stimulator like 2 (RGL2), fibroblast growth factor 1 (FGF1), FK506 binding protein 5 (FKBP5), ATPase H+ transporting accessory protein 1 like (ATP6AP1L), E74 like ETS transcription factor 3 (ELF3), natural cytotoxicity triggering receptor 1 (NCR1), SLAM family member 6 (SLAMF6), actin filament associated protein 1 like 1 (AFAP1L1), GLIS family zinc finger 1 (GLIS1), DnaJ heat shock protein family (Hsp40) member C1 (DNAJC1), EPH receptor B4 (EPHB4), transmembrane protein 30A (TMEM30A), C-type lectin domain family 4 member E (CLEC4E), lemur tyrosine kinase 2 (LMTK2), phosphate cytidylyltransferase 1, choline, alpha (PCYT1A), melanoregulin (MREG), hepatitis A virus cellular receptor 1 (HAVCR1), inhibitor of growth family member 4 (ING4), IKAROS family zinc finger 3 (IKZF3), and absent in melanoma 2, Interferon-Inducible Protein (AIM2) in a sample from a subject diagnosed with breast cancer.

2. The method of claim 1, wherein said expression is the level of mRNA or protein expressed by said cancer marker.

3. The method of claim 1, wherein said sample is selected from the group consisting of tissue, blood, plasma, serum, breast tissue, breast cells, and breast cancer cells.

4. The method of claim 1, wherein said assaying is carried out utilizing a method selected from the group consisting of a sequencing technique, a nucleic acid hybridization technique, and a nucleic acid amplification technique.

5. The method of claim 4, wherein the nucleic acid amplification technique is selected from the group consisting of polymerase chain reaction, reverse transcription polymerase chain reaction, transcription-mediated amplification, ligase chain reaction, strand displacement amplification, and nucleic acid sequence based amplification.

6. The method of claim 4, wherein said assaying comprises the use of a reagent selected from the group consisting of a pair of amplification oligonucleotides, a sequencing primer, and an oligonucleotide probe.

7. The method of claim 6, wherein said reagent comprises one or more labels.

* * * * *